US007160902B2

(12) United States Patent
Dolle et al.

(10) Patent No.: US 7,160,902 B2
(45) Date of Patent: Jan. 9, 2007

(54) AMIDE DERIVATIVES AND METHODS OF THEIR USE

(75) Inventors: Roland E. Dolle, King of Prussia, PA (US); Guo-Hua Chu, Wilmington, DE (US); Minghua Gu, Collegeville, PA (US)

(73) Assignee: Adolor Corporation, Exton, PA (US)

( * ) Notice: Subject to any disclaimer, the term of this patent is extended or adjusted under 35 U.S.C. 154(b) by 523 days.

(21) Appl. No.: 10/713,746

(22) Filed: Nov. 14, 2003

(65) Prior Publication Data

US 2005/0107355 A1 May 19, 2005

(51) Int. Cl.
| | |
|---|---|
| C07D 207/12 | (2006.01) |
| C07D 401/06 | (2006.01) |
| C07D 403/12 | (2006.01) |
| C07D 417/12 | (2006.01) |
| A61K 31/40 | (2006.01) |
| A61K 31/427 | (2006.01) |
| A61K 31/4439 | (2006.01) |
| A61K 31/454 | (2006.01) |

(52) U.S. Cl. ............... 514/326; 514/343; 514/371; 514/422; 514/424; 546/207; 546/278.4; 548/195; 548/523; 548/556

(58) Field of Classification Search ........... 546/207, 546/278.4; 548/195, 523, 556; 514/326, 514/343, 371, 422, 424
See application file for complete search history.

(56) References Cited

U.S. PATENT DOCUMENTS

| | | | |
|---|---|---|---|
| 4,065,573 A | 12/1977 | Lednicer | 424/278 |
| 4,098,904 A | 7/1978 | Szmuszkovicz | 424/324 |
| 4,145,435 A | 3/1979 | Szmuszkovicz | 424/274 |
| 4,212,878 A | 7/1980 | Lednicer et al. | 424/274 |
| 4,359,476 A | 11/1982 | Kaplan et al. | 424/274 |
| 4,438,130 A | 3/1984 | Kaplan | 424/274 |
| 4,663,343 A | 5/1987 | Horwell et al. | 514/429 |
| 4,906,655 A | 3/1990 | Horwell et al. | 514/422 |
| 5,109,135 A | 4/1992 | D'Ambra et al. | 544/73 |
| 5,242,944 A | 9/1993 | Park et al. | 514/466 |
| 5,345,943 A | 9/1994 | Hargreaves et al. | 128/742 |
| 5,369,131 A | 11/1994 | Poli et al. | 514/772.4 |
| 5,434,292 A | 7/1995 | Saita et al. | 560/51 |
| 5,532,266 A | 7/1996 | Gottschlich et al. | 514/428 |
| 5,688,955 A | 11/1997 | Kruse et al. | 546/276.4 |
| 5,776,972 A * | 7/1998 | Barber et al. | 514/424 |
| 5,804,595 A | 9/1998 | Portoghese et al. | 514/428 |
| 6,117,438 A | 9/2000 | Topolkaraev et al. | 424/404 |
| 6,423,689 B1 * | 7/2002 | Booth et al. | 514/19 |
| 6,855,706 B1 * | 2/2005 | Tanaka et al. | 514/210.17 |
| 6,992,193 B1 * | 1/2006 | Le Bourdonnec et al. | 548/207 |

FOREIGN PATENT DOCUMENTS

JP  11-180950  7/1999

| | | | |
|---|---|---|---|
| JP | 2002-173485 | | 6/2002 |
| WO | WO 01/44179 | * | 6/2001 |

OTHER PUBLICATIONS

Andreev, N., et al., "Opioids suppress spontaneous activity of polymodal nociceptors in rat paw skin induced by ultraviolet irradiation," *Neurosci.*, 1994, 58(4), 793-798.

Antonijevic, I.et al., "Perineurial defect and peripheral opioid analgesia in inflammation," *J. Neurosci.*, Jan. 1995, 15(1), 165-172.

Barber, A., et al., "Opioid agonists and antagonists: an evaluation of their peripheral actions in inflammation," *Med. Res. Rev.*, 1992, 12(5), 525-562.

Flynn, G.L., "Mechanism of percutaneous absorption from physicochemical evidence," Percutaneous Absorption, Maibach, H.I., et al. (Eds.), *Marcel Dekker Inc.*, 1985, 17-42.

Handwerker, et al., Pain and Inflammation, Proceeding of the VIth World Congress on Pain, Bond, et al. (Eds.), *Elsevier Science Publishers BV*, 1990, 59-70.

Hargreaves, K.M., et al., "The peripheral analgesic effects of opioids," *APS Journal*, 1993, 2(1), 51-59.

Hassan, A.H.S., et al., "Inflammation of the rat paw enhances axonal transport of opioid receptors in the sciatic nerve and increase their density in the inflamed tissue," *Neuroscience*, 1993, 55(1), 185-193.

Iyengar, S., et al., "Kappa opiate agonists modulate the hypothalamic-pituitary-adrenocortical axisin the rat," *J. Pharmacol. Exp. Ther.*, 1986, 238(2), 429-436.

Jain, K.K., "A guide to Drug Evaluation for chronic pain," *Emerging Drugs*, 2000, 5(2), 241-257.

(Continued)

*Primary Examiner*—Fiona T. Powers
(74) *Attorney, Agent, or Firm*—Woodcock Washburn LLP

(57) ABSTRACT

Amide derivatives of the general formulae Ia and Ib:

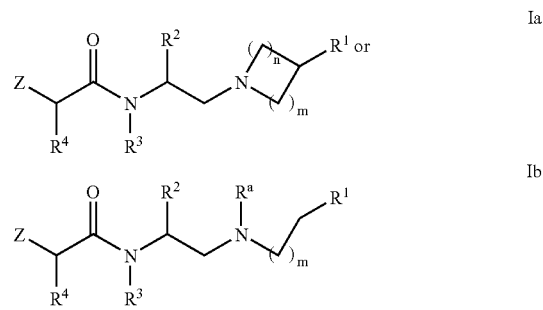

are disclosed. Pharmaceutical compositions containing these compounds, and methods for their use, inter alia, for treating and/or preventing gastrointestinal disorders, pain, and pruritus are also disclosed.

46 Claims, No Drawings

OTHER PUBLICATIONS

Leander, J.D., et al., "Diuresis and suppression of vasopressin by kappa opioids: comparison with Mu and Delta opioids and clonidine," *J. Pharm. Exp. Ther.*, 1985, 234, 463-469.

Lurz, R.A., et al., "Opioid reepors and eir parmaologial profiles," *J. of Recept. Res.*, 1992 12(3), 267-286.

Mansour, A., et al., "Anatomical distribution of opioid receptors in mammalians, an overview," *Opioid I*, 1993, 79-105.

Manzanares, J., et al., "Kappa-opioid-receptor-mediated regulation of α-melanocyte-stimulating hormone secretion and tuberohypophysial dopaminergic neuronal activity," *Neuroendocrinology*, 1990, 52, 200-205.

Millan, M.J., "κ-opioid receptors and analgesia," *Trends in Pharmacol. Sci.*, 1990, 11, 70-76.

Morley, J.E., et al., "Involvement of dynorphin and the kappa opioid receptor in feeding," *Peptides*, 1983, 4, 797-800.

Neugebauer, V., et al., "N-methyl-D-aspartate (NMDA) and non-NMDA receptor antagonists block the hyperexcitability of dorsal horn neurons during development of acute arthritis in rat's knee joint," *J. Neurosci.*, Oct. 1993, 70(4), 1365-1377.

Pershing, L.K., et al., "In vivo pharmacokinetics and pharmacodynamics of topical ketoconazole and miconazole in human stratum corneum," *Antimicrob. Agents Chemother.*, Jan. 1994, 38(1), 90-95.

Przewlocki, R., et al., "Gene expression and localization of opioid peptides in immune cells of inflamed tissue: functional role in antinociception," *Neuroscience*, 1992, 48(2), Pergamon Press Ltd., 491-500.

Ramabadran, K., et al., "A critical analysis of the experimental evaluation of nociceptive reactions in animals," *Pharm. Res.*, 1986, 3(5), 263-270.

Roy, S.D., et al., "Transdermal delivery of narcotic analgesics: pH, anatomical, and subject influences on cutaneous permeability of fentanyl and sufentanil," *Pharm. Res.*, 1990, 7(8), 842-847.

Sato, A., et al., "Changes in blood pressure and heart rate induced by movements of normal and inflamed knee joints," *Neurosci. Lett.*, 1984, 52, 55-60.

Schaible, H.-G., et al., "Effects of an experimental arthritis on the sensory properties of fine articular afferent units," *J. of Neurophysiol.*, 1985, 54(5), 1109-1122.

Schaible, H.-G.et al., "Afferent and spinal mechanisms of joint pain,"*Pain*, 1993, 55, 5-54.

Simon, E.J., "Opioid receptors and endogenous opioid peptides," *Med. Res. Rev.*, 1991, 11(4), 357-374.

Stein, C., et al., "Peripheral opioid receptors mediating antinociception in inflammation. Evidence for involvement of MU, Delta, and Kappa receptors," *J. Pharmacol. Exp. Ther.*, 1989,248(3), 1269-1275.

Stein, C., et al., "Peripheral effect of fentanyl upon nociception in inflamed tissue of the rat," *Neurosci. Lett.*, 1988, 84, 225-228.

Stein, C., et al., "Unilateral inflammation of the hindpaw in rats as a model of prolonged noxious stimulation: alterations in behavior and nociceptive thresholds," *Pharmacol. Biochem. & Behav.*, 1988, 31, 445-451.

Taber, R.I., et al., "Agonist and antagonist interactions of opioids on acetic acid-induced abdominal stretching in mice," *J. or Pharmacol. Exp. Ther.*, 1969, 169(1), 29-38.

Tjølsen, A., et al., "The formalin test: an evaluation of the method," *Pain*, 1992, 51, 5-17.

Wheeler-Aceto, H., et al., "Standardization of the rat paw formalin test for the evaluation of analgesics," *Psychopharmacology*, 1991, 104, 35-44.

Williamson, J.W., et al, "Reflex increase in blood pressure induced by leg compression in man," *J. Physiol.*, 1994, 475.2, 351-357.

Wood, P.L., "Multiple opiate receptors: Support for unique Mu, Delta and Kappa sites," *Neuropharmacology*, 1982, 21, 487-497.

* cited by examiner

AMIDE DERIVATIVES AND METHODS OF THEIR USE

FIELD OF THE INVENTION

The invention relates to certain amide derivatives, pharmaceutical compositions containing these compounds, and methods for their pharmaceutical use. In certain embodiments, the amide derivatives are agonists of the κ opioid receptor and are useful, inter alia, for treating and/or preventing gastrointestinal disorders, pain, and pruritus.

BACKGROUND OF THE INVENTION

Opium and its derivatives are potent analgesics that also have other pharmacological effects, and exert their effects by interacting with high-affinity receptors. It has been shown by investigators that there are at least three major opioid receptor types in the central nervous system (hereinafter CNS) and in the periphery. These receptors, known as mu (μ), delta (δ) and kappa (κ), have distinct pharmacological profiles, anatomical distributions and functions. See, for example: Wood, P. L., Neuropharmacology, 21, 487–497, 1982; Simon, E. J., Med. Res. Rev., 11, 357–374, 1991; Lutz et al., J. Recept. Res. 12, 267–286; and Mansour et al., Opioid I, ed. Herz, A. (Springer, Berlin) 79–106, 1993. The δ receptors are abundant in the CNS and mediate analgesia, gastrointestinal motility and various hormonal functions. The μ receptors bind morphine-like drugs and mediate the opiate phenomena associated with morphine, including analgesia, opiate dependence, cardiovascular and respiratory functions, and several neuroendocrine effects. The κ receptors have a wide distribution in CNS and mediate a spectrum of functions including the modulation of drinking, water balance, food intake, tussis, gut motility, temperature control and various endocrine functions. They also produce analgesia. See, for example: Leander et al., J. Pharmacol. Exp. Ther. 234, 463–469, 1985; Morley et al., Peptides 4, 797–800, 1983; Manzanares, et al., Neuroendocrinology 52, 200–205, 1990; and Iyengar et al., J. Pharmacol. Exp. Ther, 238, 429–436, 1986; and U.S. Pat. No. 6,177,438.

Most clinically used opioid analgesics, such as morphine and codeine, act as μ receptor agonists. These opioids have well-known, undesirable and potentially dangerous dependence forming side effects. Compounds that are κ-receptor agonists act as analgesics through interaction with κ opioid receptors. The advantage of these agonists over the classical μ receptor agonists, such as morphine, lies in their ability to cause analgesia while being devoid of morphine-like behavioral effects and addiction liability.

A large number of classes of compounds that act as agonists at κ opioid receptors have been described in the art including the following illustrative classes of compounds:

U.S. Pat. No. 4,065,573 discloses 4-amino-4-phenylcyclohexane ketal compounds allegedly having analgesic activity.

U.S. Pat. No. 4,145,435 discloses N-(2-amino-cycloaliphatic)-phenylacetamide compounds allegedly having analgesic activity and narcotic antagonist activity.

U.S. Pat. No. 4,098,904 discloses N-(2-amino-cycloaliphatic)-benzoamides and naphthamides allegedly useful for relieving pain.

U.S. Pat. No. 4,212,878 discloses phenylacetamide derivatives allegedly having analgesic properties and reduced physical dependence liability properties, relative to morphine and methadone.

U.S. Pat. No. 4,359,476 discloses substituted cycloalkane-amides allegedly useful as analgesic and having low abuse liability.

U.S. Pat. No. 4,438,130 discloses 1-oxa-, aza- and thiaspirocyclic compounds allegedly having analgesic activity, low physical dependence and abuse liability properties and little dysphoric inducing properties.

U.S. Pat. No. 4,663,343 discloses substituted naphthalenyloxy-1,2-diaminocyclohexyl amides allegedly useful as analgesics.

U.S. Pat. No. 4,906,655 discloses 1,2-cyclohexylaminoaryl amides allegedly having high κ-opioid affinity, selectivity and potency and allegedly useful as analgesics, diuretics, anti-inflammatory and psychotherapeutic agents.

U.S. Pat. No. 5,532,266 discloses arylacetamides allegedly having high κ-opioid affinity useful as pharmaceutical agents for providing an analgesic effect and/or neuroprotective effect.

U.S. Pat. No. 5,688,955 discloses substituted piperidines, substituted naphthalenes, aryl-substituted amides, and cyclohexyl-substituted amides having κ opioid agonist activity, compositions containing them and methods of using them as analgesics.

U.S. Pat. No. 5,804,595 discloses amino acid conjugates of substituted 2-phenyl-N-[1-(phenyl)-2-(1-heterocycloalkyl- or heterocycloaryl-)ethyl]acetamides allegedly useful for selectively agonizing κ opioid receptors in mammalian tissue.

There is still an unfulfilled need for compounds with κ opioid receptor activity that may be used in methods to provide beneficial pharmaceutical characteristics while minimizing undesirable side effects generally associated with administering exogenous opioids. The present invention is directed to these, as well as other important ends.

SUMMARY OF THE INVENTION

The present invention is generally directed to amide derivatives, pharmaceutical compositions containing these compounds, and methods for their pharmaceutical use.

In one embodiment, the invention is directed to compounds of formula Ia or Ib:

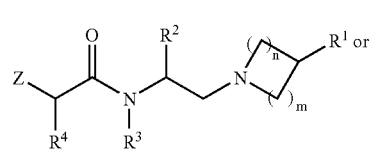

Ia

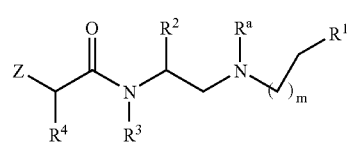

Ib wherein:

$R^1$ is H or OH;

$R^a$ is alkyl;

$R^2$ is alkyl, aryl, or aralkyl;

$R^3$ is alkyl, or $R^2$ and $R^3$ taken together with the atoms through which they are connected form a 4 to 8-membered heterocyclic ring;

$R^4$ is H, alkyl, cycloalkyl, alkylcycloalkyl, aryl, aralkyl, heteroaryl, or heteroarylalkyl;

Z is $—(CH_2)_o—NR^5R^6$ or $—(CH_2)_o—C(=O)NR^7R^8$;

$R^5$ is H, alkyl or aryl;

$R^6$ is aryl, alkaryl, $—CO(NH)_pR^9$, or $—SO_2R^9$, provided that at least one of $R^5$ and $R^6$ is other than aryl;

$R^7$ is H or alkyl;

$R^8$ is alkyl, aryl, aralkyl, alkaryl, heteroaryl, heteroarylalkyl, cycloalkyl, or cycloalkylalkyl;

$R^9$ is alkyl, cycloalkyl, alkylcycloalkyl, aryl, aralkyl, heteroaryl, or heteroarylalkyl;

m is the integer 1, 2, or 3;

n is the integer 1, 2, or 3;

o is the integer 0, 1, 2, or 3;

p is the integer 0 or 1; and the quantity (m+n) is an integer in the range of 2 to 5;

or a stereoisomer, prodrug, pharmaceutically acceptable salt, hydrate, solvate, acid salt hydrate, N-oxide or isomorphic crystalline form thereof.

In another embodiment, the invention is directed to pharmaceutical compositions comprising at least one pharmaceutically acceptable carrier and at least one compound of formula Ia or Ib. In certain preferred embodiments, the pharmaceutical compositions may further comprise at least one opioid and/or at least one other active ingredient selected from the group consisting of antibiotics, antivirals, antifungals, anti-inflammatories, anesthetics and mixtures thereof.

In another embodiment, the invention is directed to compounds of formula IIa or IIb:

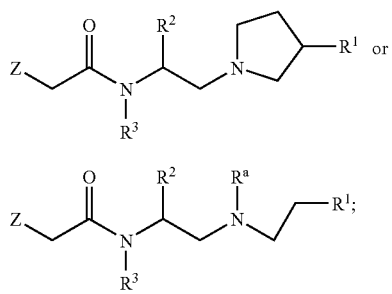

wherein the substituents are defined as above.

In other embodiments, the invention is directed to compounds of formula IIc or IId:

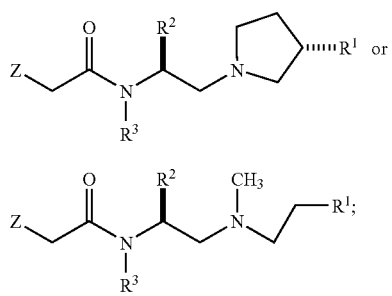

wherein the substituents are defined as above.

In another embodiment, the invention is directed to compounds of formula III:

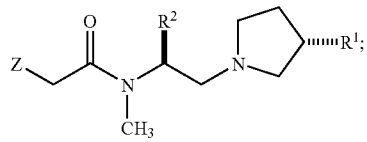

wherein the substituents are defined as above.

In another embodiment, the invention is directed to methods of binding opioid receptors, including κ opioid receptors, comprising the step of administering to a patient in need of such treatment, an effective amount of at least one compound of formula Ia or Ib.

In yet another embodiment, the invention is directed to methods for preventing or treating gastrointestinal dysfunction, comprising the step of administering to a patient in need of such treatment, an effective amount of at least one compound of formula Ia or Ib.

In other embodiments, the invention is directed to methods for preventing or treating ileus, comprising the step of administering to a patient in need of such treatment, an effective amount of at least one compound of formula Ia or Ib.

In another embodiment, the invention is directed to methods for preventing or treating pain, comprising the step of administering to a patient in need of such treatment, an effective amount of at least one compound of formula Ia or Ib.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need of such treatment, an effective amount of at least one compound of formula Ia or Ib.

In another embodiment, the invention is directed to methods for preventing or treating cerebral edema, comprising the step of administering to a patient in need of such treatment, an effective amount of at least one compound of formula Ia or Ib.

In other embodiments, the invention is directed to methods for preventing or treating oxygen supply deficiency of the central nervous system, comprising the step of administering to a patient in need of such treatment, an effective amount of at least one compound of formula Ia or Ib.

In another embodiment, the invention is directed to methods for inducing diuresis, comprising the step of administering to a patient in need of such treatment, an effective amount of at least one compound of formula Ia or Ib.

In yet another embodiment, the invention is directed to methods for preventing or treating tussis, comprising the step of administering to a patient in need of such treatment, an effective amount of at least one compound of formula Ia or Ib.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl," being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkenyl" refers to an alkyl group of at least 2 carbon atoms having one or more double bonds, wherein alkyl is as previously defined. Alkenyl groups can be optionally substituted.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. In some embodiments, aryl is preferably substituted or unsubstituted phenyl.

As used herein, "perhaloalkyl" refers to an alkyl group, wherein all of the hydrogens are replaced by halo (F, Cl, Br, I, or combinations) atoms, and alkyl is as previously defined.

As used herein, "aralkyl" refers to alkyl radicals bearing an aryl substituent and having from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, "alkaryl" refers to an optionally substituted, mono-, di-, tri-, or other multicyclic aryl radical bearing one or more alkyl substituents and having from about 5 to about 50 carbon atoms (and all combinations and subcombinations of ranges and specific numbers of carbon atoms therein), and wherein aryl and alkyl are as previously defined. In some preferred embodiments, the alkyl moieties of the alkaryl groups have from about 1 to about 4 carbon atoms and these alkyl moieties may be substituted or unsubstituted. In some other preferred embodiments the alkyl moiety is methyl. In some even more preferred embodiments, the methyl is substituted. The aryl moieties of alkaryl groups may be optionally substituted. Exemplary alkaryl groups include, but are not limited to, tolyl, xylyl, 1-methylnaphthyl, 9-ethylanthracenyl, and 2,4-dimethylphenanthrenyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, and adamantyl.

As used herein, "alkylcycloalkyl" refers to an optionally substituted ring system comprising a cycloalkyl group having one or more alkyl substituents. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4, -tetrahydroquinolyl, octahydro-[2] pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro [4.7]dodecane.

As used herein, "alkoxy" and "alkoxyl" refer to an optionally substituted alkyl-O-group wherein alkyl is as previously defined. Exemplary alkoxy and alkoxyl groups include methoxy, ethoxy, n-propoxy, i-propoxy, n-butoxy, and heptoxy.

As used herein, "aryloxy" and "aryloxyl" refer to an optionally substituted aryl-O-group wherein aryl is as previously defined. Exemplary aryloxy and aryloxyl groups include phenoxy and naphthoxy.

As used herein, "aralkoxy" and "aralkoxyl" refer to an optionally substituted aralkyl-O-group wherein aralkyl is as previously defined. Exemplary aralkoxy and aralkoxyl groups include benzyloxy, 1-phenylethoxy, 2-phenylethoxy, and 3-naphthylheptoxy.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH2, S(=O)$_2$NHR", S(=O)$_2$NR"R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, "opioid" refers to all agonist and antagonists with morphine-like activity as well as to naturally occurring and synthetic opioid peptides. Non-limiting examples of compounds with morphine-like activity include the family of drugs derived from opium, such as for example, morphine and codeine, thebaine, and a wide variety of semi synthetic related compounds derived therefrom.

As used herein, "analgesic" refers to pharmaceutical compounds that have the ability to reduce or eliminate pain and/or the perception of pain without a loss of consciousness.

As used herein, "effective amount" refers to an amount of a compound as described herein that may be therapeutically effective to inhibit, prevent, or treat the symptoms of a particular disease, disorder, condition, or side effect. Such diseases, disorders, conditions, and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount," when used in connection with opioids, or opioid replacements, for example, for the treatment of pain, refers to the treatment and/or prevention of the painful condition. The term "effective amount," when used in connection with anti-pruritic compounds, refers to the treatment and/or prevention of symptoms, diseases, disorders, and conditions typically associated with pruritus and other related dermatoses. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with anti-ileus compounds, refers to the treatment and/or prevention of symptoms, diseases, disorders, and conditions typically associated with ileus. The term "effective amount," when used in connection with compounds useful in the treatment and/or prevention of cerebral edema, refers to the treatment and/or prevention of symptoms, diseases, disorders, and conditions typically associated with cerebral edema and other related conditions. The term "effective amount," when used in connection with anti-hypoxia compounds, refers to the treatment and/or prevention of symptoms, diseases, disorders, and conditions typically associated with hypoxia, such as oxygen supply deficiency to the central nervous system. The term "effective amount," when used in connection with anti-tussive compounds, refers to the treatment and/or prevention of tussis. The term "effective amount," when used in connection with diuretic compounds, refers to the inducement of diuresis.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with," "combination therapy," and "combination products" refer, in certain embodiments, to the concurrent administration to a patient of opioids and the compounds of formula Ia or Ib. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "gastrointestinal dysfunction" refers collectively to maladies of the stomach, small and large intestine. Non-limiting examples of gastrointestinal dysfunction include, for example, irritable bowel syndrome, opioid-bowel dysfunction, post-operative ileus, opioid-induced ileus, colitis, post-operative emesis, opioid-induced emesis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, or delayed absorption of orally administered medications or nutritive substances.

As used herein, "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim, 2002; Jain, K. K. "A Guide to Drug Evaluation For Chronic Pain"; *Emerging Drugs*, 5(2), 241–257(2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, allodynia and the like.

As used herein, "pruritus" refers to a symptom of a disease, disorder, or condition which is manifested by itching, that is, an uncomfortable sensation due to irritation of a peripheral sensory nerve.

As used herein, "tussis" refers to a coughing condition, and "antitussive" agents refer to those materials that modulate the coughing response.

As used herein, "diuretic" refers to an agent that modulates the water balance in a patient.

As used herein, "pruritic dermatosis" refers to any skin diseases, disorders, or conditions of which itching is a symptom. Non-limiting examples include allergic dermatitis, atopy, contact dermatitis, psoriasis, eczema, opioid-induced pruritus, uremic pruritus, and insect bites.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulae and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

Accordingly, in one embodiment, the invention provides compounds of formula Ia or Ib:

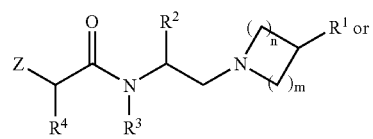

Ia

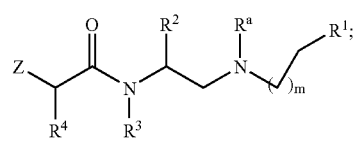

Ib or a stereoisomer, prodrug, pharmaceutically acceptable salt, hydrate, solvate, acid salt hydrate, N-oxide or isomorphic crystalline form thereof.

In formula Ia or Ib, m is the integer 1, 2, or 3, preferably, m is 1. In formula Ia, n is the integer 1, 2, or 3. In formula Ia, the quantity (m+n) is an integer in the range of 2 to 5, preferably, the quantity (m+n) is 3.

In formula Ia or Ib, o is the integer 0, 1, 2, or 3. In certain preferred embodiments, o is the integer 0 or 1.

In formula Ia or Ib, p is the integer 0 or 1. In some other preferred embodiments, p is 0. In certain other preferred embodiments, p is 1.

In formula Ia or Ib, $R^1$ is H or OH. In preferred embodiments, $R^1$ is —OH.

In formula Ib, $R^a$ is alkyl.

In formula Ia or Ib, $R^2$ is alkyl, aryl, or aralkyl, preferably, alkyl, or aryl. In preferred embodiments, $R^2$ is alkyl, more preferably, prop-2-yl. In other preferred embodiments, $R^2$ is aryl, more preferably, phenyl.

In formula Ia or Ib, $R^3$ is alkyl, or $R^2$ and $R^3$ taken together with the atoms through which they are connected form a 4- to 8-membered heterocyclic ring. In certain preferred embodiments, $R^3$ is alkyl, more preferably, methyl. In other preferred embodiments, $R^2$ and $R^3$ taken together with the atoms through which they are connected form a 4- to 8-membered heterocyclic ring, more preferably, a 5- to 6-membered heterocyclic ring.

In formula Ia or Ib, $R^4$ is H, alkyl, cycloalkyl, alkylcycloalkyl, aryl, aralkyl, heteroaryl, heteroarylalkyl. In preferred embodiments, $R^4$ is H.

In formula Ia or Ib, Z is —$NR^5R^6$ or —$(CH_2)_o$—C(=O)$NR^7R^8$.

In Z, $R^5$ is H, alkyl or aryl. In some preferred embodiments, $R^5$ is H, methyl or phenyl. In more preferred embodiments, $R^5$ is H. In other more preferred embodiments, $R^5$ is methyl. In yet other more preferred embodiments, $R^5$ is phenyl.

In Z, $R^6$ is aryl, alkaryl, —CO(NH)$_p$R$^9$, or —SO$_2$R$^9$, provided that at least one of $R^5$ and $R^6$ is other than aryl. Preferably, $R^6$ is aryl, alkaryl, or —CO(NH)$_p$R$^9$. In some preferred embodiments, $R^6$ is aryl, more preferably, phenyl. In some more preferred embodiments, $R^6$ is aryl, preferably phenyl, substituted with —CN, —NO$_2$, —NHS(=O)$_2$ (alkyl), halo, or —CF$_3$. In some particularly preferred embodiments, $R^6$ is phenyl substituted with halo, particularly chloro. In some other preferred embodiments, $R^6$ is alkaryl.

In Z, $R^7$ is H or alkyl. In preferred embodiments, $R^7$ is H.

In Z, $R^8$ is alkyl, aryl, aralkyl, alkaryl, heteroaryl, heteroarylalkyl, cycloalkyl, or cycloalkylalkyl. Preferably, $R^8$ is aryl, aralkyl, alkaryl, or heteroaryl.

In Z, $R^9$ is alkyl, cycloalkyl, alkylcycloalkyl, aryl, aralkyl, heteroaryl, or heteroarylalkyl. In certain preferred embodiments, $R^9$ is alkyl. In other preferred embodiments, $R^9$ is aryl. In some more preferred embodiments, when $R^9$ is aryl, p is 1. Even more preferably, when p is 1, the aryl is phenyl.

In preferred embodiments, the invention provides compounds of formula IIa or IIb:

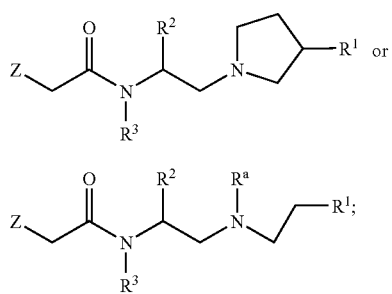

wherein the substituents are defined as above.

In other preferred embodiments of compounds of formula IIa or IIb, the compounds have formula IIc or IId:

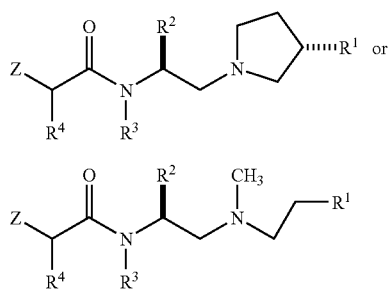

wherein the substituents are defined as above.

In preferred embodiments of compounds of formula IIc or IId,
$R^1$ is H or OH;
$R^2$ is aryl or alkyl;
$R^3$ is alkyl;
$R^4$ is H;
Z is —NR$^5$R$^6$ or —(CH$_2$)$_o$—C(=O)NR$^7$R$^8$;
$R^5$ is H, alkyl, or aryl;
$R^7$ is H;
$R^8$ is aryl, aralkyl, heteroaryl, or alkaryl; and
o is the integer 0 or 1.

In certain more preferred embodiments of compounds of formula IIc or IId, wherein the substituents are as defined above, $R^6$ is aryl, alkaryl or —CO(NH)$_p$R$^9$.

In certain preferred embodiments, the invention provides compounds of formula III:

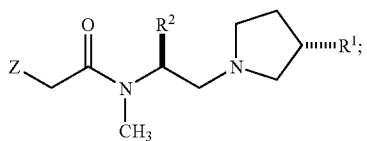

wherein the substituents are defined as above.

In preferred embodiments of formula III,
$R^1$ is OH;
$R^2$ is phenyl or prop-2-yl;
$R^5$ is H, methyl, or phenyl; and
$R^9$ is alkyl.

In certain preferred embodiments of formula III, $R^2$ is phenyl, where unsubstituted phenyl is particularly preferred.

In certain preferred embodiments of formula III, $R^5$ is H.

In certain preferred embodiments of formula III, $R^6$ is phenyl or meta-methylphenyl.

In certain preferred embodiments of formula III, $R^8$ is phenyl or heteroaryl, where unsubstituted phenyl is particularly preferred.

In certain preferred embodiments of formula III, $R^9$ is methyl or n-propyl.

In certain preferred embodiments of formula III, Z is —NH(phenyl). In certain even more preferred embodiments of formula III, Z is —NH(unsubstituted phenyl). In certain other more preferred embodiments of formula III, Z is —NH(substituted phenyl), where the phenyl of the Z moiety is substituted with —NHS(=O)$_2$—R$^9$.

In some other preferred embodiments of formula III, o is 0. In some more preferred embodiments of formula III, Z is —C(=O)NH(unsubstituted phenyl).

In some other preferred embodiments of formula III, o is 1. In some more preferred embodiments of formula III, Z is —CH$_2$C(=O)NH(unsubstituted phenyl).

In yet another preferred embodiment, the compound has the formula IV:

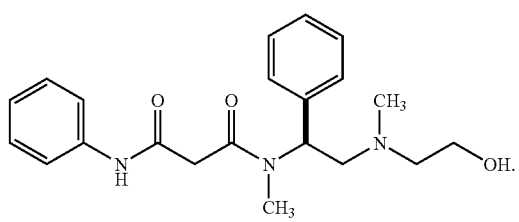

Preferred compounds of the invention include:
N-{2-[(S)-3-hydroxy-pyrrolidin-1-yl]-(S)-1-phenyl-ethyl}-N-methyl-2-phenylamino-acetamide;
N-{2-[(S)-3-hydroxy-pyrrolidin-1-yl]-(S)-1-phenyl-ethyl}-N-methyl-2-(methyl-phenyl-amino)-acetamide;
2-(acetyl-phenyl-amino)-N-{2-[(S)-3-hydroxy-pyrrolidin-1-yl]-(S)-1-phenyl-ethyl]-(S)-1-phenyl-ethyl}-N-methyl-acetamide;

2-(4-cyano-phenylamino)-N-{2-[(S)-3-hydroxy-pyrrolidin-1-yl]-(S)-1-phenyl-ethyl}-N-methyl-acetamide;
2-(3-cyano-phenylamino)-N-{2-[(S)-3-hydroxy-pyrrolidin-1-yl]-(S)-1-phenyl-ethyl}-N-methyl-acetamide;
2-(2-cyano-phenylamino)-N-{2-[(S)-3-hydroxy-pyrrolidin-1-yl]-(S)-1-phenyl-ethyl}-N-methyl-acetamide;
2-(4-aminomethyl-phenylamino)-N-{2-[(S)-3-hydroxy-pyrrolidin-1-yl]-(S)-1-phenyl-ethyl}-N-methyl-acetamide;
2-[(4-cyano-phenyl)-methyl-amino]-N-{2-[(S)-3-hydroxy-pyrrolidin-1-yl]-(S)-1-phenyl-ethyl}-N-methyl-acetamide;
N-{2-[(S)-3-hydroxy-pyrrolidin-1-yl]-(S)-1-phenyl-ethyl}-2-[4-(methanesulfonylamino-methyl)-phenylamino]-N-methyl-acetamide;
N-{2-[(S)-3-hydroxy-pyrrolidin-1-yl]-(S)-1-phenyl-ethyl}-2-[3-(methanesulfonylamino-methyl)-phenylamino]-N-methyl-acetamide;
N-{2-[(S)-3-hydroxy-pyrrolidin-1-yl]-(S)-1-phenyl-ethyl}-2-[2-(methanesulfonylamino-methyl)-phenylamino]-N-methyl-acetamide;
2-(3,4-dichloro-phenylamino)-N-{2-[(S)-3-hydroxy-pyrrolidin-1-yl]-(S)-1-phenyl-ethyl}-N-methyl-acetamide;
2-(4-trifluoromethyl-phenylamino)-N-{2-[(S)-3-hydroxy-pyrrolidin-1-yl]-(S)-1-phenyl-ethyl}-N-methyl-acetamide;
2-[(2,4-dichloro-phenyl)-methanesulfonyl-amino]-N-{2-[(S)-3-hydroxy-pyrrolidin-1-yl]-(S)-1-phenyl-ethyl}-N-methyl-acetamide;
2-(4-nitro-phenylamino)-N-{2-[(S)-3-hydroxy-pyrrolidin-1-yl]-(S)-1-phenyl-ethyl}-N-methyl-acetamide;
N-{2-[(S)-3-hydroxy-pyrrolidin-1-yl]-(S)-1-phenyl-ethyl}-2-(4-methanesulfonylamino-phenylamino)-N-methyl-acetamide;
N-{2-[(S)-3-hydroxy-pyrrolidin-1-yl]-(S)-1-phenyl-ethyl}-2-(4-propanesulfonylamino-phenylamino)-N-methyl-acetamide;
N-{(S)-1-[(S)-3-hydroxy-pyrrolidin-1-ylmethyl]-2-methyl-propyl}-N-methyl-2-[4-(propane-1-sulfonylamino)-phenylamino]-acetamide;
propane-1-sulfonic acid (4-{2-[2-(S)-{(S)-3-hydroxy-pyrrolidin-1-ylmethyl}-piperidin-1-yl]-2-oxo-ethylamino}-phenyl)-amide;
N-{2-[(S)-3-hydroxy-pyrrolidin-1-yl]-(S)-1-phenyl-ethyl}-N-methyl-N'-phenyl-malonamide;
N-{2-[(2-hydroxy-ethyl)-methyl-amino]-(S)-1-phenyl-ethyl}-N-methyl-N'-phenyl-malonamide;
N-[4-(methanesulfonylamino-methyl)-phenyl]-N'-{2-[(S)-3-hydroxy-pyrrolidin-1-yl]-(S)-1-phenyl-ethyl}-N'-methyl-malonamide;
N-[4-(ethanesulfonylamino-methyl)-phenyl]-N'-{2-[(S)-3-hydroxy-pyrrolidin-1-yl]-(S)-1-phenyl-ethyl}-N'-methyl-malonamide;
N-{2-[(S)-3-hydroxy-pyrrolidin-1-yl]-(S)-1-phenyl-ethyl}-N'-(4-methanesulfonylamino-phenyl)-N-methyl-malonamide;
N-{2-[(S)-3-hydroxy-pyrrolidin-1-yl]-(S)-1-phenyl-ethyl}-N-methyl-N'-[2-(pyrrolidine-1-sulfonyl)-phenyl]-malonamide;
N-benzyl-N'-{2-[(S)-3-hydroxy-pyrrolidin-1-yl]-(S)-1-phenyl-ethyl}-N'-methyl-malonamide;
N-{2-[(S)-3-hydroxy-pyrrolidin-1-yl]-(S)-1-phenyl-ethyl}-N-methyl-N'-thiazol-2-yl-malonamide;
N-{2-[(S)-3-hydroxy-pyrrolidin-1-yl]-(S)-1-phenyl-ethyl}-N-methyl-N'-pyridin-3-yl-malonamide;
N-{2-[(S)-3-hydroxy-pyrrolidin-1-yl]-(S)-1-phenyl-ethyl}-N-methyl-N'-phenyl-succinimide;
N-[(S)-1-{(S)-3-hydroxy-pyrrolidin-1-ylmethyl}-2-methyl-propyl]-N-methyl-N'-phenyl-succinamide;
4-{(S)-2-[(S)-3-hydroxy-pyrrolidin-1-ylmethyl]-piperidin-1-yl}-4-oxo-N-phenyl-butyramide;
N-{2-[(S)-3-hydroxy-pyrrolidin-1-yl]-(S)-1-phenyl-ethyl}-N-methyl-N'-thiazol-2-yl-succinamide;
N-{2-[(S)-3-hydroxy-pyrrolidin-1-yl]-(S)-1-phenyl-ethyl}-N-methyl-N'-pyridin-3-yl-succinamide;
N-{2-[(S)-3-hydroxy-pyrrolidin-1-yl]-(S)-1-phenyl-ethyl}-N-methyl-2-(3-phenyl-ureido)-acetamide;
N-[(S)-1-{(S)-3-hydroxy-pyrrolidin-1-ylmethyl}-2-methyl-propyl]-N-methyl-2-(3-phenyl-ureido)-acetamide;
4-{(S)-2-[(S)-3-hydroxy-pyrrolidin-1-ylmethyl]-piperidin-1-yl}-4-oxo-N-phenyl-butyramide; and
a stereoisomer, a prodrug, a pharmaceutically acceptable salt, a hydrate, a solvate, an acid salt hydrate, an N-oxide, or an isomorphic crystalline form thereof.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods of the present invention may exist in prodrug form. As used herein, "prodrug" is intended to include any covalently bonded carriers which release the active parent drug, for example, as according to formula Ia or Ib or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula Ia or Ib, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

Compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The κ agonist compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain ameliorization, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of formula Ia or Ib may be co-administered with at least one opioid. Suitable opioids include alfentanil, buprenorphine, butoiphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

The compounds of the invention may also be formulated with other optional active ingredients, in addition to the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics, and mixtures thereof. Such additional ingredients include any of the following:

a. Antibacterial Agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmitate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba(dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin 0, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin .beta.-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-.beta., Chloramine-T, Dichloramine-T, Formosulfathiazole, N.sup.2-Formyl-sulfisomidine, N.sup.4-.beta.-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, N.sup.4-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipiveftin and Pilocarpine.

f. Anti-Inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromom-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline;

Others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

In certain embodiments, amide compounds of the present invention, and particularly amide compounds of formulae (IIa), (IIb), and (III), have been characterized in opioid receptor binding assays and show preferential binding to κ opioid receptors relative to µ and δ opioid receptors. In certain embodiments, the invention is directed to methods of binding opioid receptors, including κ opioid receptors, in a patient in need thereof, comprising the step of administering to the patient an effective amount of a compound of formula I. In certain preferred embodiments, the invention is directed to methods of binding κ opioid receptors, wherein said κ opioid receptors are located in the central nervous system. In other preferred embodiments, the invention is directed to methods of binding κ opioid receptors, wherein said κ opioid receptors are located peripherally to the central nervous system. In yet further preferred embodiments, the invention is directed to methods of binding opioid receptors, wherein said binding agonizes the activity of said opioid receptors. In other preferred embodiments, the invention is directed to methods of binding opioid receptors, wherein the compound of formula Ia or Ib does not substantially cross the blood-brain barrier.

In yet another embodiment, the invention is directed to methods for preventing or treating gastrointestinal dysfunction comprising the step of administering to a patient in need thereof, an effective amount of a compound of formula Ia or Ib.

In other embodiments, the invention is directed to methods for preventing or treating ileus comprising the step of administering to a patient in need thereof, an effective amount of a compound of formula Ia or Ib.

In another embodiment, the invention is directed to methods for preventing or treating pain comprising the step of administering to a patient in need thereof, an effective amount of a compound of formula Ia or Ib. In preferred embodiments, the method further comprises the step of administering to said patient at least one opioid. In other preferred embodiments, the method further comprises at least one compound selected from the group consisting of antibiotics, antivirals, antifungals, anti-inflammatories, anesthetics, and mixtures thereof, as described herein above.

Suitable opioids include, but are not limited to, alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, and mixtures thereof.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, an effective amount of a compound of formula Ia or Ib.

In another embodiment, the invention is directed to methods for preventing or treating cerebral edema, comprising the step of administering to a patient in need thereof, an effective amount of a compound of formula Ia or Ib.

In other embodiments, the invention is directed to methods for preventing or treating oxygen supply deficiency of the central nervous system, comprising the step of administering to a patient in need thereof, an effective amount of a compound of formula Ia or Ib.

In another embodiment, the invention is directed to methods for inducing diuresis, comprising the step of administering to a patient in need thereof, an effective amount of a compound of formula Ia or Ib.

In yet another embodiment, the invention is directed to methods for preventing or treating tussis, comprising the step of administering to a patient in need thereof, an effective amount of a compound of formula Ia or Ib.

The amide derivatives of the present invention may be prepared according to the general methods depicted in Schemes 1 to 15. The target molecules include 4 structural classes: phenylamino-acetamide, N-substituted-malonamic acid amide, N-substituted-succinamic acid amide and (3-phenyl-ureido)-acetic acid amide. The syntheses of these compounds were conducted by using the various synthetic methods generally described below.

The syntheses of the phenylamino-acetamide derivatives 1 through 19, are summarized in Scheme 1 through Scheme 6. Direct coupling of N-phenyl-glycine with 1-(2-methylamino-(S)-2-phenyl-ethyl)-pyrrolidin-(S)-3-ol using TBTU as the acylating agent gave 1. The N-phenyl-glycine was converted to the methyl ester, which was reacted with methyl iodide or acetyl chloride using potassium carbonate as a base, to yield the N-methylated and N-acylated products respectively. Hydrolysis of the esters with hydrochloric acid or lithium hydroxide afforded the acids, which were coupled with 1-(2-methylamino-(S)-2-phenyl-ethyl)-pyrrolidin-(S)-3-ol in the presence of TBTU, furnishing 2 and 3 (Scheme 1).

Scheme 1

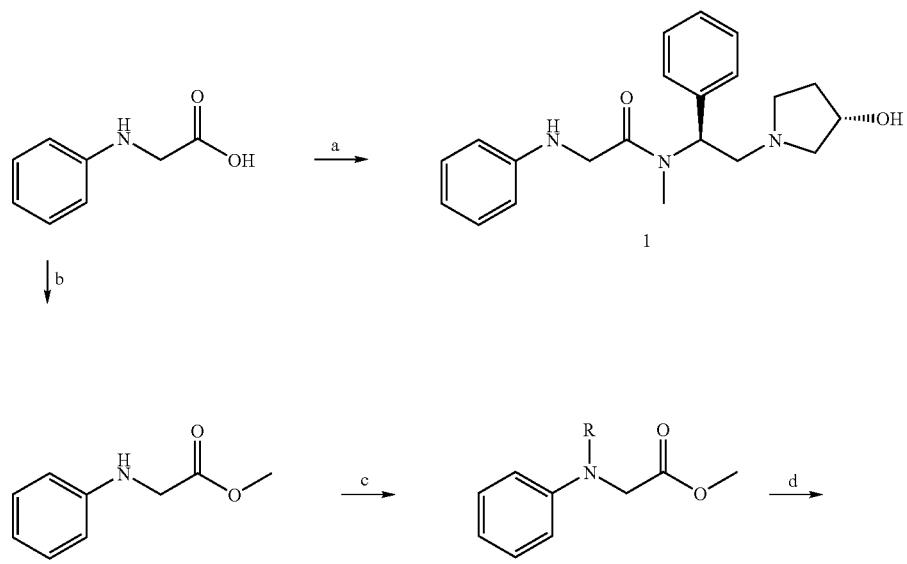

-continued

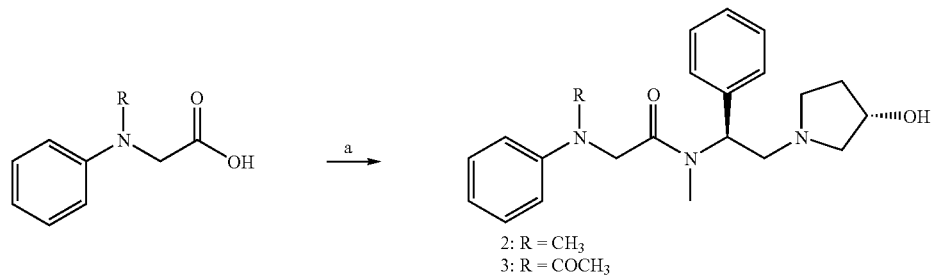

2: R = CH₃
3: R = COCH₃ a) 2-[(S)-3-hydroxy-pyrrolidin-1-yl]-(S)-1-phenyl-ethyl-methyl-amine dihydrochloride, TBTU, i-Pr₂NEt, MeCN;
b) MeOH, HCl;
c) MeI or CH₃COCl, K₂CO₃, MeCN;
d) 10% HCl or LiOH, MeOH-THF-H₂O Scheme 2 outlines the synthesis of 4, 5, 6, 7, and 8. Commercially available para-, meta- and ortho-cyanoanilines were reacted with chloroacetic acid to give the corresponding para-, meta-, and ortho-cyanophenylacetic acids, which were coupled with 1-(2-methylamino-(S)-2-phenyl-ethyl)-pyrrolidin-(S)-3-ol in the presence of TBTU, to yield 4, 5 and 6 respectively. Hydrogenation of compound 4 gave compound 7. Treatment of 4-cyanophenylacetic acid with methyl iodide using potassium hydroxide as a base gave the N-methylated ester. Hydrolysis of the ester with lithium hydroxide afforded the acid, which was coupled with 1-(2-methylamino-(S)-2-phenyl-ethyl)-pyrrolidin-(S)-3-ol to yield 8.

Scheme 2

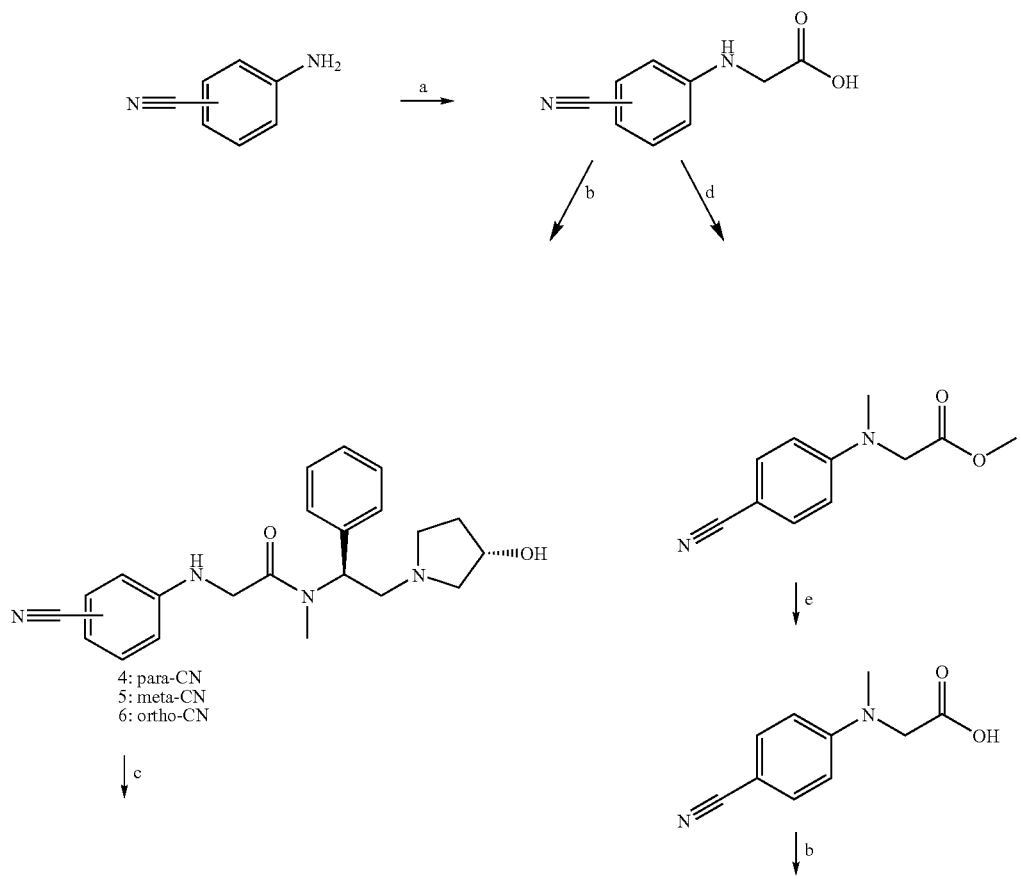

4: para-CN
5: meta-CN
6: ortho-CN

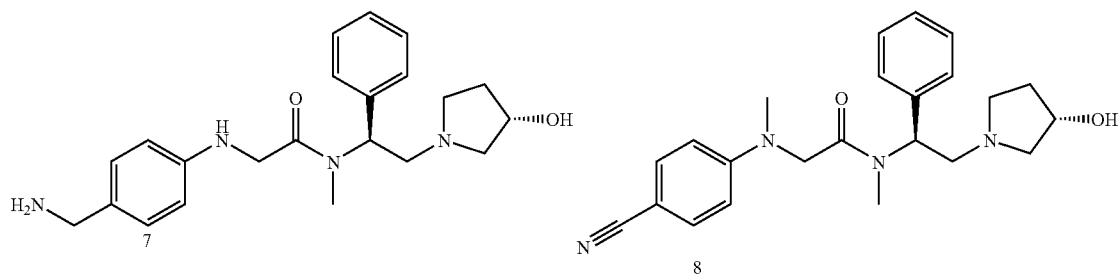

a) ClCH₂COOH, H₂O;
b) 2-[(S)-3-hydroxy-pyrrolidin-1-yl]-(S)-1-phenyl-ethyl-methyl-amine dihydrochloride, TBTU, i-PrN₂Et, MeCN;
c) H₂, Pd/C, MeOH, HCl;
d) MeI, KOH, DMSO;
e) LiOH, MeOH-THF-H₂O Scheme 3 describes the synthesis of 9, 10, and 11. Hydrogenation of the para-, meta- and ortho-cyanophenylacetic acids (Scheme 2) gave the corresponding benzyl amine derivatives. The acids were converted to the methyl esters under standard conditions, and reacted with methanesulfonyl chloride to give the sulfonamides. Hydrolysis of the esters with lithium hydroxide afforded the corresponding para-, meta-, and ortho-substituted phenylacetic acids, which were each coupled with 1-(2-methylamino-(S)-2-phenyl-ethyl)-pyrrolidin-(S)-3-ol to yield 9, 10, and 11, respectively.

Scheme 3

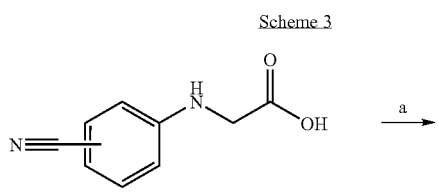

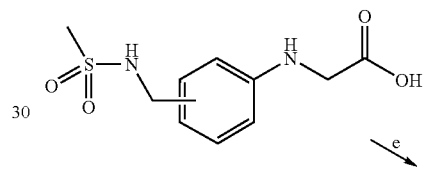

-continued

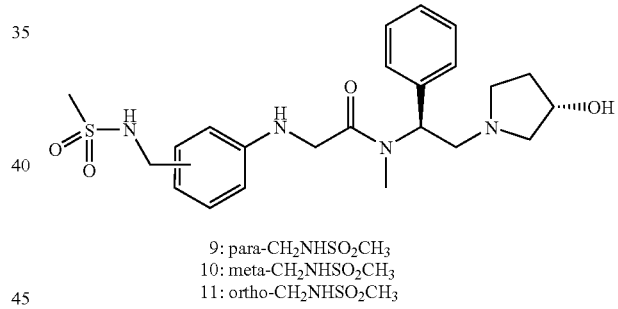

9: para-CH₂NHSO₂CH₃
10: meta-CH₂NHSO₂CH₃
11: ortho-CH₂NHSO₂CH₃ a) H₂, Pd/C, MeOH, HCl;
b) MeOH, HCl;
c) MeSO₂Cl, Et₃N, CH₂Cl₂;
d) LiOH, MeOH-THF-H₂O;
e) 2-[(S)-3-hydroxy-pyrrolidin-1-yl]-(S)-1-phenyl-ethyl-methyl-amine dihydrochloride, TBTU, i-Pr2NEt, MeCN The synthesis of 12, 13, and 14 is summarized in Scheme 4. Commercially available 3,4-dichlorophenylaminoacetic acid ethyl ester and 4-trifluoromethylphenylaminoacetic acid ethyl ester were hydrolyzed with hydrochloric acid or lithium hydroxide to give the corresponding acids, which were coupled with 1-(2-methylamino-(S)-2-phenyl-ethyl)-pyrrolidin-(S)-3-ol to afford 12 and 13 respectively. Direct coupling of the commercially available [(2,4-dichloro-phenyl)-methanesulfonyl-amino]-acetic acid with 2-[(S)-3-hydroxy-pyrrolidin-1-yl]-(S)-1-phenyl-ethyl-methyl-amine yielded 14.

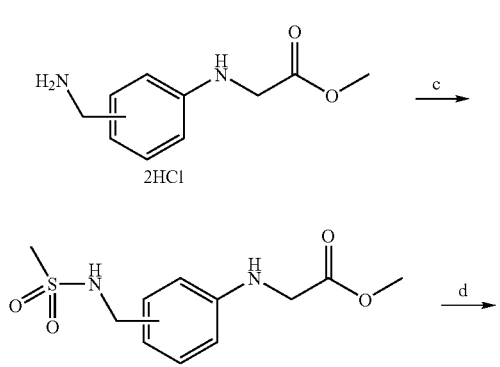

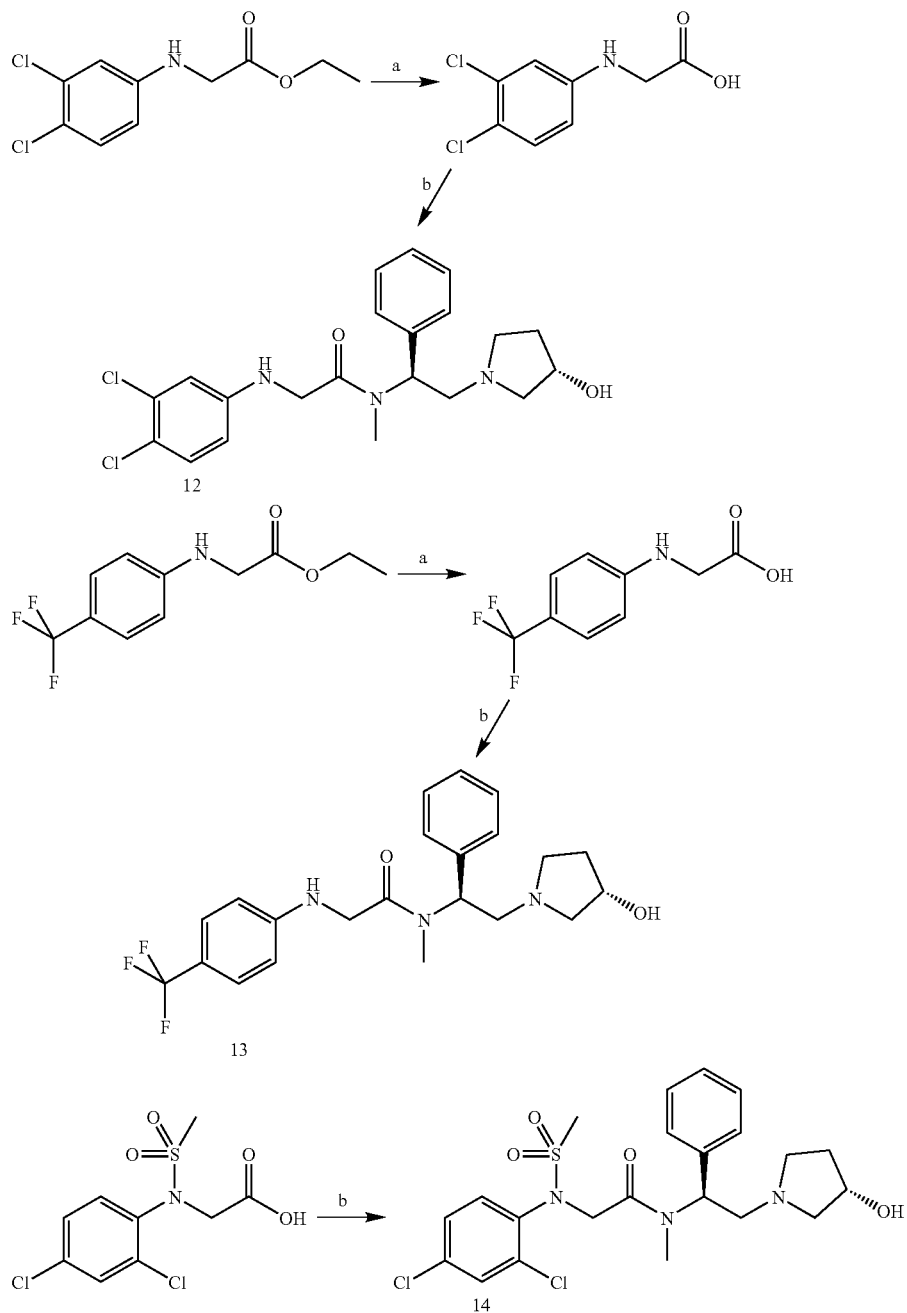

a) 10% HCl or LiOH, MeOH-THF-H₂O;
b) 2-[(S)-3-hydroxy-pyrrolidin-1-yl]-(S)-1-phenyl-ethyl-methyl-amine dihydrochloride, TBTU, i-Pr₂NEt, MeCN Scheme 5 illustrates the synthesis of 15, 16, 17, 18, and 19. Treatment of 4-nitroaniline with chloroacetic acid gave the 4-nitrophenylaminoacetic acid, which was coupled with 1-(2-methylamino-(S)-2-phenyl-ethyl)-pyrrolidin-(S)-3-ol to yield 15. 4-Nitrophenylaminoacetic acid was converted to the methyl ester under standard conditions. Protection of the amino group as trifluoroacetamide followed by reduction of the nitro group by hydrogenation, gave the aniline derivative. Reaction of the aniline with methanesulfonyl chloride and propanesulfonyl chloride furnished the disulfonylated compounds, which were treated with lithium hydroxide to yield the 4-methanesulfonylamino-phenylamino-acetic acid and 4-propanesulfonylamino-phenylamino-acetic acid respectively. Coupling of both acids with 1-(2-methylamino-(S)-2-phenyl-ethyl)-pyrrolidin-(S)-3-ol gave 16 and 17. Coupling of 4-propanesulfonylamino-phenylamino-acetic acid with 1-(3-methyl-(S)-2-methylamino-butyl)-pyrrolidin-(S)-3-ol or 1-piperidin-(S)-2-ylmethyl-pyrrolidin-(S)-3-ol afforded 18 and 19, respectively.

The synthesis of the malonamide derivatives 20 through 28 are summarized in Scheme 6 to Scheme 12. Reaction of aniline with 3-chloro-3-oxopropionate gave the malonamide, which was hydrolyzed with lithium hydroxide to give the N-phenyl-malonamic acid. Coupling of the malonamic acid with 1-(2-methylamino-(S)-2-phenyl-ethyl)-pyrrolidin-(S)-3-ol in the presence of Mukaiyama acylating reagent: 2-chloro-1-methylpyridinium iodide, yielded 20 (Scheme 6).

Compound 21 was prepared by coupling of N-phenyl-malonamic acid with 2-{Methyl-[(S)-2-methylamino-2-phenyl-ethyl]-amino}-ethanol, which was synthesized via two steps: coupling of (S)-benzyloxycarbonylamino-phenyl-acetic acid with 2-methylamino-ethanol in the presence of TBTU followed by reduction with lithium aluminum hydride (Scheme 7).

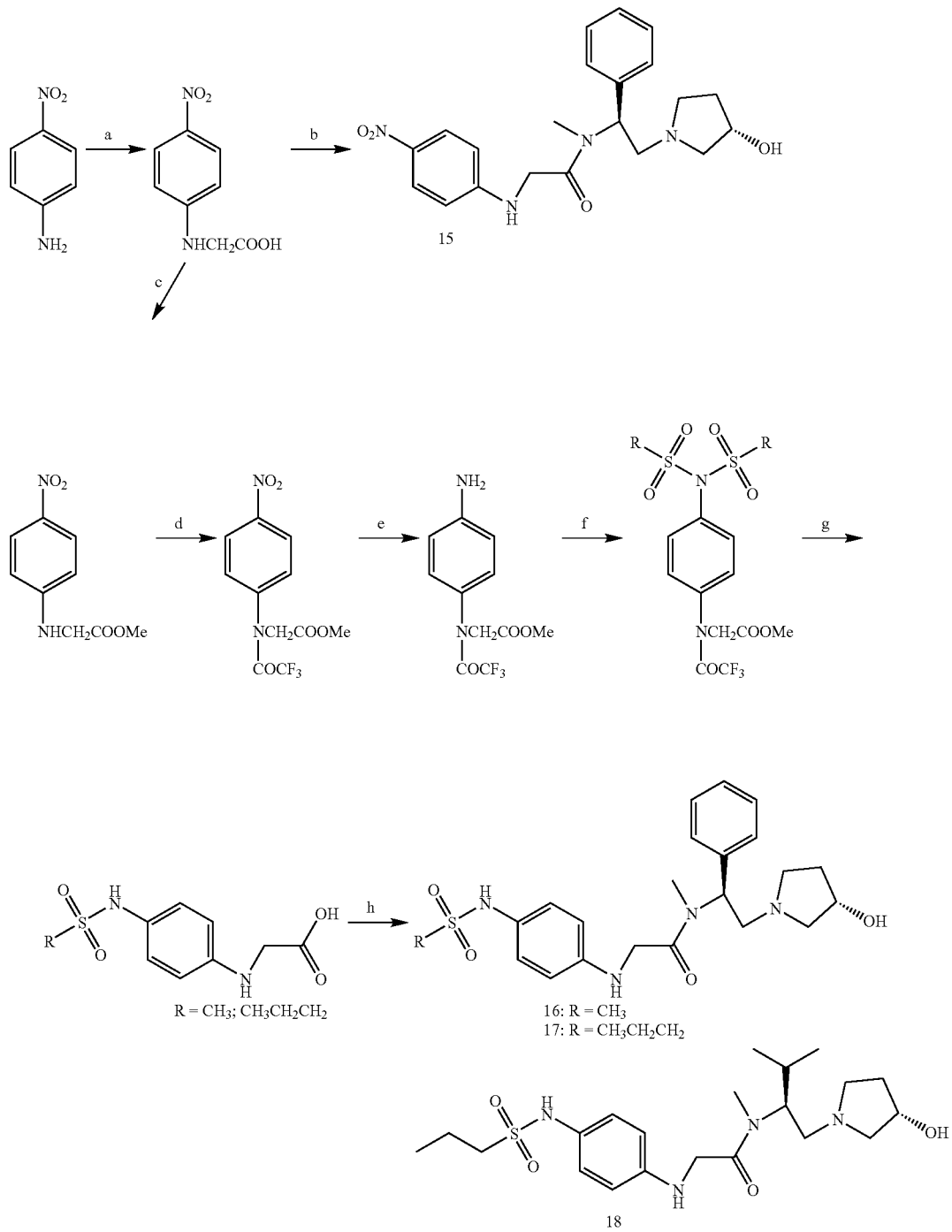

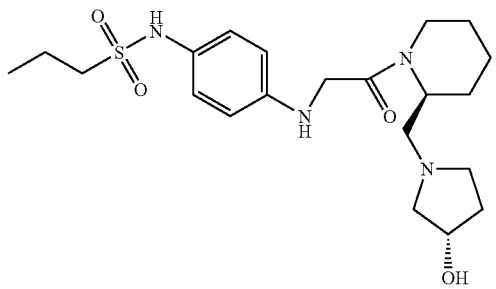

19 a) ClCH$_2$COOH;
b) 1-(2-meethylamino-(S)-2-phenyl-ethyl)-pyrrolidin-(S)-3-ol dihydrochloride, TBTU, i-Pr$_2$NEt;
c) MeOH, HCl;
d) (CF$_3$CO)$_2$O, Et$_3$N;
e) H$_2$, Pd/C;
f) MsCl or n-PrSO2Cl, Et$_3$N;
g) LiOH, MeOH-THF-H$_2$O;
h) 1-(2-methylamino-(S)-2-phenyl-ethyl)-pyrrolidin-(S)-3-ol dihydrochloride or 1-(3-Methyl-2-methylamino-butyl)-pyrrolidin-3-olor 1-Piperidin-(S)-2-ylmethyl-pyrrolidin (S)-3-ol, TBTU, i-Pr$_2$NEt.

Scheme 6

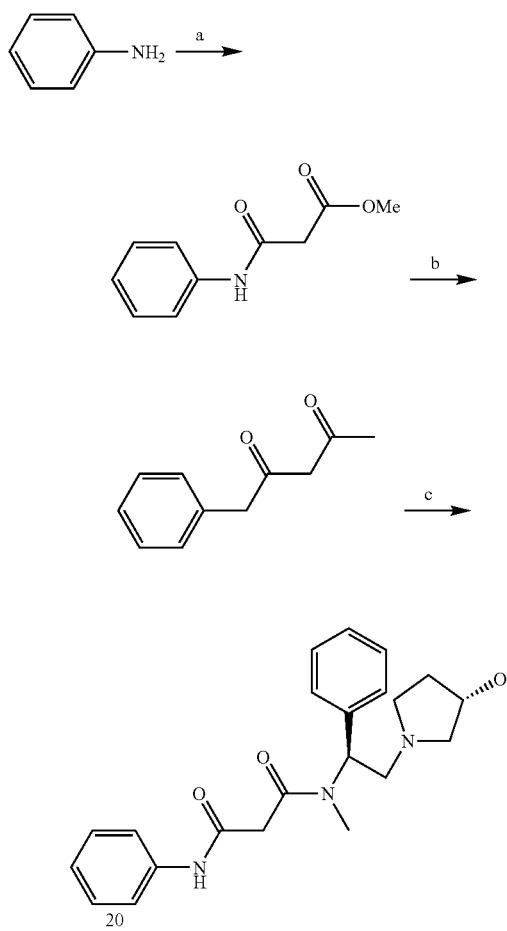

20 a) Methyl-3-chloro-3-oxopropionate, Et$_3$N;
b) LiOH, MeOH-THF-H$_2$O;
c) 1-(2-methylamino-(S)-2-phenyl-ethyl)-pyrrolidin-(S)-3-oldihydrochloride, 2-chloro-1-methylpyridinium iodide, Et$_3$N, DCM Scheme 7

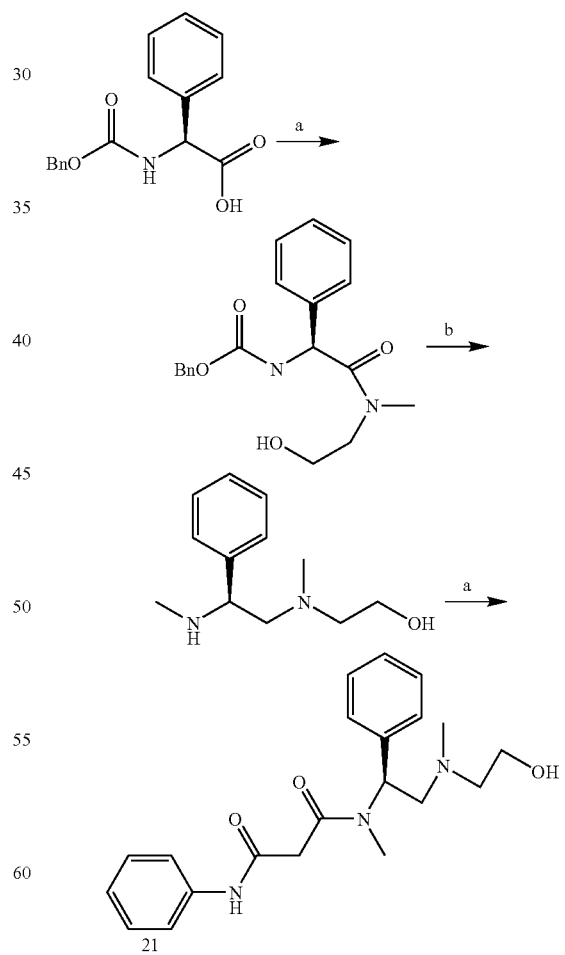

21 a) 2-(Methylamino)ethanol, TBTu, i-Pr$_2$NEt, CH$_3$CN;
b) LiAlH$_4$, THF;
c) N-Phenyl-malonamic acid, 2-chloro-1-methylpyridinium iodide, Et$_3$N, DCM.

Scheme 8 illustrates the synthesis of 22 and 23. Reaction of 4-cyanoaniline with 3-chloro-3-oxopropionate followed by hydrogenation to reduce the cyano group, gave the benzyl amine derivative. Sulfonylation of the amine with methane-sulfonyl chloride or propanesulfonyl chloride afforded the corresponding sulfonamides, which were treated with lithium hydroxide to give the acids. Coupling of the acids with 1-(2-methylamino-(S)-2-phenyl-ethyl)-pyrrolidin-(S)-3-ol in the presence of Mukaiyama acylating reagent, yielded 22 and 23.

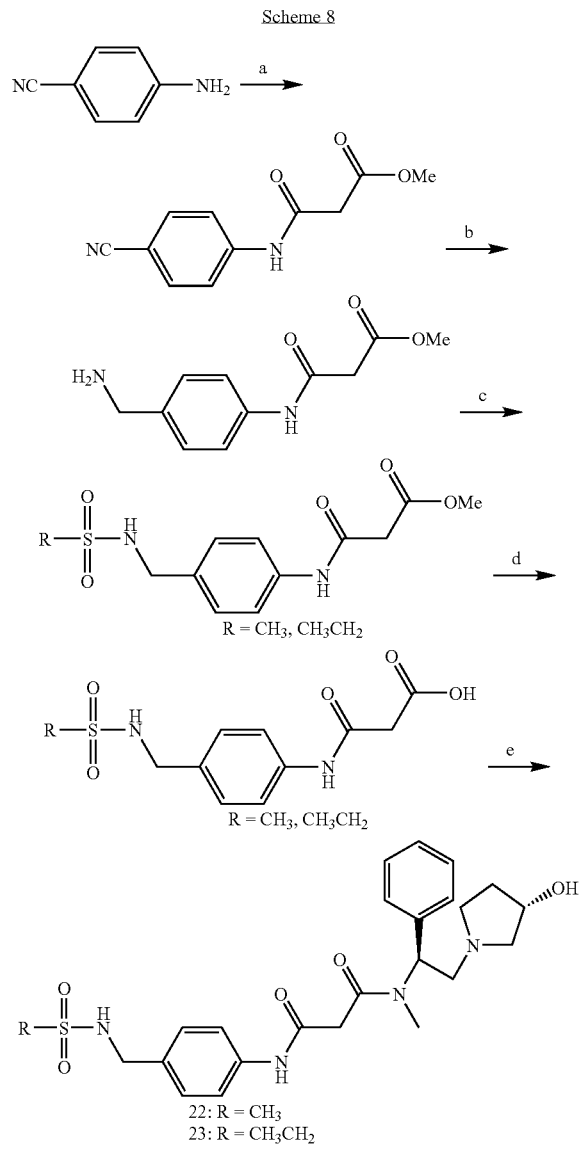

a) Methyl 3-chloro-3-oxopropionate, Et$_3$N;
b) H$_2$, Pd/C, MeOH, HCl;
c) RSO$_2$Cl (R = CH$_3$, C$_2$H$_5$), Et$_3$N;
d) LiOH, MeOH-THF-H$_2$O;
e) 1-(2-methylamino-(S)-2-phenyl-ethyl)-pyrrolidin-(S)-3-ol, dihydrochloride, 2-chloro-1-methylpyridinium iodide, DCM The synthesis of compound 24 is summarized in Scheme 9. Treatment of 4-nitroaniline with 3-chloro-3-oxopropionate followed by hydrogenation to reduce the nitro group, gave the aniline derivative. Reaction of this aniline derivative with methanesulfonyl chloride furnished the corresponding disulfonylated product, which was treated with lithium hydroxide to give the acid. Coupling of the acid with 1-(2-methylamino-(S)-2-phenyl-ethyl)-pyrrolidin-(S)-3-ol under Mukaiyama acylation condition, gave 24.

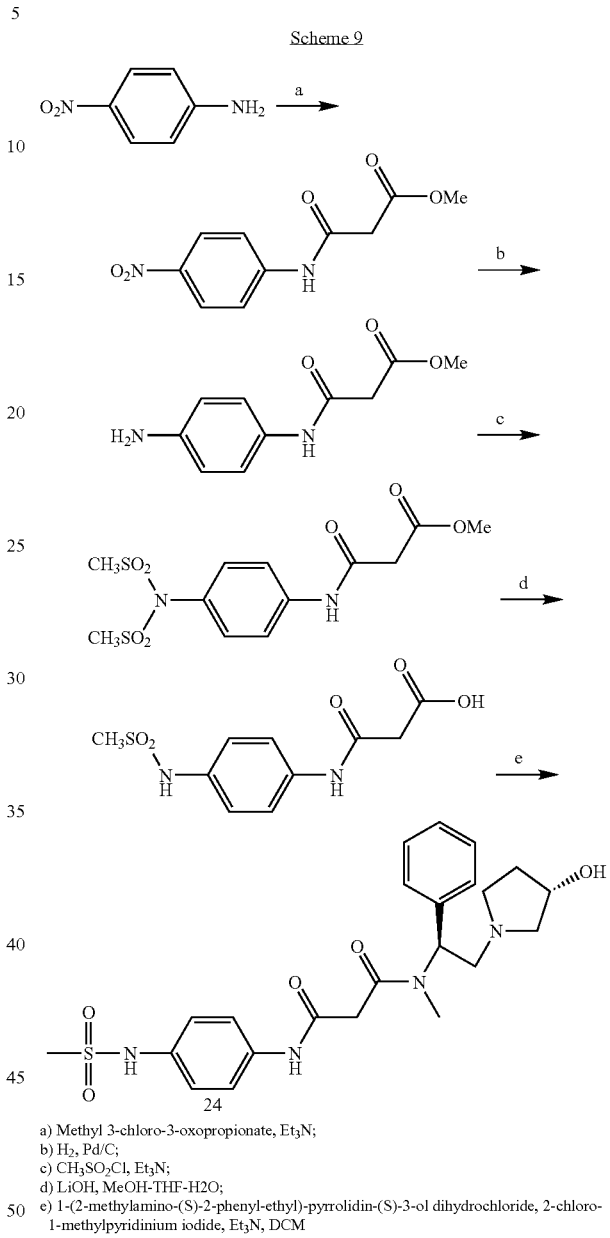

a) Methyl 3-chloro-3-oxopropionate, Et$_3$N;
b) H$_2$, Pd/C;
c) CH$_3$SO$_2$Cl, Et$_3$N;
d) LiOH, MeOH-THF-H2O;
e) 1-(2-methylamino-(S)-2-phenyl-ethyl)-pyrrolidin-(S)-3-ol dihydrochloride, 2-chloro-1-methylpyridinium iodide, Et$_3$N, DCM The synthesis of 25 (Scheme 10) was initiated by reacting 2-nitrobenzenesulfonyl chloride with pyrrolidine followed by hydrogenation which afforded the aniline derivative. Conversion of the aniline to the corresponding malonamide as described above, followed by hydrolysis with lithium hydroxide, gave the acid. Coupling of the acid with 1-(2-methylamino-(S)-2-phenyl-ethyl)-pyrrolidin-(S)-3-ol under Mukaiyama acylation condition, yielded 25.

Compound 26 was prepared by following the same reaction sequence utilized to prepare 20 except that benzyl amine replaced aniline as the starting material (Scheme 11).

Scheme 12 and 13 describe the synthesis of 27 and 28 that are analogs of 20 where the benzene ring has been replaced with a heteroaromatic ring. 2-Aminothiazole was converted to the target compound 27 (Scheme 12) by following the same reaction sequence as utilized in the preparation of 20.

Scheme 10

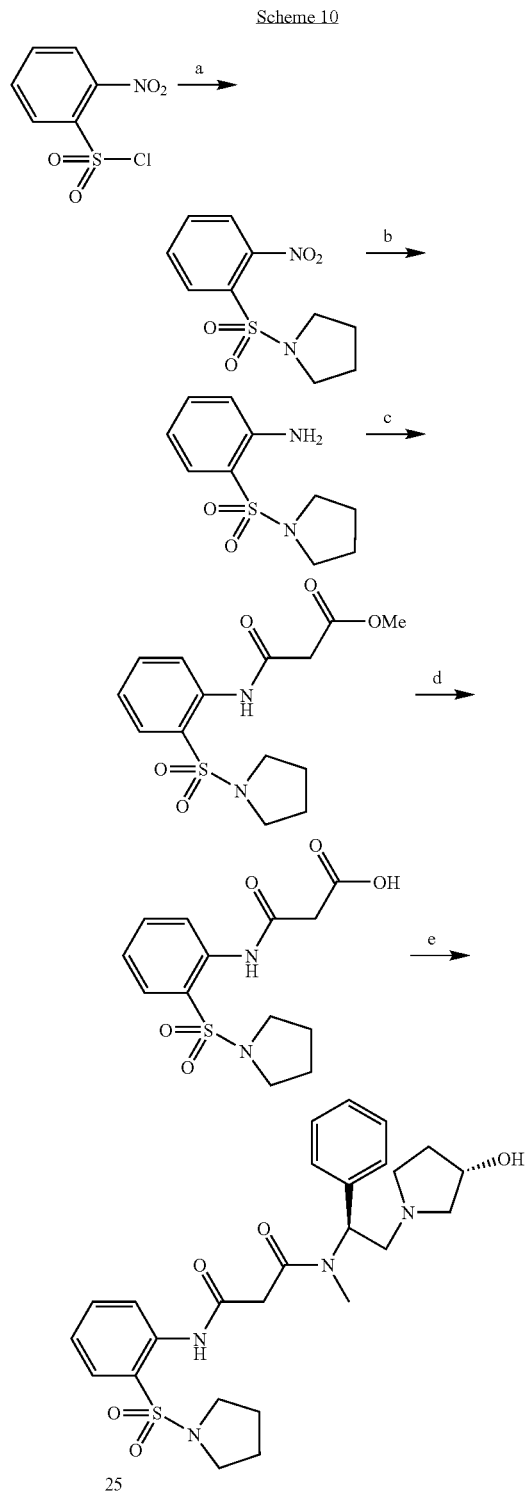

a) Pyrrolidine;
b) H₂, Pd/C;
c) Methyl 3-chlorro-3-oxopropionate, Et₃N;
d) LiOH, MeOH-THF-H₂O;
e) 1-(2-methylamino-(S)-2-phenyl-ethyl)-pyrrolidin-(S)-3-ol dihydrochloride, 2-chloro-1-methylpyridinium iodide, Et₃N, DCM Scheme 11

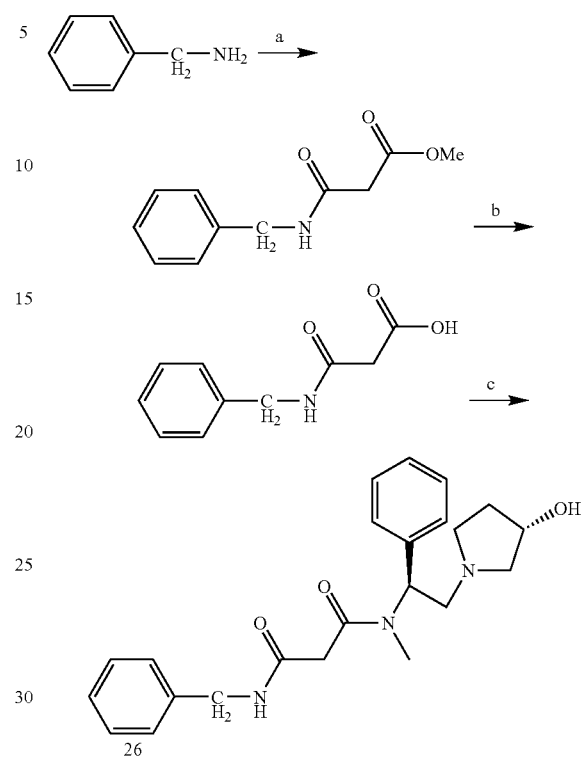

a) Methyl 3-chloro-3-oxopropionate, Et₃N;
b) LiOH, MeOH-THF-H₂O;
c) 1-(2-methylamino-(S)-2-phenyl-ethyl)-pyrrolidin-3-(S)-3-ol dihydrochloride, 2-chloro-1-methylpyridinium iodide, Et₃N, DCM Scheme 12

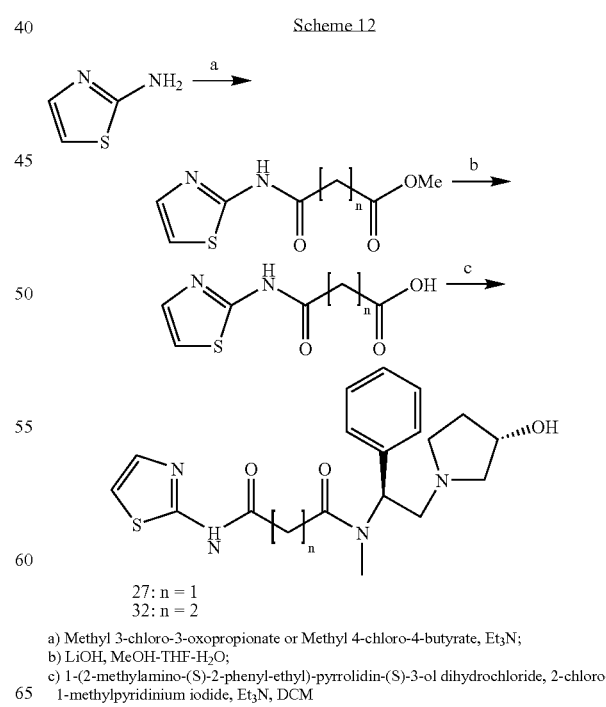

27: n = 1
32: n = 2 a) Methyl 3-chloro-3-oxopropionate or Methyl 4-chloro-4-butyrate, Et₃N;
b) LiOH, MeOH-THF-H₂O;
c) 1-(2-methylamino-(S)-2-phenyl-ethyl)-pyrrolidin-(S)-3-ol dihydrochloride, 2-chloro-1-methylpyridinium iodide, Et₃N, DCM Scheme 13

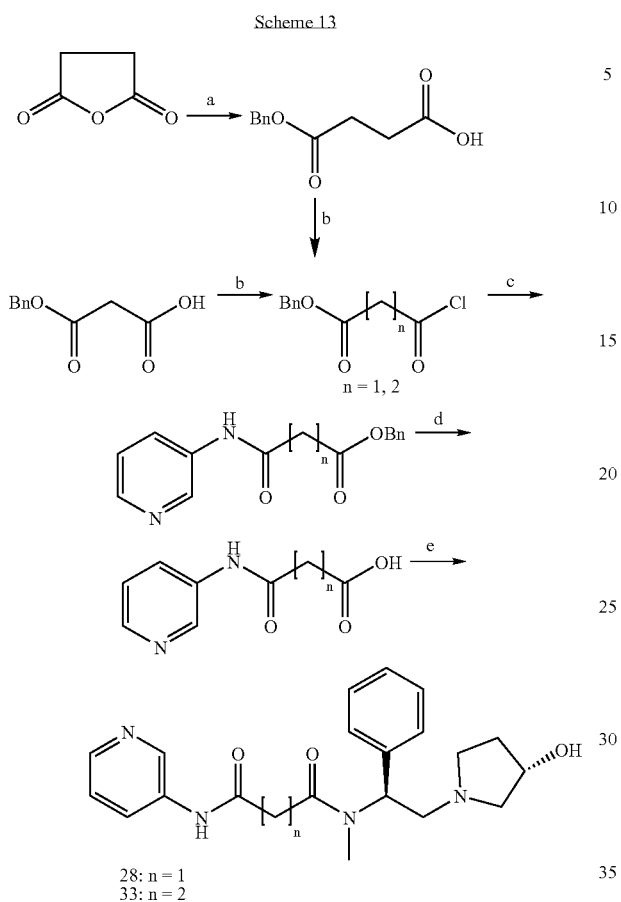

28: n = 1
33: n = 2 a) PhCH₂OH, Et₃N, DMAP;
b) (COCl)₂;
c) 3-Aminopyridine, Et₃N;
d) H₂, Pd/C;
e) 1-(2-methylamino-(S)-2-phenyl-ethyl)-pyrrolidin-(S)-3-ol dihydrochloride, 2-chloro-1-methylpyridinium iodide, Et₃N, DCM Compound 28, was synthesized using mono-benzyl malonate as the starting material (Scheme 13). Treatment of mono-benzyl malonate with oxalyl chloride gave the acyl chloride intermediate. Subsequent reaction of the resulting acyl chloride with 3-aminopyridine gave the malonamide derivative, which was hydrogenated to cleave the benzyl ester, yielding the N-pyridin-3-yl-malonamic acid. Coupling of the malonamic acid with 1-(2-methylamino-(S)-2-phenyl-ethyl)-pyrrolidin-(S)-3-ol under Mukaiyama acylation conditions yielded 28.

Scheme 14

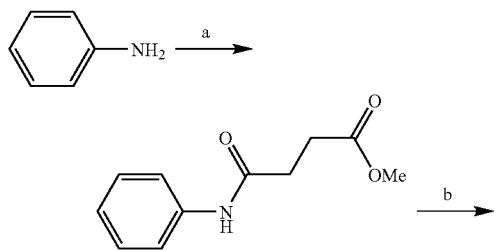

a) Methyl 4-chloro-3-oxobutyrate, Et₃N;
b) LiOH, MeOH-THF-H₂O;
c) 1-(2-methylamino-(S)-2-phenyl-ethyl)-pyrrolidin-(S)-3-ol dihydrochloride or 1-(3-methyl-(S)-2-methylamino-butyl)-pyrrolidin-(S)-3-ol or 1-piperidin-(S)-2-ylmethyl-pyrrolidin-(S)-3-ol, 2-chloro-1-methylpyridinium iodide, Et₃N, DCM The synthesis of the succinamide analogs 29, 30, 31, 32, and 33 are described in Schemes 12, 13, and 14. N-Phenyl-succinamic acid was prepared via a two step reaction sequence analogous to the preparation of the N-phenyl-malonamic acid: 1) reaction of aniline with methyl 4-chloro-3-oxobutyrate followed by 2) treatment with lithium hydroxide. Coupling of N-phenyl-succinamic acid with 1-(2-methylamino-(S)-2-phenyl-ethyl)-pyrrolidin-(S)-3-ol, 1-(3-methyl-(S)-2-methylamino-butyl)-pyrrolidin-(S)-3-ol or 1-piperidin-(S)-2-ylmethyl-pyrrolidin-(S)-3-ol afforded 29, 30 and 31, respectively.

Compound 32 was prepared by following the same reaction sequence utilized in the preparation of 27 except that methyl 4-chloro-4-butyrate replaced methyl 3-chloro-3-oxopropionate (Scheme 12). Compound 33 was prepared by following the same reaction sequence and conditions utilized in the preparation of 28 except that succinic acid monobenzyl ester replaced malonic acid monobenzyl ester as the starting material. The succinic acid monobenzyl ester was prepared by reaction of the succinic anhydride with benzyl alcohol (Scheme 13).

Scheme 15 summarizes the synthesis of urea skeleton compounds 34, 35 and 36. Reaction of the glycine methyl ester with phenyl isocyanate gave the urea derivative, which was treated with lithium hydroxide to give the (3-Phenyl-ureido)-acetic acid. Coupling of the acid with 1-(2-methy-lamino-(S)-2-phenyl-ethyl)-pyrrolidin-(S)-3-ol, 1-(3-methyl-(S)-2-methylamino-butyl)-pyrrolidin-(S)-3-ol or 1-piperidin-(S)-2-ylmethyl-pyrrolidin-(S)-3-ol gave 34, 35 or 36 respectively.

Scheme 15

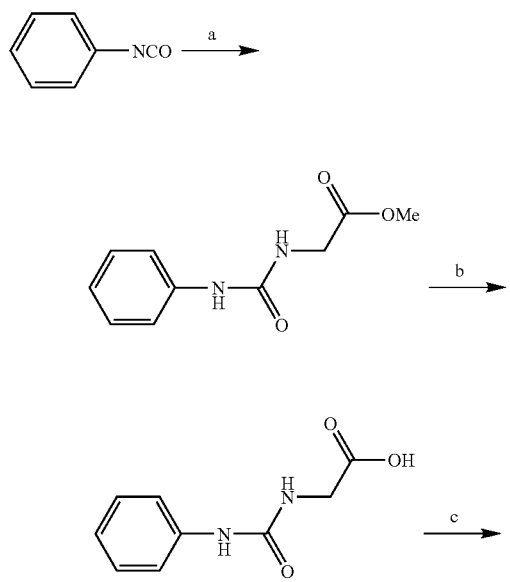

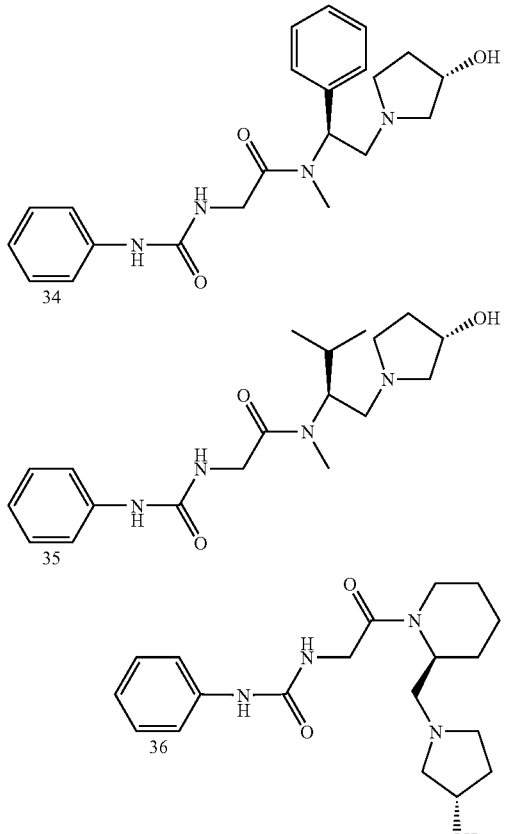

a) HCl NH$_2$CH$_2$COOMe, Et$_3$N;
b) LiOH, MeOH-THF-H$_2$O;
c) 1-(2-meethylamino-(S)-2-phenyl-ethyl)-pyrrolidin-(S)-3-ol dihydrochloride or 1-(3-methyl-(S)-2-methylamino-butyl)-pyrrolidin-(S)-3-ol or 1-piperidin-(S)-2-ylmethyl-pyrrolidin-(S)-3-ol, 2-chloro-1-methylpyridinium iodide, Et$_3$N, DCM

TABLE 1

Derivatives of Phenylamino-acetic Acid

| Example | Name | Structure | [M + 1]$^+$ |
|---|---|---|---|
| 1 | N-{2-[(S)-3-Hydroxy-pyrrolidin-1-yl]-(S)-1-phenyl-ethyl}-N-methyl-2-phenylamino-acetamide | 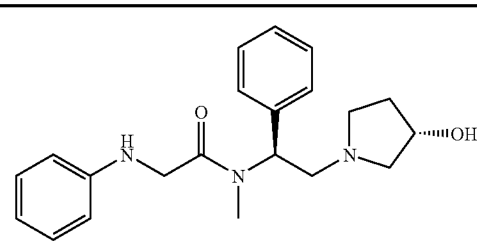 | 354 |
| 2 | N-{2-[(S)-3-Hydroxy-pyrrolidin-1-yl]-(S)-1-phenyl-ethyl}-N-methyl-2-(methyl-phenyl-amino)-acetamide | 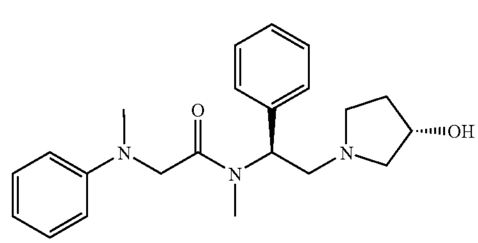 | 368 |

TABLE 1-continued

Derivatives of Phenylamino-acetic Acid

| Example | Name | Structure | [M + 1]+ |
|---|---|---|---|
| 3 | 2-(Acetyl-phenyl-amino)-N-{2-[(S)-3-hydroxy-pyrrolidin-1-yl]-(S)-1-phenyl-ethyl]-(S)-1-phenyl-ethyl}-N-methyl-acetamide | 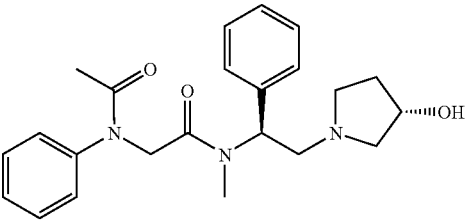 | 396 |
| 4 | 2-(4-Cyano-phenylamino)-N-{2-[(S)-3-hydroxy-pyrrolidin-1-yl]-(S)-1-phenyl-ethyl}-N-methyl-acetamide | 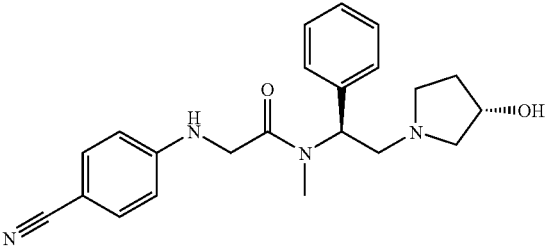 | 379 |
| 5 | 2-(3-Cyano-phenylamino)-N-{2-[(S)-3-hydroxy-pyrrolidin-1-yl]-(S)-1-phenyl-ethyl}-N-methyl-acetamide | 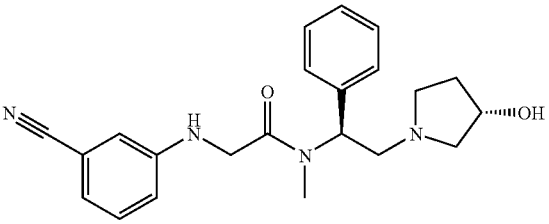 | 379 |
| 6 | 2-(2-Cyano-phenylamino)-N-{2-[(S)-3-hydroxy-pyrrolidin-1-yl]-(S)-1-phenyl-ethyl}-N-methyl-acetamide | 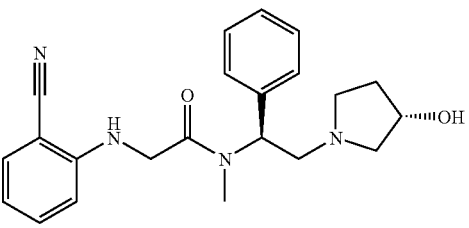 | 379 |
| 7 | 2-(4-Aminomethyl-phenylamino)-N-{2-[(S)-3-hydroxy-pyrrolidin-1-yl]-(S)-1-phenyl-ethyl}-N-methyl-acetamide | 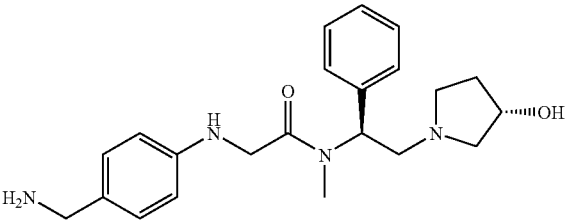 | 383 |
| 8 | 2-[(4-Cyano-phenyl)-methyl-amino]-N-{2-[(S)-3-hydroxy-pyrrolidin-1-yl]-(S)-1-phenyl-ethyl}-N-methyl-acetamide | 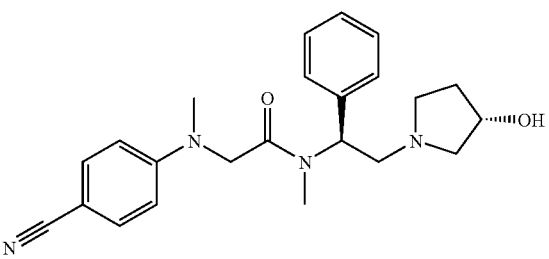 | 393 |

TABLE 1-continued

Derivatives of Phenylamino-acetic Acid

| Example | Name | Structure | [M + 1]+ |
|---|---|---|---|
| 9 | N-{2-[(S)-3-Hydroxy-pyrrolidin-1-yl]-(S)-1-phenyl-ethyl}-2-[4-(methanesulfonylamino-methyl)-phenylamino]-N-methyl-acetamide | 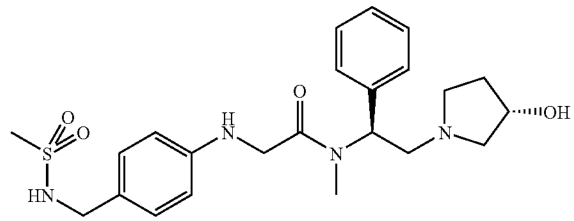 | 461 |
| 10 | N-{2-[(S)-3-Hydroxy-pyrrolidin-1-yl]-(S)-1-phenyl-ethyl}-2-[3-(methanesulfonylamino-methyl)-phenylamino[-N-methyl-acetamide | | 461 |
| 11 | N-{2-[(S)-3-Hydroxy-pyrrolidin-1-yl[-(S)-1-phenyl-ethyl}-2-[2-(methanesulfonylamino-methyl)-phenylamino]-N-methyl-acetamide | 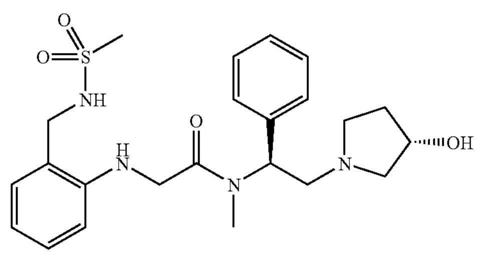 | 422 |
| 12 | 2-(3,4-Dichloro-phenylamino)-N-{2-[(S)-3-hydroxy-pyrrolidin-1-yl]-(S)-1-phenyl-ethyl}-N-methyl-acetamide | 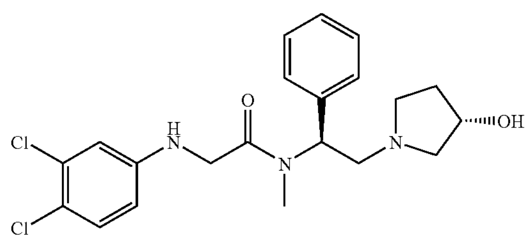 | 422 |
| 13 | 2-(4-Trifluoromethyl-phenylamino)-N-{2-[(S)-3-hydroxy-pyrrolidin-1-yl]-(S)-1-phenyl-ethyl}-N-methyl-acetamide | 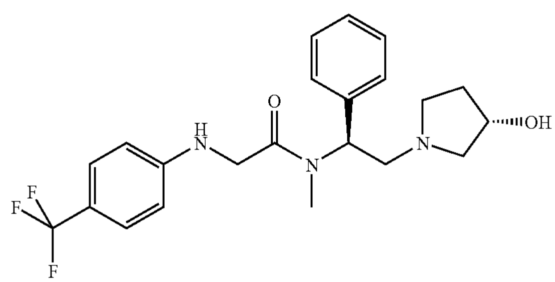 | 422 |
| 14 | 2-[(2,4-Dichloro-phenyl)-methanesulfonyl-amino]-N-{2-[(S)-3-hydroxy-pyrrolidin-1-yl]-(S)-1-phenyl-ethyl}-N-methyl-acetamide | 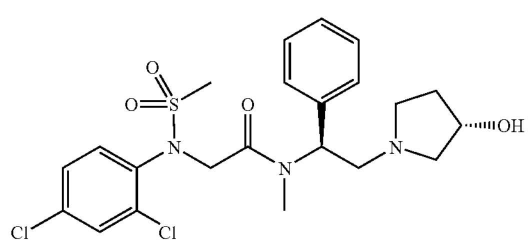 | 500 |

TABLE 1-continued

Derivatives of Phenylamino-acetic Acid

| Example | Name | Structure | [M + 1]⁺ |
|---------|------|-----------|----------|
| 15 | 2-(4-Nitro-phenylamino)-N-{2-[(S)-3-hydroxy-pyrrolidin-1-yl]-(S)-1-phenyl-ethyl}-N-methyl-acetamide | 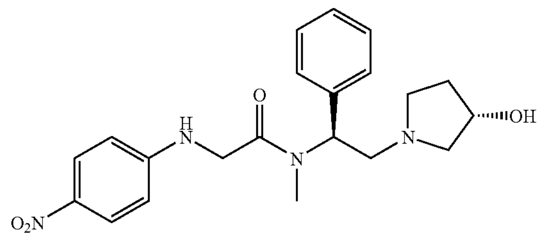 | 399 |
| 16 | N-{2-[(S)-3-Hydroxy-pyrrolidin-1-yl]-(S)-1-phenyl-ethyl}-2-(4-methanesulfonylamino-phenylamino)-N-methyl-acetamide | 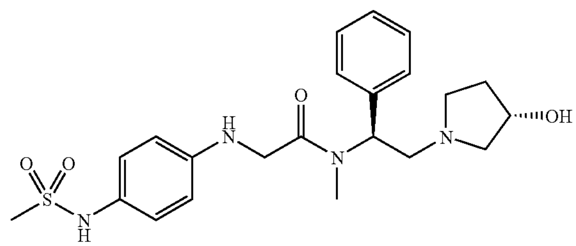 | 447 |
| 17 | N-{2-[(S)-3-Hydroxy-pyrrolidin-1-yl]-(S)-1-phenyl-ethyl}-2-(4-propanesulfonylamino-phenylamino)-N-methyl-acetamide | 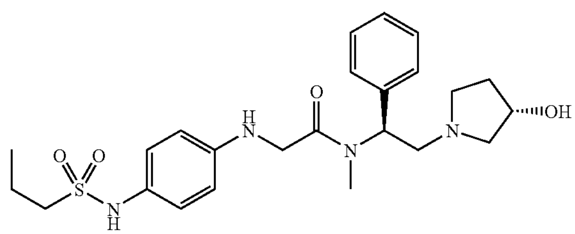 | 475 |
| 18 | N-{(S)-1-[(S)-3-Hydroxy-pyrrolidin-1-ylmethyl]-2-methyl-propyl}-N-methyl-2-[4-(propane-1-sulfonylamino)-phenylamino]-acetamide | 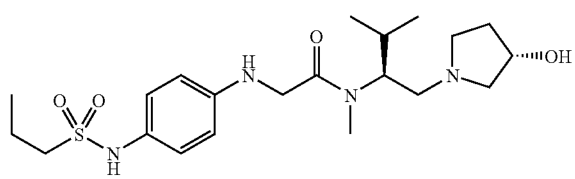 | 441 |
| 19 | Propane-1-sulfonic acid (4-{2-[2-(S)-{(S)-3-hydroxy-pyrrolidin-1-ylmethyl}-piperidin-1-yl]-2-oxo-ethylamino}-phenyl)-amide | 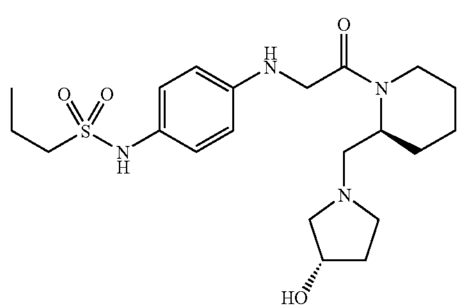 | 439 |

TABLE 2

Derivatives of N-Substituted-malonamic Acid

| Example | Name | Structure | [M + 1]+ |
|---|---|---|---|
| 20 | N-{2-[(S)-3-Hydroxy-pyrrolidin-1-yl]-(S)-1-phenyl-ethyl}-N-methyl-N'-phenyl-malonamide | 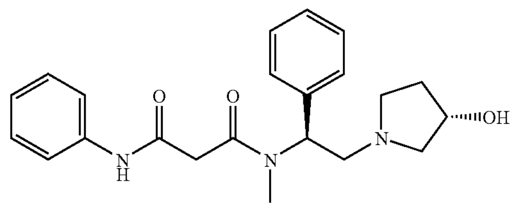 | 382 |
| 21 | N-{2-[(2-Hydroxy-ethyl)-methyl-amino]-(S)-1-phenyl-ethyl}-N-methyl-N'-phenyl-malonamide | 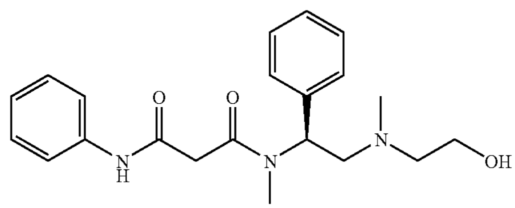 | 370 |
| 22 | N-[4-(Methanesulfonylamino-methyl)-phenyl]-N'-{2-[(S)-3-hydroxy-pyrrolidin-1-yl]-(S)-1-phenyl-ethyl}-N'-methyl-malonamide | 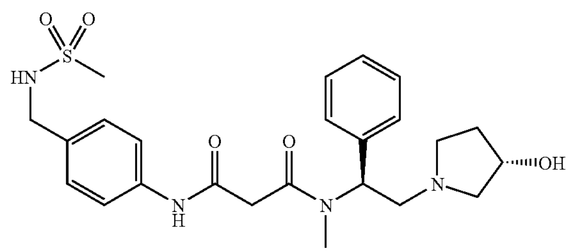 | 489 |
| 23 | N-[4-(Ethanesulfonylamino-methyl)-phenyl]-N'-{2-[(S)-3-hydroxy-pyrrolidin-1-yl]-(S)-1-phenyl-ethyl}-N'-methyl-malonamide | 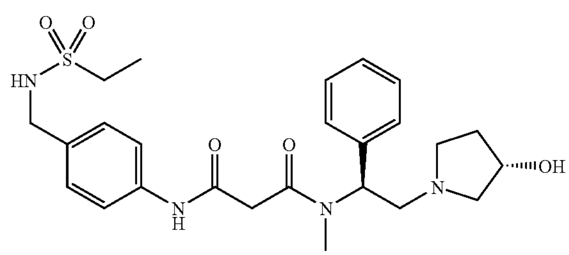 | 503 |
| 24 | N-{2-[(S)-3-Hydroxy-pyrrolidin-1-yl]-(S)-1-phenyl-ethyl}-N'-(4-methanesulfonylamino-phenyl)-N-methyl-malonamide | 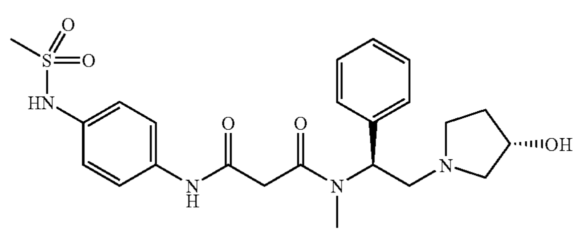 | 475 |
| 25 | N-{2-[(S)-3-Hydroxy-pyrrolidin-1-yl]-(S)-1-phenyl-ethyl}-N-methyl-N'-[2-(pyrrolidine-1-sulfonyl)-phenyl]-malonamide | 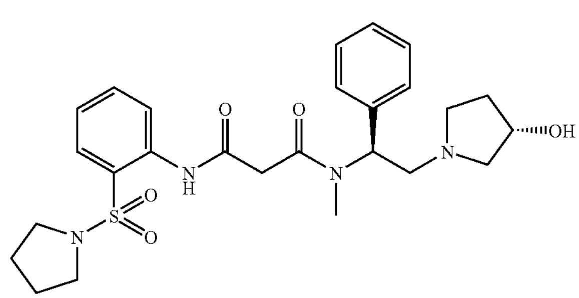 | 396 |

TABLE 2-continued

Derivatives of N-Substituted-malonamic Acid

| Example | Name | Structure | [M + 1]+ |
|---|---|---|---|
| 26 | N-Benzyl-N'-{2-[(S)-3-hydroxy-pyrrolidin-1-yl](S)-1-phenyl-ethyl}-N'-methyl-malonamide | 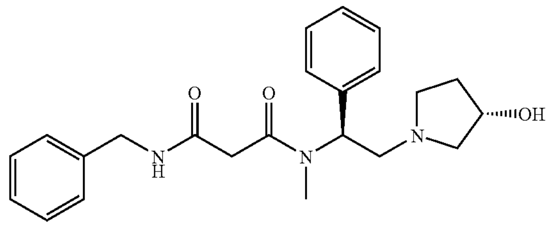 | 396 |
| 27 | N-{2-[(S)-3-Hydroxy-pyrrolidin-1-yl]-(S)-1-phenyl-ethyl}-N-methyl-N'-thiazol-2-yl-malonamide | 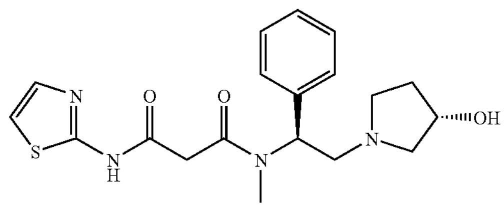 | 389 |
| 28 | N-{2-[(S)-3-Hydroxy-pyrrolidin-1-yl]-(S)-1-phenyl-ethyl}-N-methyl-N'-pyridin-3-yl-malonamide | 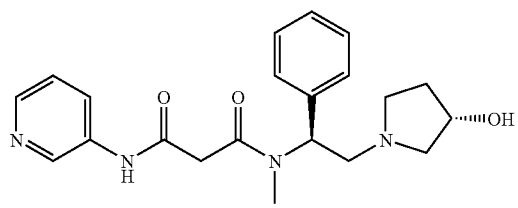 | 383 |

TABLE 3

Derivatives of N-Substituted-succinamic Acid

| Example | Name | Structure | [M + 1]+ |
|---|---|---|---|
| 29 | N-{2-[(S)-3-Hydroxy-pyrrolidin-1-yl]-(S)-1-phenyl-ethyl}-N-methyl-N'-phenyl-succinamide | 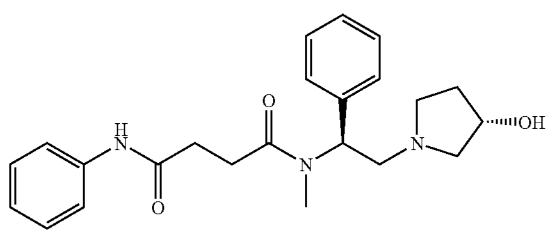 | 396 |
| 30 | N-[(S)-1-{(S)-3-Hydroxy-pyrrolidin-1-ylmethyl}-2-methyl-propyl]-N-methyl-N'-phenyl-succinamide | 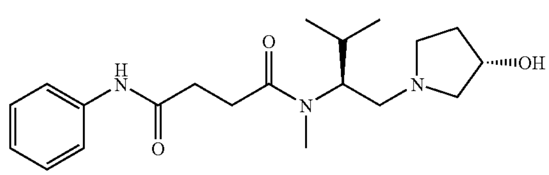 | 362 |
| 31 | 4-{(S)-2-[(S)-3-Hydroxy-pyrrolidin-1-ylmethyl]-piperidin-1-yl}-4-oxo-N-phenyl-butyramide | 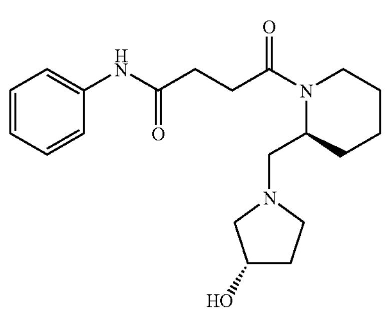 | 360 |

TABLE 3-continued

Derivatives of N-Substituted-succinamic Acid

| Example | Name | Structure | [M + 1]+ |
|---------|------|-----------|----------|
| 32 | N-{2-[(S)-3-Hydroxy-pyrrolidin-1-yl]-(S)-1-phenyl-ethyl}-N-methyl-N'-thiazol-2-yl-succinamide | 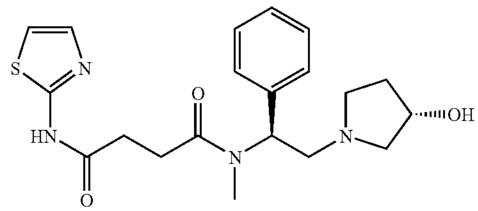 | 403 |
| 33 | N-{2-[(S)-3-Hydroxy-pyrrolidin-1-yl]-(S)-1-phenyl-ethyl}-N-methyl-N'-pyridin-3-yl-succinamide | 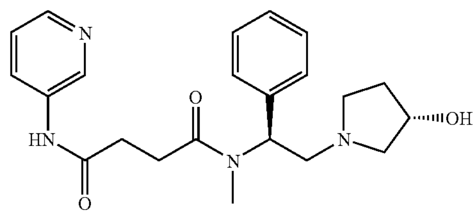 | 397 |

TABLE 4

Derivatives of (3-Phenyl-ureido)-acetic Acid

| Example | Name | Structure | [M + 1]+ |
|---------|------|-----------|----------|
| 34 | N-{2-[(S)-3-Hydroxy-pyrrolidin-1-yl]-(S)-1-phenyl-ethyl}-N-methyl-2-(3-phenyl-ureido)-acetamide | 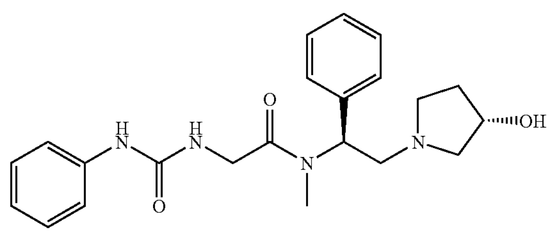 | 397 |
| 35 | N-[(S)-1-{(S)-3-Hydroxy-pyrrolidin-1-ylmethyl}-2-methyl-propyl]-N-methyl-2-(3-phenyl-ureido)-acetamide | 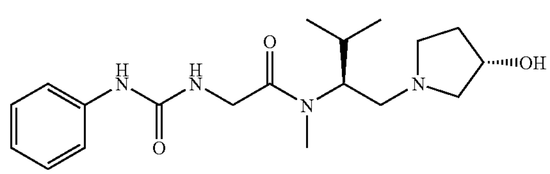 | 363 |
| 36 | 4-{(S)-2-[(S)-3-Hydroxy-pyrrolidin-1-ylmethyl]-piperidin-1-yl}-4-oxo-N-phenyl-butyramide | 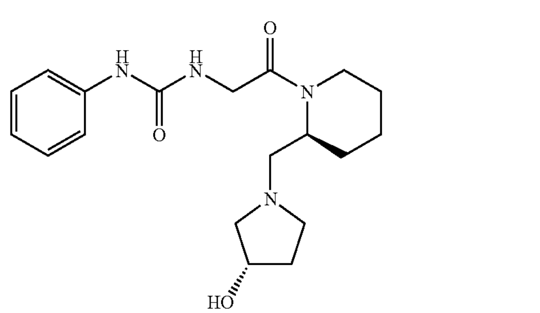 | 361 |

Additional objects, advantages, and novel features of this invention will become apparent to those skilled in the art upon examination of the following examples thereof, which are not intended to be limiting.

General Procedure for the Coupling of Acids With Diamines:

Method A: To a solution of the acid in methylene chloride (20 mL) was first added 1-(2-methylamino-(S)-2-phenyl-ethyl)-pyrrolidin-(S)-3-ol dihydrochloride (293 mg, 1.0 mmol) or other diamine (1.0 mmol), triethylamine (0.7 ml, 5 mmol) followed by the Mukaiyama acylating reagent, 2-chloro-1-methylpyridinium iodide (307 mg, 1.2 mmol). The reaction mixture was stirred at room temperature overnight and washed with saturated aqueous sodium bicarbonate (2×10 ml), and dried ($Na_2SO_4$). Evaporation of the solvent and purification of the residue by flash chromatography over silica gel (MeOH-$CH_2Cl_2$, 1:50 to 1:4) yielded the target compound.

Method B: To a suspension of 1-(2-methylamino-(S)-2-phenyl-ethyl)-pyrrolidin-(S)-3-ol dihydrochloride (323 mg, 1.1 mmol) or other diamine (1.1 mmol) in acetonitrile (40 mL) was added diisopropylethylamine (0.87 mL, 5 mmol) and the acid (1.0 mmol). After 10 minutes at room temperature, the reaction mixture was cooled to 0° C. and TBTU (386 mg, 1.2 mmol) was added portionwise. The reaction mixture was then stirred at room temperature overnight and concentrated. The residue was dissolved in ethyl acetate ( 50 mL) and washed with saturated sodium bicarbonate (2×30 mL), brine (30 mL) and dried (($Na_2SO_4$). Evaporation of the solvent and purification of the residue by flash chromatography over silica gel (MeOH-CH2Cl2, 1:50 to 1:4) yielded the target compound.

EXAMPLE 1

Preparation of N-{2-[(S)-3-Hydroxy-pyrrolidin-1-yl]-(S)-1-phenyl-ethyl}-N-methyl-2-phenylamino-acetamide Coupling of N-phenylglycine (0.307 g, 2 mmol) with 2-[(S)-3-hydroxy-pyrrolidin-1-yl]-(S)-1-phenyl-ethyl-methyl-amine dihydrochloride (0.715 g, 2.4 mmol) using the general coupling method B gave Example 1 (320 mg, 45%). $^1$H NMR (400 MHz, $CDCl_3$) δ: 7.43–7.13 (m, 7H), 6.73 (t, 1H), 6.64 (d, 2H), 6.07 (m, 1H), 4.96 (brs, 1H), 4.3 (brs, 1H), 3.9 (m, 2H), 3.25–2.6 (m, 8H), 2.4–1.6 (m, 4H); MS: [M+1]$^+$: 354.

EXAMPLE 2

Preparation of N-{2-[(S)-3-Hydroxy-pyrrolidin-1-yl]-(S)-1-phenyl-ethyl}-N-methyl-2-(methyl-phenyl-amino)-acetamide a) N-phenylglycine methyl ester To a stirred solution of the N-phenylglycine (5.45 g, 36 mmol) in methanol (100 mL) was added hydrogen chloride (50 mL, 4.0 M solution in dioxane, 200 mmol) and the mixture was stirred overnight at rt. The organic solvent was removed under reduced pressure and the residue was dissolved in dichloromethane (100 mL), washed with 1N sodium carbonate (3×50 mL), brine (50 mL), dried over $Na_2SO_4$, filtered, concentrated under reduced pressure and finally dried in vacuo to afford 5.85 g (98%) of the title compound. $^1$H NMR (400 MHz, $CDCl_3$) δ: 7.2 (m, 2H), 6.76 (m, 1H), 6.62 (m, 2H), 4.27 (brs, 1H), 3.93 (d, 2H), 3.78 (s, 3H).

b) (Methyl-phenyl-amino)-acetic acid methyl ester

The mixture of N-phenylglycine methyl ester (0.99 g, 6 mmol), potassium carbonate (1.66 g, 12 mmol), and iodomethane (1.28 g, 9 mmol) in acetonitrile (20 mL) was refluxed overnight. The solids were filtered and the filtrate was diluted with water (100 mL), extracted with dichloromethane (4×50 mL). The combined organic extracts were washed with brine (100 mL), dried ($Na_2SO_4$), filtered, and concentrated under reduced pressure. The crude product was purified by flash chromatography (silica gel, ethyl acetate/ hexane) to afford the title compound (0.82 g, 77%). $^1$H NMR (400 MHz, $CDCl_3$) δ: 7.24 (m, 2H), 6.75 (m, 1H), 6.67 (m, 2H), 4.07 (s, 2H), 3.71 (s, 3H), 3.06 (s, 3H).

c) (Methyl-phenyl-amino)-acetic acid hydrochloride

An aqueous solution of 10% hydrochloric acid (20 mL) containing the compound of Example 2-step b (0.80 g, 4.46 mmol) was stirred at reflux for 4 h. Water was removed under reduced pressure and the residue was dried in vacuo to give crude product (0.81 g) as solids. The solids were washed with acetone, dried in vacuo to afford the title compound (0.65 g, 72%). $^1$H NMR (400 MHz, DMSO-$d_6$) δ: 7.15 (m, 2H), 6.65 (m, 3H), 4.08 (s, 2H), 3.71 (s, 3H), 2.96 (s, 3H).

d) N-{2-[(S)-3-Hydroxy-pyrrolidin-1-yl]-(S)-1-phenyl-ethyl}-N-methyl-2-(methyl-phenyl-amino)-acetamide Coupling of the compound of Example 2-step c (0.63 g, 3.12 mmol) with 2-[(S)-3-hydroxy-pyrrolidin-1-yl]-(S)-1-phenyl-ethyl-methyl-amine dihydrochloride (1.1 g, 3.75 mmol), using the coupling method B yielded the Example 2 (0.86 g, 75%). $^1$H NMR (400 MHz, $CDCl_3$) δ: 7.43–7.15 (m, 7H), 6.78–6.61 (m, 3H), 6.05, 5.07 (m, 1H), 4.4–4.0 (m, 3H), 2.35–1.65 (m, 4H); MS: [M+1]$^+$: 368.

EXAMPLE 3

Preparation of N-{2-[(S)-3-Hydroxy-pyrrolidin-1-yl]-(S)-1-phenyl-ethyl}-N-methyl-2-(acetyl-phenyl-amino)-acetamide a) (Acetyl-phenyl-amino)-acetic acid methyl ester To the mixture of the compound of Example 2-step a (1.71 g, 10.35 mmol), potassium carbonate (4.29 g, 31.05 mmol) in acetonitrile (30 mL) at 0° C. was added dropwise acetyl chloride (1.1 mL, 15.53 mmol). After 30 min at 0° C., the mixture was warmed to room temperature and stirred overnight. The reaction mixture were filtered and the filtrate was diluted with water (100 mL), extracted with dichloromethane (4×50 mL). The combined organic extracts were washed with brine (100 mL), dried over $Na_2SO_4$, filtered, concentrated under reduced pressure, and dried in vacuo to afford the title compound (2.12 g, 99%). $^1$H NMR (400 MHz, $CDCl_3$) δ: 7.47–7.32 (m, 5H), 4.38 (s, 2H), 3.75 (s, 3H), 1.94 (s, 3H).

b) (Acetyl-phenyl-amino)-acetic acid

To a stirred solution of the Example 3-step a (0.58 g, 2.8 mmol) in a mixed solvent of methanol (15 mL), tetrahydrofuran (15 mL), and water (15 mL) was added lithium hydroxide monohydrate (0.47 g, 11.2 mmol) and the mixture was stirred at room temperature overnight. The organic solvent was removed under reduced pressure and the aqueous solution was acidified with 6N hydrochloric acid to pH~1. The resulting solids was collected by filtration, washed with water, and dried in vacuo to afford the title compound (0.45 g, 83%). $^1$H NMR (400 MHz, DMSO-$d_6$) δ: 12.72 (b,s, 1H), 7.5–7.3 (m, 5H), 4.25 (s, 2H), 1.8 (s, 3H).

c) N-{2-[(S)-3-Hydroxy-pyrrolidin-1-yl]-(S)-1-phenyl-ethyl}-N-methyl-2-(acetyl-phenyl-amino)-acetamide Coupling of the compound of Example 3-step b (0.42 g, 2.17 mmol) with 2-[(S)-3-hydroxy-pyrrolidin-1-yl]-(S)-1-phenyl-ethyl-methyl-amine dihydrochloride (0.76 g, 2.61 mmol) by using the general coupling method B furnished the Example 3 (0.68 g, 76%). $^1$H NMR (400 MHz, CDCl$_3$) δ: 7.5–7.15 (m, 10H), 6.1, 5.07 (m, 1H), 5.34, 4.82 (d, 1H), 4.4–4.0 (m, 2H), 3.4–2.75 (m, 4H), 2.7 (s, 3H), 2.65–2.0 (m, 4H), 1.96 (s, 3H), 1.8 (m, 1H); MS: [M+1]$^+$: 396.

EXAMPLE 4

Preparation of 2-(4-Cyano-phenylamino)-N-{2-[(S)-3-Hydroxy-pyrrolidin-1-yl]-(S)-1-phenyl-ethyl}-N-methyl-acetamide a) (4-Cyano-phenylamino)-acetic acid A solution of 4-aminobenzonitrile (12 g, 101.6 mmol) and chloroacetic acid (20 g, 211.6 mmol) in water (250 mL) was refluxed until the product began to separate out. After cooled down to the room temperature, the solids were collected by filtration, washed with ether, and dried in vacuo to afford 10.35 g (58%) of the title compound which was pure enough for the next reaction. $^1$H NMR (400 MHz, DMSO-d$_6$) δ 12.73 (s, 1H), 7.46 (dd, 2H), 6.93 (t, 1H), 6.65 (dd, 2H), 3.91 (d, 2H).

b) 2-(4-Cyano-phenylamino)-N-{2-[(S)-3-Hydroxy-pyrrolidin-1-yl]-(S)-1-phenyl-ethyl}-N-methyl-acetamide Coupling of the compound of Example 4-step a (0.26 g, 1.5 mmol) with 2-[(S)-3-hydroxy-pyrrolidin-1-yl]-(S)-1-phenyl-ethyl-methyl-amine dihydrochloride (0.53 g, 1.8 mmol) using the general coupling method B yielded the Example 4 (0.42 g, 74%). $^1$H NMR (400 MHz, CDCl$_3$) δ: 7.45 (d, 2H), 7.41–7.23 (m, 5H), 6.58 (d, 2H), 6.06, 4.93 (m, 1H), 5.6 (brs, 1H), 4.17, 3.92 (m, 2H), 3.28–2.65 (m, 8H), 2.4–1.67 (m, 4H); MS: [M+1]$^+$: 379.

EXAMPLE 5

Preparation of 2-(3-Cyano-phenylamino)-N-{2-[(S)-3-Hydroxy-pyrrolidin-1-yl]-(S)-1-phenyl-ethyl}-N-methyl-acetamide Compound 5 was prepared (0.43 g, 57%) following the same reaction sequence utilized in the preparation of 4 except that 3-aminobenzonitrile replaced 4-aminobenzonitrile as the starting material. $^1$H NMR (400 MHz, CDCl$_3$) δ: 7.47–7.2 (m, 6H), 6.99 (d, 1H), 6.85 (d, 1H), 6.8 (s, 1H), 6.07, 4.96 (m, 1H), 5.27 (brs, 1H), 4.32 (brs, 1H), 4.13, 3.98 (m, 2H), 3.3–2.65 (m, 8H), 2.45–1.6 (m, 4H); MS: [M+1]$^+$: 379.

EXAMPLE 6

Preparation of 2-(2-Cyano-phenylamino)-N-{2-[(S)-3-Hydroxy-pyrrolidin-1-yl]-(S)-1-phenyl-ethyl}-N-methyl-acetamide Compound 6 was prepared (0.575 g, 76%) following the same reaction sequence utilized in the preparation of 4 except that 2-aminobenzonitrile replaced 4-aminobenzonitrile as the starting material. $^1$H NMR (400 MHz, CDCl$_3$) δ: 7.47–7.25 (m, 7H), 6.7 (t, 1H), 6.57 (d, 1H), 6.08, 4.96 (m, 1H), 5.88 (b,t, 1H), 4.32 (b,s, 1H), 3.99 (m, 2H), 3.3–2.65 (m, 8H), 2.37–1.6 (m, 4H); MS: [M+1]$^+$: 379.

EXAMPLE 7

Preparation of 2-(4-Aminomethyl-phenylamino)-N-{$^2$-[(S)-3-Hydroxy-pyrrolidin-1-yl]-(S)-1-phenyl-ethyl}-N-methyl-acetamide The compound of Example 4-step b (189 mg, 0.5 mmol) in methanol (10 mL) was hydrogenated at room temperature overnight in the presence of concentrated HCl (0.25 mL, 3 mmol) and 10% palladium on activated carbon (113 mg) using a hydrogen balloon. The catalyst was removed by filtering through a celite pad and the clear filtrate was concentrated under reduced pressure to yield the compound of Example 7 (238 mg, 96.8%) as hydrochloride salt. $^1$H NMR (400 MHz, DMSO-d$_6$) δ: 8.15 (brt, 2H), 7.47–7.15 (m, 9H), 6.75 (dd, 1H), 6.15 (brt, 1H), 4.5–2.6 (m, 13H), 2.45–1.8 (m, 4H); MS: [M+1]$^+$: 383.

EXAMPLE 8

Preparation of 2-[(4-Cyano-phenyl)-methyl-amino]-N-{2-[(S)-3-Hydroxy-pyrrolidin-1-yl]-(S)-1-phenyl-ethyl}-N-methyl-acetamide a) (4-Cyano-phenyl-methylamino)-acetic acid methyl ester Potassium hydroxide powder (1.12 g, 20 mmol) in DMSO (7 mL) was stirred for 30 min at room temperature, then the compound of Example 4-step a (0.88 g, 5 mmol) was added and stirred for another 15 minutes. To the above reaction mixture was added dropwise iodomethane (1.25 mL, 20 mmol) and the mixture was stirred at room temperature overnight, quenched by addition of water (70 mL). The reaction mixture was extracted with diethyl ether (5×50 mL). The combined organic extracts were washed with saturated aqueous NaHCO$_3$ (100 mL), brine (50 mL), and dried over Na$_2$SO$_4$, filtered, concentrated under reduced pressure. The crude product was purified by flash chromatography (silica gel, ethyl acetate/hexane) to afford the title compound (0.48 g, 47%). $^1$H NMR (400 MHz, CDCl$_3$) δ: 7.49 (m, 2H), 6.65 (m, 1H), 4.07 (s, 2H), 3.71 (s, 3H), 3.06 (s, 3H).

b) (4-Cyano-phenyl-methylamino)-acetic acid

To a stirred solution of the Example 8-step a (0.45 g, 2.2 mmol) in a mixed solvent of methanol (20 mL), tetrahydrofuran (20 mL), and water (20 mL) was added lithium hydroxide monohydrate (0.37 g, 8.8 mmol) and the mixture was stirred overnight at rt. The organic solvent was removed under reduced pressure and the aqueous solution was acidified with solid citric acid to pH~4 and extracted with methylene chloride (3×40 mL). The combined extracts were washed with brine, dried over Na$_2$SO$_4$, filtered, and concentrated to afford the title compound (0.38 g, 91%). $^1$H NMR (400 MHz, CDCl$_3$) δ: 7.5 (m, 2H), 6.65 (m, 2H), 4.27 (s, 2H), 3.12 (s, 3H).

c) 2-[(4-Cyano-phenyl)-methyl-amino]-N-{2-[(S)-3-Hydroxy-pyrrolidin-1-yl]-(S)-1-phenyl-ethyl}-N-methyl-acetamide Coupling of the compound of Example 8-step b (0.30 g, 1.58 mmol) with 2-[(S)-3-hydroxy-pyrrolidin-1-yl]-(S)-1-phenyl-ethyl-methyl-amine dihydrochloride (0.56 g, 1.89 mmol), using the general coupling method B gave the Example 8 (0.46 g, 74%). $^1$H NMR (400 MHz, CDCl$_3$) δ: 7.52–7.25 (m, 7H), 6.6 (m, 2H), 6.02, 4.95 (m, 1H), 4.41, 4.3 (brs, 1H), 4.18 (d, 1H), 4.1 (d, 1H), 3.3–2.5 (m, 11H), 2.35–1.65 (m, 4H); MS: [M+1]$^{30}$: 393.

EXAMPLE 9

Preparation of N-{2-[(S)-3-Hydroxy-pyrrolidin-1-yl]-(S)-1-phenyl-ethyl}-2-[4-(methanesulfonylamino-methyl)-phenylamino]-N-methyl-acetamide a) (4-Aminomethyl-phenylamino)-acetic acid In a like manner as for the preparation of Example 7, the compound of Example 4-step a (5.29 g, 30 mmol) in methanol was hydrogenated to yield 7.6 g of the crude title compound as hydrochloride salts, which was used direct for the next step without further purification.

b) (4-Aminomethyl-phenylamino)-acetic acid methyl ester

To a stirred solution of the compound of Example 9-step a (7.6 g, 30 mmol) in methanol (100 mL) was added hydrogen chloride (4.0 M solution in dioxane, 50 mL, 200 mmol) The reaction mixture was stirred at room temperature overnight and concentrated in vacuo to give 7.62 g of the crude title compound as hydrochloride salts, which was used direct for the next step without further purification.

c) [4-(Methanesulfonylamino-methyl)-phenylamino]-acetic acid methyl ester

To a stirred solution of the compound of Example 9-step b (0.79 g, 2.96 mmol) and triethylamine (1.65 mL, 11.83 mmol) in dichloromethane (40 mL) at 0° C. was added methanesulfonyl chloride (0.25 mL, 3.25 mmol) dropwise. The reaction mixture was kept at 0° C. for another 30 minutes and then warmed to room temperature, and stirred overnight. The reaction mixture was washed with saturated aqueous NaHCO$_3$ (100 mL), dried (Na$_2$SO$_4$) and concentrated under reduced pressure. The crude product was purified by flash chromatography (silica gel, hexane/ethyl acetate) to give the pure title compound (0.65 g, 80% overall yield). $^1$H NMR (400 MHz, CDCl$_3$) δ: 7.27 (m, 2H), 6.59 (m, 2H), 4.7 (brs, 1H), 4.37 (brt, 1H), 4.2 (d, 2H), 3.92 (d, 2H), 3.79 (s, 3H), 2.85 (s, 3H).

d) [4-(Methanesulfonylamino-methyl)-phenylamino]-acetic acid

In a like manner as for the preparation of the compound of Example 8-step b, hydrolysis of the compound of the Example 9-step c (0.63 g, 2.3 mmol) with lithium hydroxide (0.39 g, 9.2 mmol) to afford the title compound (0.36 g, 58%). $^1$H NMR (400 MHz, DMSO-d$_6$) δ: 7.32 (t, 1H), 7.06 (m, 2H), 6.53 (m, 2H), 3.97 (d, 2H), 3.78 (s, 2H), 2.78 (s, 3H).

e) N-{2-[(S)-3-Hydroxy-pyrrolidin-1-yl]-(S)-1-phenyl-ethyl}-2-[4-(methanesulfonylamino-methyl)-phenylamino]-N-methyl-acetamide Coupling of the compound of Example 9-step d (0.34 g, 1.3 mmol) with 2-[(S)-3-hydroxy-pyrrolidin-1-yl]-(S)-1-phenyl-ethyl-methyl-amine dihydrochloride (0.46 g, 1.56 mmol) using the general coupling method B yielded the Example 9 (0.45 g, 75%). $^1$H NMR (400 MHz, CDCl$_3$) δ: 7.31 (m, 5H), 7.15 (m, 2H), 6.6 (m, 2H), 6.07, 4.98 (m, 1H), 5.03 (brs, 1H), 4.62 (brs, 1H), 4.29 (brs, 1H), 4.19 (d, 2H), 3.9 (m, 2H), 3.25–2.6 (m, 11H), 2.38–1.65 (m, 4H), MS: [M+1]$^+$: 461.

EXAMPLE 10

Preparation of N-{2-[(S)-3-Hydroxy-pyrrolidin-1-yl]-(S)-1-phenyl-ethyl}-2-[3-(methanesulfonylamino-methyl)-phenylamino]-N-methyl-acetamide Compound 10 was prepared (0.15 g, 68%). following the same reaction sequence utilized in the preparation of 9 except that (3-cyano-phenylamino)-acetic acid replaced (4-cyano-phenylamino)-acetic acid as the starting material. $^1$H NMR (400 MHz, CDCl$_3$) δ: 7.32 (m, 5H), 7.15 (t, 1H), 6.68 (d, 1H), 6.6 (m, 2H), 6.06 (dd, 1H), 5.04 (b,s, 2H), 4.28 (b,s, 1H), 4.22 (d, 2H), 3.9 (m, 2H), 3.3–2.65 (m, 11H), 2.45–1.6 (m, 4H); MS: [M+1]$^+$: 461.

EXAMPLE 11

Preparation of N-{2-[(S)-3-Hydroxy-pyrrolidin-1-yl]-(S)-1-phenyl-ethyl}-2-[2-(methanesulfonylamino-methyl)-phenylamino]-N-methyl-acetamide Compound 11 was prepared (0.30 g, 65%) following the same reaction sequence utilized in the preparation of 9 except that (2-cyano-phenylamino)-acetic acid replaced (4-cyano-phenylamino)-acetic acid as the starting material point. $^1$H NMR (400 MHz, CDCl$_3$) δ 7.42–7.2 (m, 6H), 7.18 (d, 1H), 6.78–6.65 (m, 2H), 6.04, 5.06, (dd, 1H), 5.45 (brs, 1H), 5.16 (brt, 1H), 4.4–4.2 (m, 3H), 3.98 (m, 2H), 3.3–2.97 (m, 2H), 2.92 (s, 3H), 2.82 (s, 3H), 2.76–2.63 (m, 3H), 2.3–1.5 (m, 4H); MS: [M+1]$^+$: 461.

EXAMPLE 12

Preparation of 2-(3,4-Dichloro-phenylamino)-N-{2-[(S)-3-hydroxy-pyrrolidin-1-yl]-(S)-1-phenyl-ethyl}-N-methyl-acetamide a) (3,4-Dichloro-phenylamino)-acetic acid The suspension of (3,4-dichloro-phenylamino)-acetic acid ethyl ester (0.38 g, 1.5 mmol) in 10% HCl (7 mL) was refluxed for 4 h. Water was removed under reduced pressure and the resulting solids were collected by filtration, washed with ether, and dried in vacuo to afford 0.33 g (84%) of the title compound as its hydrochloride salt. $^1$H-NMR (400 MHz, DMSO-d$_6$) δ: 7.26 (d, 1H), 6.75 (d, 1H), 6.56 (d, 1H), 5.85 (brs, 2–3H), 3.83 (s, 2H).

b) 2-(3,4-Dichloro-phenylamino)-N-{2-[(S)-3-hydroxy-pyrrolidin-1-yl]-(S)-1-phenyl-ethyl}-N-methyl-acetamide Coupling of the above acid from step a (0.32 g, 1.25 mmol) with 2-[(S)-3-hydroxy-pyrrolidin-1-yl]-(S)-1-phenyl-ethyl-methyl-amine dihydrochloride (0.44 g, 1.5 mmol) using the general coupling method B afforded Compound 12 (0.37 g, 70%). $^1$H NMR (400 MHz, CDCl$_3$) δ: 7.7–7.25 (m, 5H), 7.2 (d, 1H), 6.65 (d, 1H), 6.48 (dd, 1H), 6.06, 4.95 (dd, 1H), 4.31 (brs, 1H), 3.84 (m, 2H), 3.25–2.65 (m, 8H), 2.34 (m, 1H), 2.16 (m, 1H), 2.05–1.6 (m. 2H); MS: [M+1]$^+$: 422.

EXAMPLE 13

Preparation of 2-(4-Trifluoromethyl-phenylamino)-N-{2-[(S)-3-hydroxy-pyrrolidin-1-yl]-(S)-1-phenyl-ethyl}-N-methyl-acetamide a) (4-Trifluoromethyl-phenylamino)-acetic acid To a stirred solution of (4-trifluoromethyl-phenylamino)-acetic acid ethyl ester (0.37 g, 1.5 mmol) in a mixed solvent of methanol (10 mL), tetrahydrofuran (10 mL), and water (10 mL) was added lithium hydroxide monohydrate (0.25 g, 6 mmol) and the mixture was stirred at room temperature overnight. The organic solvent was removed under reduced pressure and the aqueous solution was acidified with solid citric acid to pH~4, and extracted with ethyl acetate (4×40 mL). The combined organic extracts were washed with brine, dried over Na$_2$SO$_4$ and concentrated to give 0.33 g of the crude title compound that was used direct for the next step without further purification. ¹H NMR (400 MHz, DMSO-d₆) δ: 12.68 (s, 1H), 7.38 (d, 2H), 6.66 (d, 2H), 3.87 (s, 2H).

b) 2-(4-Trifluoromethyl-phenylamino)-N-{2-[(S)-3-hydroxy-pyrrolidin-1-yl]-(S)-1-phenyl-ethyl}-N-methyl-acetamide Coupling of the compound of Example 13-step a (0.33 g, 1.5 mmol) with 2-[(S)-3-hydroxy-pyrrolidin-1-yl]-(S)-1-phenyl-ethyl-methyl-amine dihydrochloride (0.53 g, 1.8 mmol) using the general coupling method B gave the Example 13 (0.38 g, 60% overall yield). ¹H NMR (400 MHz, CDCl₃) δ: 7.7–7.25 (m, 7H), 6.63 (d, 2H), 6.07, 4.96 (dd, 1H), 5.37 (brs, 1H), 4.31 (brs, 1H), 3.92 (m, 2H), 3.35–2.6 (m, 8H), 2.34 (m, 1H), 2.16 (m, 1H), 1.95–1.67 (m, 2H), MS: [M+1]⁺: 422.

EXAMPLE 14

Preparation of 2-[(2,4-Dichloro-phenyl)-methanesulfonyl-amino]-N-{2-[(S)-3-hydroxy-pyrrolidin-1-yl]-(S)-1-phenyl-ethyl}-N-methyl-acetamide Coupling of the commercially available [(2,4-dichloro-phenyl)-methanesulfonyl-amino]-acetic acid (0.25 g, 0.82 mmol) with 2-[(S)-3-hydroxy-pyrrolidin-1-yl]-(S)-1-phenyl-ethyl-methyl-amine dihydrochloride (0.29 g, 0.98 mmol) using the coupling method B yielded the Example 14 (0.40 g, 97%). ¹H NMR (400 MHz, CDCl₃) δ: 7.95 (m, 1H), 7.51 (m, 1H), 7.36–7.1 (m, 6H), 6.05, 4.87 (dd, 1H), 4.23 (brs, 1H), 3.27–2.98 (m, 5H), 2.86–2.57 (m, 6H), 2.39–2.08 (m, 3H), 1.8–1.58 (m, 3H); MS: [M+1]⁺: 500.

EXAMPLE 15

Preparation of 2-(4-Nitro-phenylamino)-N-{2-[(S)-3-Hydroxy-pyrrolidin-1-yl]-(S)-1-phenyl-ethyl}-N-methyl-acetamide a) (4-Nitro-phenylamino)-acetic acid To a suspension of 4-nitroaniline (13.8 g, 100 mmol) in water (300 mL) was added chloroacetic acid (18.9 g, 200 mmol). The reaction mixture was refluxed overnight and cooled to rt. The title compound was collected by filtration, washed with water and a mixture of hexane and ether (1:1) and dried in vacuo to yield 14.6 g (74%). ¹H NMR (400 MHz, DMSO-d₆) δ: 12.83 (s, 1H), 8.00 (d, 2H), 7.45 (t, 1H), 6.65 (d, 2H), 4.00 (d, 2H).

b) 2-(4-Nitro-phenylamino)-N-{2-[(S)-3-Hydroxy-pyrrolidin-1-yl]-(S)-1-phenyl-ethyl}-N-methyl-acetamide Coupling of the (4-Nitro-phenylamino)-acetic acid from step a above (588 mg, 3.0 mmol) with 1-(2-methylamino-(S)-2-phenyl-ethyl)-pyrrolidin-(S)-3-ol dihydrochloride (967 mg, 3.3 mmol) using the general coupling method B gave the Example 15 (1.08 g, 90%). ¹H NMR (400 MHz, DMSO-d₆) δ: 8.00 (d, 2H), 7.35 (m, 6H), 6.70 (m, 2H), 5.80, 5.15 (m, total 1H), 4.78–4.70 (m, 1H), 4.26–4.10 (m, 3H), 3.12–1.52 (m, 11H); MS: [M+1]: 399.

EXAMPLE 16

Preparation of N-{2-[(S)-3-Hydroxy-pyrrolidin-1-yl]-(S)-1-phenyl-ethyl}-2-(4-methanesulfonylamino-phenylamino)-N-methyl-acetamide a) (4-Nitro-phenylamino)-acetic acid methyl ester To the solution of (4-nitro-phenylamino)-acetic acid from Example 15-step a (5.88 g, 30 mmol) in methanol (100 mL) was added hydrogen chloride (50 mL, 4.0 M in dioxane, 200 mmol) and the reaction mixture was stirred at room temperature overnight. Evaporation of the solvent gave the intermediate methyl ester (6.12 g, 97%). ¹H NMR (400 MHz, DMSO-d₆) δ: 8.00 (d, 2H), 7.52 (t, 1H), 6.67 (d, 2H), 4.12 (d, 2H), 3.68 (s, 3H).

b) [(4-Nitro-phenyl)-(2,2,2-trifluoro-acetyl)-amino]-acetic acid methyl ester

To the solution of the compound from step a above (2.10 g, 10 mmol) in methylene, chloride (80 mL) was added triethylamine (5.6 mL, 40 mmol) followed by dropwise addition of trifluoroacetic anhydride (2.12 mL, 15 mmol) at 0° C. The reaction mixture was stirred at 0° C. for 1 h, washed with saturated aqueous NaHCO₃ (2×40 mL) and dried over Na₂SO₄. Evaporation of the solvent gave the title compound (3.05 g, ~100%) which was pure enough for the next step. ¹H NMR (400 MHz, CDCl₃) δ: 8.31 (d, 2H), 7.62 (d, 2H), 4.43 (s, 2H), 3.80 (s, 3H).

c) [(4-Amino-phenyl)-(2,2,2-trifluoro-acetyl)-amino]-acetic acid methyl ester

The compound from step b above (3.05 g, 10 mmol) was dissolved in a mixture of methanol (100 mL) and methylene chloride (15 mL) and hydrogenated in the presence of 10% palladium on activated carbon (700 mg) using a hydrogen balloon at room temperature overnight. The reaction mixture was filtered and the filtrate was concentrated to give the title compound (2.74 g, ~100%) which was used direct for the next step. ¹H NMR (400 MHz, CDCl₃) δ: 7.13 (d, 2H), 7.63 (d, 2H), 4.36 (s, 2H), 3.78 (s, 3H), 3.65 (brs, 2H).

d) [(4-(Bismethanesulfonyl)amino-phenyl)-(2,2,2-trifluoro-acetyl)-amino]-acetic acid methyl ester To the solution of the compound from step c above (2.74 g, ~100%) in methylene chloride (100 mL) was added triethylamine (6.3 mL, 45 mmol) followed by dropwise addition of methanesulfonyl chloride (2.33 mL, 30 mmol) at 0 ° C. The reaction mixture was stirred at room temperature overnight, washed with saturated aqueous NaHCO₃ (2×60 mL) and dried over Na₂SO₄. Evaporation of the solvent and the residue was purified by flash chromatography over silica gel (ethyl acetate-methylene chloride-hexane, 1:1:1) to yield the bis sulfonamide ester (4.0 g, 92.6% for three steps). ¹H NMR (400 MHz, CDCl₃) δ: 7.52 (d, 2H), 7.43 (d, 2H), 4.42 (s, 2H), 3.80 (s, 3H), 3.41 (s, 6H).

e) (4-Methanesulfonylamino-phenylamino)-acetic acid

To the solution of the compound from step d above (3.9 g, 9.03 mmol) in a mixture of methanol (100 mL), tetrahydrofuran (100 mL) and water (100 mL) was added lithium hydroxide (4.2 g, 100 mmol). The reaction mixture was stirred at room temperature overnight and evaporated in vacuo to remove the most of the methanol and tetrahydrofuran. The residue was acidified by adding 3 N HCl to pH~5 and saturated with sodium chloride, and extracted with ethyl acetate (6×100 mL). The combined organic extracts were dried over Na₂SO₄ and concentrated to gave the corresponding acid (1.3 g, 59%). ¹H NMR (400 MHz, DMSO-d₆) δ: 8.99 (s, 1H), 6.95 (d, 2H), 6.51 (d, 2H), 3.78 (s, 2H), 2.81 (s, 3H).

f) N-{2-[(S)-3-Hydroxy-pyrrolidin-1-yl]-(S)-1-phenyl-ethyl}-2-(4-methanesulfonylamino-phenylamino)-N-methyl-acetamide Coupling of (4-methanesulfonylamino-phenylamino)-acetic acid from step e above (366 mg, 1.5 mmol) with 1-(2-methylamino-(S)-2-phenyl-ethyl)-pyrrolidin-(S)-3-ol dihydrochloride (487 mg, 1.66 mmol) using the general coupling method B yielded Compound 16 (295 mg, 44%).

$^1$H NMR (400 MHz, DMSO-d$_6$) δ: 8.99 (s, 1H), 7.30 (m, 5H), 6.95 (d, 2H), 6.60 (d, 2H), 5.80–5.66, 5.15 (m, total 2H), 4.70 (m, 1H), 4.15–3.90 (m, 3H), 3.06–2.30 (m, 12H), 1.95 (m, 1H), 1.53 (m, 1H); MS: [M+1]$^+$: 447.

EXAMPLE 17

Preparation of N-{2-[(S)-3-Hydroxy-pyrrolidin-1-yl]-(S)-1-phenyl-ethyl}-2-(4-propanesulfonylamino-phenylamino)-N-methyl-acetamide Compound 17 (0.30 g, 65%) was obtained by coupling of the [4-(propane-1-sulfonylamino)-phenylamino]-acetic acid with 1-(2-methylamino-(S)-2-phenyl-ethyl)-pyrrolidin-(S)-3-ol following the same reaction sequence utilized in the preparation of 16 except that propanesulfonyl chloride replaced methanesulfonyl chloride in step d.

[4-(propane-1-sulfonylamino)-phenylamino]-acetic acid: $^1$H NMR (400 MHz, DMSO-d$_6$) δ: 9.08 (s, 1H), 6.96 (d, 2H), 6.50 (d, 2H), 3.79 (s, 3H), 2.88 (m, 2H), 1.67 (m, 2H), 0.95 (t, 3H).

Example 17: $^1$H NMR (400 MHz, DMSO-d$_6$) δ: 9.08 (s, 1H), 7.30 (m, 5H), 6.95 (d, 2H), 6.60 (d, 2H), 5.80–5.66, 5.15 (m, total 2H), 4.70 (m, 1H), 4.16–3.90 (m, 3H), 3.06–2.30 (m, 11H), 1.95 (m, 1H), 1.66 (m, 2H), 1.50 (m, 1H), 0.95 (t, 3H); MS: [M+1]$^+$: 475.

EXAMPLES 18 AND 19

In like manner, coupling of the [4-(propane-1-sulfonylamino)-phenylamino]-acetic acid with 1-(3-methyl-(S)-2-methylamino-butyl)-pyrrolidin-(S)-3-ol and 1-piperidin-(S)-2-ylmethyl-pyrrolidin-(S)-3-ol afforded the compounds 18 and 19 respectively.

18: N-{(S)-1-[(S)-3-Hydroxy-pyrrolidin-1-ylmethyl]-2-methyl-propyl}-N-methyl-2-[4-(propane-1-sulfonylamino)-phenylamino]-acetamide $^1$H NMR (400 MHz, CDCl$_3$) δ: 7.08 (d, 2H), 6.58 (d, 2H), 6.21, 5.12 (brs, total 1H), 5.01, 4.47 (m, total 1H), 4.27 (brd, 1H), 4.07–3.79, 3.36–3.27 (m, 2H), 3.08–1.56 (m, 18H), 1.02 (m, 6H), 0.86 (m, 3H); MS: [M+1]$^+$: 441.

19: Propane-1-sulfonic acid (4-{2-[2-(S)-{(S)-3-hydroxy-pyrrolidin-1-ylmethyl}-piperidin-1-yl]-2-oxo-ethylamino}-phenyl)-amide $^1$H NMR (400 MHz, CDCl$_3$) δ: 7.08 (d, 2H), 6.57 (d, 2H), 6.29, 4.56 (brs, total 1H), 5.11–4.87 (m, 1H), 4.32 (m, 1H), 4.05–3.48 (m, 2H), 3.22–1.57 (m, 22H), 1.02 (t, 3H); MS: [M+]$^+$: 439.

EXAMPLE 20

Preparation of N-{2-[(S)-3-Hydroxy-pyrrolidin-1-yl]-(S)-1-phenyl-ethyl}-N-methyl-N'-phenyl-malonamide a) N-Phenyl-malonamic acid methyl ester To the ice-cooled solution of aniline (3,72 g, 40 mmol) in methylene chloride (300 mL) containing triethylamine (11.2 mL, 80 mmol) was added dropwise methyl 3-chloro-3-oxopropionate (5.37 mL, 50 mmol). The reaction mixture was then stirred at room temperature for 2 hours and washed with saturated aqueous NaHCO$_3$ (2×150 mL). The organic layer was dried (Na$_2$SO$_4$) and concentrated. The residue was purified by flash chromatography over silica gel (ethyl acetate-hexane, 1:2) to give the title compound (7.2 g, 93.3%). $^1$H NMR (400 MHz, CDCl$_3$) δ: 9.17 (brs, 1H), 7.53 (d, 2H), 7.32 (t, 2H), 7.10 (t, 1H), 3.80 (s, 2H).

b) N-Phenyl-malonamic acid

Hydrolysis of the N-Phenyl-malonamic acid methyl ester from step a (6.8 g, 35.2 mmol) with lithium hydroxide (8.9 g, 212 mmol) in a mixture of methanol (160 mL), tetrahydrofuran (160 mL) and water (160 mL) at room temperature for 3 h, afforded the title acid (5.76 g, 91.3%). $^1$H NMR (400 MHz, DMSO-d$_6$) δ: 12.64 (s, 1H), 10.11 (s, 1H), 7.58 (d, 2H), 7.31 (t, 2H), 7.06 (t, 1H), 3.36 (s, 2H).

c) N-{2-[(S)-3-Hydroxy-pyrrolidin-1-yl]-(S)-1-phenyl-ethyl}-N-methyl-N'-phenylmalonamide Coupling of the N-phenyl-malonamic acid from step b (394 mg, 2.2 mmol) with 1-(2-methylamino-(S)-2-phenyl-ethyl)-pyrrolidin-(S)-3-ol dihydrochloride (586 mg, 2.0 mmol) using the general coupling method A yielded the Example 20 (600 mg, 78.7%). $^1$H NMR (400 MHz, DMSO-d$_6$) δ: 10.18 (s, 1H), 7.60 (d, 2H), 7.31 (m, 7H), 7.05 (t, 1H), 5.80, 5.10 (m, total 1H), 4.70 (m, 1H), 4.18 (brs, 1H), 3.70–3.50 (m, 2H), 3.00–2.32 (m, 9H), 1.95 (m, 1H), 1.51 (m, 1H); MS: [M+1]$^+$: 382.

EXAMPLE 21

Preparation of N-{2-[(2-Hydroxy-ethyl)-methyl-amino]-(S)-1-phenyl-ethyl}-N-methyl-N'-phenyl-malonamide a) {(S)-[(2-Hydroxy-ethyl)-methyl-carbamoyl]-phenyl-methyl}-carbamic acid benzyl ester To a stirred solution of (S)-benzyloxycarbonylamino-phenyl-acetic acid (4.28 g, 15 mmol), 2-methylamino-ethanol (1.5 mL, 18 mmol), and diisopropylethylamine (6.3 mL, 36 mmol) in acetonitrile (60 mL) at 0° C. was added TBTU (5.78 g, 18 mmol) portionwise. The reaction mixture was stirred at room temperature overnight. The organic solvent was removed under reduced pressure and the residue was dissolved in ethyl acetate (100 mL), washed with 1N HCl (2×50 mL), saturated aqueous NaHCO$_3$ (2×50 mL), and brine (100 mL). The organic layer was dried (Na$_2$SO$_4$) and concentrated under reduced pressure. The crude product was purified by flash chromatography (silica gel, ethyl acetate/hexane) to afford the intermediate carbamic acid (4.79 g, 93%). $^1$H-NMR (400 MHz, CDCl$_3$) δ: 7.46–7.21 (m, 10H), 6.30, 6.17 (d, 1H), 5.78, 5.59 (2d, total 1H), 5.06 (m, 2H), 3.82–2.62 (m, 5H), 3.0, 2.94 (s, 3H).

b) 2-{Methyl-[(S)-2-methylamino-2-phenyl-ethyl]-amino}-ethanol

To a stirred solution of the compound from step a above (6.82 g, 19.9 mmol) in tetrahydrofuran (100 mL) at 0° C. was added lithium aluminum hydride (3.02 g, 19.68 mmol) portionwise. The reaction mixture was allowed to warm to room temperature and stirred overnight at 50° C. Upon cooling down to 0° C., the reaction mixture was quenched by dropwise addition of water (3.02 mL), 15% aqueous NaOH (3.02 mL), and water (9.06 mL). The mixture was stirred at room temperature for another 2 hours and filtered through a pad of Celite. The filtrate was concentrated under reduced pressure. The crude product was dissolved in 50 mL ether, to which was slowly added HCl (2.0 M solution in ether, 50 mL) and let stir for another 1 hour. The resulting solids were collected by filtration under nitrogen atmosphere, and washed with dry acetone until the washing was colorless. The solid was quickly transferred to a clean vial and dried under vacuum, yielding the corresponding title compound (4.56 g, 81%) as dihydrochloride salt. $^1$H-NMR (400 MHz, D$_2$O) δ: 7.61 (m, 5H), 4.13 (t, 1H), 3.88 (m, 3H), 3.34 (t, 2H), 2.89 (s, 3H), 2.606 (s, 3H).

c) N-{2-[(2-Hydroxy-ethyl)-methyl-amino]-(S)-1-phenyl-ethyl}-N-methyl-N'-phenyl-malonamide Coupling of the N-phenyl-malonamic acid (394 mg, 2.2 mmol) with 2-[methyl-(2-methylamino-(S)-2-phenyl-ethyl)-amino]-ethanol from step b above (562 mg, 2.0 mmol) using the general coupling method A yielded compound 21 (620 mg, 84%). $^1$H NMR (400 MHz, DMSO-d$_6$) δ: 10.14, 10.11 (2s, total 1H), 7.60 (d, 2H), 7.31 (m, 7H), 7.05 (t, 1H), 5.82, 5.12 (m, total 1H), 4.41, 4.35 (2t, total 1H), 3.72–3.46 (m, 4H), 2.95–2.50 (m, 7H), 2.31, 2.26 (2s, total 3H); MS: [M+1]$^+$: 370.

EXAMPLE 22

Preparation of N-[4-(Methanesulfonylamino-methyl)-phenyl]-N'-{2-[(S)-3-hydroxy-pyrrolidin-1-yl]-(S)-1-phenyl-ethyl}-N'-methyl-malonamide a) N-(4-Cyanophenyl)-malonamic acid methyl ester Using the same reaction condition employed in the preparation of N-phenyl-malonamic acid methyl ester, reaction of 4-aminobenzonitrile (4.72 g, 40 mmol) with methyl 3-chloro-3-oxopropionate (6.50 mL, 60 mmol) gave the intermediate cyano ester (7.55 g, 86.6%) after flash chromatography over silica gel (ethyl acetate-methylene chloride-hexane, 1:1:1). $^1$H NMR (400 MHz, CDCl$_3$) δ: 9.60 (s, 1H), 7.70 (d, 2H), 7.61 (d, 2H), 3.82 (s, 3H), 3.52 (s, 2H).

b) N-(4-Aminomethyl-phenyl)-malonamic acid methyl ester hydrochloride

The compound from step a above (7.0 g, 32.1 mmol) was dissolved in methanol (300 mL) and hydrogenated using a hydrogen balloon in the presence of 10% palladium on activated carbon (4.5 g) and concentrated HCl (10.5 mL). The reaction mixture was stirred at room temperature overnight and filtered. The filtrate was concentrated to yield the corresponding methylamino ester as its hydrochloride salt (8.3 g, ~100%) which was used direct for the next step. $^1$H NMR (400 MHz, DMSO-d$_6$) δ: 10.64 (s, 1H), 8.47 (brs, 2H), 7.62 (d, 2H), 7.45 (d, 2H), 3.95 (s, 2H), 3.65 (s, 3H), 3.53 (s, 2H).

c) N-[4-(Methanesulfonylamino-methyl)-phenyl]-malonamic acid methyl ester

To the suspension of the compound from step b above (2.58 g, 10 mmol) in methylene chloride (100 mL) at 0° C. was added triethylamine (8.4 mL, 60 mmol) followed by dropwise addition of methanesulfonyl chloride (2.33 mL, 30 mmol). The reaction mixture was stirred at room temperature for 2 hours and washed with saturated aqueous NaHCO$_3$ (2×60 mL). The organic layer was dried (Na$_2$SO$_4$) and concentrated. Purification of the residue by flash chromatography over silica gel (ethyl acetate-hexane, 5:1) afforded pure sulfonamide ester (450 mg, 15% for two steps). $^1$H NMR (400 MHz, CDCl$_3$) δ: 9.24 (s, 1H), 7.55 (d, 2H), 7.31 (d, 2H), 4.71 (t, 1H), 4.30 (d, 2H), 3.82 (s, 3H), 3.50 (s, 2H), 2.88 (s, 3H).

d) N-[4-(Methanesulfonylamino-methyl)-phenyl]-malonamic acid

Standard basic hydrolysis of the compound from step c above (400 mg, 1.33 mmol) with lithium hydroxide (278 mg, 6.6 mmol) yielded the title acid (361 mg, 94.7%). $^1$H NMR (400 MHz, DMSO-d$_6$) δ: 10.15 (s, 1H), 7.55 (d, 2H), 7.50 (t, 1H), 7.28 (d, 2H), 4.10 (d, 2H), 3.35 (s, 2H), 2.82 (s, 3H).

e) N-[4-(Methanesulfonylamino-methyl)-phenyl]-N'-{2-[(S)-3-hydroxy-pyrrolidin-1-yl]-(S)-1-phenyl-ethyl}-N'-methyl-malonamide Coupling of the above acid from step d above(270 mg, 0.944 mmol) with 1-(2-methylamino-(S)-2-phenyl-ethyl)-pyrrolidin-(S)-3-ol dihydrochloride (264 mg, 0.9 mmol) using the general method A gave compound 22 (350 mg, 80%). $^1$H NMR (400 MHz, DMSO-d$_6$) δ: 10.16, 10.12 (2s, total 1H), 7.55 (d, 2H), 7.50 (t, 1H), 7.40–7.35 (m, 5H), 7.28 (d, 2H), 5.78, 5.10 (m, total 1H), 4.72, 4.66 (m, total 1H), 4.15–4.09 (m, 3H), 3.70–3.45 (m, 2H), 3.00–2.30 (m, 12H), 1.95 (m, 1H), 1.50 (m, 1H); MS: [M+1]$^+$: 489.

EXAMPLE 23

Preparation of N-[4-(Ethanesulfonylamino-methyl)-phenyl]-N'-{2-[(S)-3-hydroxy-pyrrolidin-1-yl]-(S)-1-phenyl-ethyl}-N'-methyl-malonamide Following the same reaction sequence as employed in the preparation of compound 22 except that ethanesulfonyl chloride replaced methanesulfonyl chloride in step c, compound 23 (340 mg, 75%) was obtained by coupling of N-[4-(ethanesulfonylamino-methyl)-phenyl]-malonamic acid (284 mg, 0.944 mmol) with 1-(2-methylamino-(S)-2-phenyl-ethyl)-pyrrolidin-(S)-3-ol dihydrochloride (264 mg, 0.9 mmol).

N-[4-(ethanesulfonylamino-methyl)-phenyl]-malonamic acid: $^1$H NMR (400 MHz, DMSO-d$_6$) δ: 10.14 (s, 1H), 7.55 (m, 3H), 7.28 (d, 2H), 4.09 (d, 2H), 3.35 (s, 2H), 2.90 (q, 2H), 1.15 (t, 3H).

Example 23: $^1$H NMR (400 MHz, DMSO-d$_6$) δ: 10.14 (s, 1H), 7.55 (m, 3H), 10.18 (s, 1H), 7.56–7.32 (m, 8H), 7.28 (d, 2H), 5.78, 5.10 (m, total 1H), 4.70 (m, 1H), 4.18 (m, 1H), 4.10 (d, 2H), 3.70–3.45 (m, 2H), 3.00–2.30 (m, 13H), 1.95 (m, 1H), 1.52 (m, 1H), 1.15 (t, 3H); MS: [M+1]$^+$: 503.

EXAMPLE 24

Preparation of N-{2-[(S)-3-Hydroxy-pyrrolidin-1-yl]-(S)-1-phenyl-ethyl}-N'-(4-methanesulfonylamino-phenyl)-N-methyl-malonamide a) N-(4-Nitro-phenyl)-malonamic acid methyl ester Using the same reaction conditions described above for the preparation of the intermediate compound in Example 20-step a, 4-nitroaniline (3.45 g, 25 mmol) was reacted with methyl 3-chloro-3-oxopropionate (4.07 mL, 37.5 mmol) to give the intermediate ester (5.4 g, 90.8%). $^1$H NMR (400 MHz, DMSO-d$_6$) δ: 10.80 (s, 1H), 8.23 (d, 2H), 7.81 (d, 2H), 3.68 (s, 3H), 3.58 (s, 2H).

b) N-(4-Amino-phenyl)-malonamic acid methyl ester

The compound from step a above (5.0 g, 21 mmol) was hydrogenated as described in Example 16-step c, affording the title aniline derivative (4.36 g, ~100%). $^1$H NMR (400 MHz, CDCl$_3$) δ: 7.29 (d, 2H), 6.63 (d, 2H), 3.80 (s, 3H), 3.65 (brs, 2H), 3.45 (s, 2H).

c) N-(4-Bis(methanesulfonyl)amino-phenyl)-malonamic acid methyl ester

The compound from step b above (2.08 g, 10 mmol) was mesylated to give the bis sulfonamide ester (3.0 g, 82.4%) using the same reaction conditions described in the preparation of the compound in Example 16-step d. $^1$H NMR (400 MHz, DMSO-d$_6$) δ: 10.45 (s, 1H), 7.65 (d, 2H), 7.46 (d, 2H), 3.63 (s, 3H), 3.50 (s, 8H).

d) N-(4-Methanesulfonylamino-phenyl)-malonamic acid

Standard basic hydrolysis of the compound from step c above (2.6 g, 7.14 mmol) with lithium hydroxide (2.52 g, 60 mmol) gave the corresponding acid (1.71 g, 88%). $^1$H NMR (400 MHz, DMSO-d$_6$) δ: 12.62 (brs, 1H), 10.12 (s, 1H), 9.56 (s, 1H), 7.53 (d, 2H), 7.14 (d, 2H), 3.32 (s, 2H), 2.92 (s, 3H).

e) N-{2-[(S)-3-Hydroxy-pyrrolidin-1-yl]-(S)-1-phenyl-ethyl}-N'-(4-methanesulfonylamino-phenyl)-N-methyl-malonamide Coupling of the above acid from step d (599 mg, 2.2 mmol) with 1-(2-methylamino-(S)-2-phenyl-ethyl)-pyrrolidin-(S)-3-ol dihydrochloride (586 mg, 2.0 mmol) using the general method A gave compound 24 (450 mg, 47.5%). $^1$H NMR (400 MHz, DMSO-d$_6$) δ: 10.18 (s, 1H), 9.58 (s, 1H), 7.55 (d, 2H), 7.35 (m, 5H), 7.16 (d, 2H), 5.81, 5.10 (m, total 1H), 4.70 (m, 1H), 4.20 (m, 1H), 3.70–3.46 (m, 2H), 3.15–2.35 (m, 9H), 1.95 (m, 1H), 1.55 (m, 1H); MS: [M+1]$^+$: 475.

EXAMPLE 25

Preparation of N-{2-[(S)-3-Hydroxy-pyrrolidin-1-yl]-(S)-1-phenyl-ethyl}-N-methyl-N'-[2-(pyrrolidine-1-sulfonyl)-phenyl]-malonamide a) 1-(2-Nitro-benzenesulfonyl)-pyrrolidine 2-Nitrobenzenesulfonyl chloride (4.43 g, 20 mmol) in methylene chloride (20 mL) was added dropwise to the ice-cooled solution of pyrrolidine (8.4 mL, 100 mmol) in methylene chloride (100 mL). The reaction mixture was stirred at room temperature for 2 hours and washed with 3N HCl (2×60 mL) and brine (60 mL). The organic layer was dried (Na$_2$SO$_4$) and concentrated to yield the intermediate nitrobenzene derivative (5.12 g, 100%). $^1$H NMR (400 MHz, CDCl$_3$) δ: 8.00 (d, 1H), 7.70 (m, 2H), 7.60 (d, 1H), 3.40 (t, 4H), 1.92 (t, 4H), 1.80 (t, 4H).

b) 2-(Pyrrolidine-1-sulfonyl)-phenylamine

Hydrogenation of the compound from step a above (5.0, 19.53 mmol) following the same reaction conditions as described in Example 16-step c to furnish the corresponding aniline compound (4.41 g, ~100%) which was used directly in the next step without further purification. $^1$H NMR (400 MHz, CDCl$_3$) δ: 7.63 (d, 1H), 7.28 (m, 1H), 6.73 (m, 2H), 5.09 (brs, 2H), 3.30 (t, 4H), 1.80 (t, 4H).

c) N-[2-(Pyrrolidine-1-sulfonyl)-phenyl]-malonamic acid methyl ester

Using the same reaction condition as described in Example 20-step a, the compound from step b above (crude, 19.53 mmol) was reacted with methyl 3-chloro-3-oxopropionate (3.25 mL, 30 mmol) to give the malonamic acid ester (4.8 g) which was contaminated with a byproduct having very close R$_f$. This crude product was used without further purification for the next step.

d) N-[2-(Pyrrolidine-1-sulfonyl)-phenyl]-malonamic acid

Standard basic hydrolysis of the above crude compound (4.8 g, 14.7 mmol) with lithium hydroxide (4.2 g, 100 mmol) gave the crude acid which was purified by flash chromatography over silica gel (ethyl acetate-methylene chloride-hexane, 3:1:1), yielding the pure malonamic acid compound (2.44 g, 40% overall yield for three steps). $^1$H NMR (400 MHz, DMSO-d$_6$) δ: 12.88 (s, 1H), 9.90 (s, 1H), 8.18 (d, 1H), 7.80 (d, 1H), 7.67 (t, 1H), 7.38 (t, 1H), 3.50 (s, 2H), 3.16 (t, 4H), 1.70 (t, 4H).

e) N-{2-[(S)-3-Hydroxy-pyrrolidin-1-yl]-(S)-1-phenyl-ethyl}-N-methyl-N'-[2-(pyrrolidine-1-sulfonyl)-phenyl]-malonamide Coupling of the compound from step d above (515 mg, 1.65 mmol) with 1-(2-methylamino-(S)-2-phenyl-ethyl)-pyrrolidin-(S)-3-ol dihydrochloride (440 mg, 1.5 mmol) using the general method A gave compound 25 (656 mg, 85%). $^1$H NMR (400 MHz, DMSO-d$_6$) δ: 10.03 (s, 1H), 8.20 (m, 1H), 7.83 (d, 1H), 7.68 (t, 1H), 7.32 (m, 6H), 5.80, 5.12 (m, total 1H), 4.68 (m, 1H), 4.12 (m, 1H), 3.85–3.60 (m, 2H), 3.15 (m, 4H), 3.00–2.30 (m, 9H) 1.90 (m, 1H), 1.70 (m, 4H), 1.50 (m, 1H); MS: [M+1]$^+$: 515.

EXAMPLE 26

Preparation of N-Benzyl-N'-{2-[(S)-3-hydroxy-pyrrolidin-1-yl]-(S)-1-phenyl-ethyl}-N'-methyl-malonamide a) N-Benzyl-malonamic acid methyl ester Using the same reaction conditions as described in Example 20-step a, benzylamine (2.68 g, 25 mmol) was reacted with methyl 3-chloro-3-oxopropionate (4.07 mL, 37.5 mmol) to give the malonamic acid ester compound (4.3 g, 82.9%). $^1$H NMR (400 MHz, CDCl$_3$) δ: 7.40 (brs, 1H), 7.30 (m, 5H), 4.50 (d, 2H), 3.75 (s, 3H), 3.38 (s, 2H).

b) N-Benzyl-malonamic acid

Standard basic hydrolysis of the compound from step a above (4.0 g, 19.3 mmol) with lithium hydroxide (4.2 g, 100 mmol) gave the corresponding acid (3.72 g, ~100%). 1H NMR (400 MHz, DMSO-d$_6$) δ: 12.52 (s, 1H), 8.55 (t, 1H), 7.30 (m, 5H), 4.30 (d, 2H), 3.20 (s, 2H).

c) N-Benzyl-N'-{2-[(S)-3-hydroxy-pyrrolidin-1-yl]-(S)-1-phenyl-ethyl}-N'-methyl-malonamide Coupling of the above acid from step b above(425 mg, 2.2 mmol) with 1-(2-methylamino-(S)-2-phenyl-ethyl)-pyrrolidin-(S)-3-ol dihydrochloride (585 mg, 2.0 mmol) using the general method A gave compound 26 (620 mg, 78.5%). $^1$H NMR (400 MHz, DMSO-d$_6$) δ: 8.51 (brs, 1H), 7.30 (m, 10H), 5.80, 5.08 (m, total 1H), 4.70 (m, 1H), 4.29 (m, 2H), 4.18 (m, 1H), 3.57–3.33 (m, 2H), 2.98–2.40 (m, 9H), 1.95 (m, 1H), 1.53 (m, 1H); MS: [M+1]$^+$: 396.

EXAMPLE 27

Preparation of N-{2-[(S)-3-Hydroxy-pyrrolidin-1-yl]-(S)-1-phenyl-ethyl}-N-methyl-N'-thiazol-2-yl-malonamide a) N-Thiazol-2-yl-malonamic acid methyl ester Under the same reaction conditions as described in Example 20-step a, 2-aminothiazole (2.5 g, 25 mmol) was reacted with methyl 3-chloro-3-oxopropionate (4.07 mL, 37.5 mmol) to give the malonamic acid ester compound (3.8 g, 76%). $^1$H NMR (400 MHz, CDCl$_3$) δ: 7.50 (d, 1H), 7.25 (d, 1H), 3.66 (s, 3H), 3.60 (s, 2H).

b) N-Thiazol-2-yl-malonamic acid

Standard basic hydrolysis of the compound from step a above (3.5 g, 17.5 mmol) with lithium hydroxide (3.7 g, 80 mmol) yielded the corresponding acid (1.63 g, 50%). $^1$H NMR (400 MHz, DMSO-d$_6$) δ: 12.80 (br, 1H), 12.35 (br, 1H), 7.49 (d, 1H), 7.23 (d, 1H), 3.50 (s, 2H).

c) N-{2-[(S)-3-Hydroxy-pyrrolidin-1-yl]-(S)-1-phenyl-ethyl}-N-methyl-N'-thiazol-2-yl-malonamide Coupling of the above acid from step b (410 mg, 2.2 mmol) with 1-(2-methylamino-(S)-2-phenyl-ethyl)-pyrrolidin-(S)-3-ol dihydrochloride (585 mg, 2.0 mmol) using the general method A gave compound 27 (500 mg, 64.4%). $^1$H NMR (400 MHz, DMSO-d$_6$) δ: 12.22 (br, 1H), 7.49 (d, 1H), 7.35 (m, 5H), 7.23 (d, 1H), 5.78, 5.03 (m, total 1H), 4.70 (m, 1H), 4.19 (m, 1H), 3.85–3.60 (m, 2H), 2.98–2.32 (m, 9H), 1.95 (m, 1H), 1.55 (m, 1H); MS: [M+1]$^+$: 389.

EXAMPLE 28

Preparation of N-[2-[(S)-3-Hydroxy-pyrrolidin-1-yl]-(S)-1-phenyl-ethyl]-N-methyl-N'-pyridin-3-yl-malonamide a) Benzyl 3-chloro-3-oxopropionate To the solution of commercially available mono-benzyl malonate (Aldrich Chemical Co., Milwaukee, Wis.) (7.76 g, 40 mmol) in methylene chloride (100 mL) was added oxalyl chloride (14 mL, 160 mmol) followed by 3 drops of dimethylformamide. The reaction mixture was stirred at room temperature for 3 hours and concentrated in vacuo.

b) N-Pyridin-3-yl-malonamic acid benzyl ester

The crude acyl chloride from step a above was dissolved in methylene chloride (20 mL) and added to the ice-cooled solution of 3-aminopyridine (2.66 g, 28 mmol) in methylene chloride (200 mL) containing triethylamine (11.2 mL, 80 mmol). The reaction mixture was stirred at room temperature for 2 hours and then washed with saturated aqueous NaHCO$_3$ (2×80 mL). The organic layer was dried (Na$_2$SO$_4$) and concentrated. Purification of the residue by flash chromatography over silica gel (methylene chloride-acetone, 8:1–1:1) gave the malonamic acid ester compound (5.33 g, 70.5%). $^1$H NMR (400 MHz, CDCl$_3$) δ: 9.41 (s, 1H), 8.60 (s, 1H), 8.36 (d, 1H), 8.13 (m, 1H), 7.38 (m, 5H), 7.27 (m, 1H), 5.25 (s, 2H), 3.54 (s, 2H).

c) N-Pyridin-3-yl-malonamic acid

Standard hydrogenation from step b above (5.0 g, 18.52 mmol) in methanol in the presence of 10% palladium on activated carbon (1.2 g) yielded the corresponding acid (1.70 g, 50%). $^1$H NMR (400 MHz, DMSO-d$_6$) δ: 10.55 (s, 1H), 8.70 (s, 1H), 8.26 (d, 1H), 8.02 (m, 1H), 7.34 (m, 1H), 3.35 (s, 2H).

d) N-[2-[(S)-3-Hydroxy-pyrrolidin-1-yl]-(S)-1-phenyl-ethyl]-N-methyl-N'-pyridin-3-yl-malonamide Coupling of the above acid from step c (396 mg, 2.2 mmol) with 1-(2-methylamino-(S)-2-phenyl-ethyl)-pyrrolidin-(S)-3-ol dihydrochloride (585 mg, 2.0 mmol) using the general method A gave compound 28 (459 mg, 60%). $^1$H NMR (400 MHz, DMSO-d$_6$) δ: 10.38 (s, 1H), 8.71 (s, 1H), 8.26 (d, 1H), 8.04 (m, 1H), 7.40–7.28 (m, 6H), 5.78, 5.10 (m, total 1H), 4.72 (m, 1H), 4.17 (m, 1H), 3.75–3.50 (m, 2H), 2.99–2.30 (m, 9H), 1.93 (m, 1H), 1.52 (m, 1H); MS: [M+1]$^+$: 383.

EXAMPLE 29

Preparation of N-{2-[(S)-3-Hydroxy-pyrrolidin-1-yl]-(S)-1-phenyl-ethyl}-N-methyl-N'-phenyl-succinimide a) N-Phenyl-succinamic acid methyl ester Using the same reaction conditions as described in Example 20-step a except that methyl 4-chloro-3-oxobutyrate replaced methyl 3-chloro-3-oxopropionate, aniline (2.33 g, 25 mmol) was converted to the succinamide compound (5.18 g, 100%) after purification by chromatography over silica gel. $^1$H NMR (400 MHz, CDCl$_3$) δ: 7.70 (s, 1H), 7.50 (d, 2H), 7.30 (t, 2H), 7.09 (m, 1H), 3.70 (s, 3H), 2.73–2.65 (m, 4H).

b) N-Phenyl-succinamic acid

Standard basic hydrolysis of the compound from step a above (5.1 g, 24.64 mmol) with lithium hydroxide (5.46 g, 130 mmol) afforded the corresponding acid (4.71 g, ~100%). $^1$H NMR (400 MHz, DMSO-d$_6$) δ: 12.13 (s, 1H), 9.95 (s, 1H), 7.60 (d, 2H), 7.30 (t, 2H), 7.00 (t, 1H), 2.54 (m, 4H).

c) N-{2-[(S)-3-Hydroxy-pyrrolidin-1-yl]-(S)-1-phenyl-ethyl}-N-methyl-N'-phenyl-succinamide Coupling of the acid from step b above (425 mg, 2.2 mmol) with 1-(2-methylamino-(S)-2-phenyl-ethyl)-pyrrolidin-(S)-3-ol dihydrochloride (585 mg, 2.0 mmol) using the general method A gave compound 29 (600 mg, 76%). $^1$H NMR (400 MHz, DMSO-d$_6$) δ: 9.95 (s, 1H), 7.60 (d, 2H), 7.35–7.25 (m, 7H), 7.00 (m, 1H), 5.81, 5.12 (m, total 1H), 4.70 (m, 1H), 4.18 (m, 1H), 2.95–2.25 (m, 13H), 1.95 (m, 1H), 1.53 (m, 1H); MS: [M+1]$^+$: 396.

EXAMPLES 30 AND 31

In like manner, coupling of the N-phenyl-succinamic acid from Example 29-step b with 1-(3-methyl-(S)-2-methylamino-butyl)-pyrrolidin-(S)-3-ol or 1-piperidin-(S)-2-ylmethyl-pyrrolidin-(S)-3-ol afforded compound 30 or 31 respectively.

EXAMPLE 30

N-[(S)-1-{(S)-3-Hydroxy-pyrrolidin-1-ylmethyl}-2-methyl-propyl]-N-methyl-N'-phenyl-succinamide $^1$H-NMR (400 MHz, CDCl$_3$) δ: 8.68, 8.40 (2brs, total 1H), 7.51 (m, 2H), 7.28 (m, 2H), 7.05 (m, 1H), 4.59–1.92 (m, 17H), 1.82–1.42 (m, 2H), 0.99 (m, 3H), 0.83 (m, 3H); MS: [M+1]$^+$: 362.

EXAMPLE 31

4-{(S)-2-[(S)-3-Hydroxy-pyrrolidin-1-ylmethyl]-piperidin-1-yl}-4-oxo-N-phenyl-butyramide $^1$H-NMR (400 MHz, CDCl$_3$) δ: 8.61, 8.46 (brs, 1H), 7.52 (m, 2H), 7.28 (m, 2H), 7.05 (m, 1H), 4.93, 4.34–4.06 (m, total 2H), 4.56, 3.69 (2d, total 1H), 3.16–2.94 (m, 2H), 2.88–1.31 (m, 18H); MS: [M+1]$^+$: 360.

EXAMPLE 32

Preparation of N-{2-[(S)-3-Hydroxy-pyrrolidin-1-yl]-(S)-1-phenyl-ethyl}-N-methyl-N'-thiazol-2-yl-succinamide Using the same reaction sequence employed in Example 27 except that methyl 4-chloro-4-butyrate replaced methyl 3-chloro-3-oxopropionate, compound 32 was prepared.

a) N-Thiazol-2-yl-succinamic acid methyl ester $^1$H NMR (400 MHz, DMSO-$d_6$) δ: 12.16 (s, 1H), 7.45 (d, 1H), 7.18 (d, 1H), 3.60 (s, 3H), 2.70 (t, 2H), 2.62 (t, 2H).

b) N-Thiazol-2-yl-succinamic acid $^1$H NMR (400 MHz, DMSO-$d_6$) δ: 12.16 (brs, 2H), 7.45 (d, 1H), 7.20 (d, 1H), 2.63 (t, 2H), 2.52 (t, 2H).

c) N-{2-[(S)-3-Hydroxy-pyrrolidin-1-yl]-(S)-1-phenyl-ethyl}-N-methyl-N'-thiazol-2-yl-succinamide $^1$H NMR (400 MHz, DMSO-$d_6$) δ: 12.10 (s, 1H), 7.45 (d, 1H), 7.38–7.28 (m, 5H), 7.19 (d, 1H), 5.78, 5.12 (m, total 1H), 4.70 (m, 1H), 4.16 (m, 1H), 2.96–2.25 (m, 13H), 1.95 (m, 1H), 1.51 (m, 1H); MS: [M+1]$^+$: 403.

EXAMPLE 33

Preparation of N-{2-[(S)-3-Hydroxy-pyrrolidin-1-yl]-(S)-1-phenyl-ethyl}-N-methyl-N'-pyridin-3-yl-succinamide a) Succinic acid monobenzyl ester To the ice-cooled solution of benzyl alcohol (12.96 g, 120 mmol) in methylene chloride (300 mL) was added triethylamine (25 mL, 180 mmol), 4-dimethylaminopyridine (610 mg, 5 mmol) followed by dropwise addition of succinic anhydride (10 g, 100 mmol). The reaction mixture was stirred at room temperature overnight and washed with 1N HCl (2×100 mL) and brine (100 mL). The organic layer was dried (Na$_2$SO$_4$) and concentrated. The residue was dissolved in ethyl acetate (150 mL) and extracted with saturated aqueous NaHCO$_3$ (3×150 mL). The combined aqueous layers were acidified with concentrated HCl to pH=1–2, and extracted with methylene chloride (4×250 mL). The combined organic layers were dried (Na$_2$SO$_4$) and concentrated to give the title acid (19.5 g, 93.8%). $^1$H NMR (400 MHz, CDCl$_3$) δ: 11.80–10.50 (br, 1H), 7.35 (m, 5H), 5.15 (s, 2H), 2.70 (m, 4H).

Succinic acid monobenzyl ester was converted to compound 33 by following the same reaction sequence and conditions as described for the preparation of compound 28.

b) Benzyl 4-chloro-4-butyrate

The crude benzyl 4-chloro-4-butyrate that was prepared by reaction of succinic acid monobenzyl ester with oxalyl chloride, and was used directly in the next step.

c) N-Pyridin-3-yl-succinamic acid benzyl ester $^1$H NMR (400 MHz, DMSO-$d_6$) δ: 10.22 (s, 1H), 8.70 (d, 1H), 8.22 (d, 1H), 8.01 (m, 1H), 7.35 (m, 6H), 5.10 (s, 2H), 2.68 (m, 4H).

d) N-Pyridin-3-yl-succinamic acid $^1$H NMR (400 MHz, DMSO-$d_6$) δ: 12.10–11.00 (br, 1H), 10.21 (s, 1H), 8.70 (d, 1H), 8.22 (d, 1H), 8.01 (m, 1H), 7.32 (m, 1H), 2.57–2.50 (m, 4H).

e) N-{2-[(S)-3-Hydroxy-pyrrolidin-1-yl]-(S)-1-phenyl-ethyl}-N-methyl-N'-pyridin-3-yl-succinamide $^1$H NMR (400 MHz, DMSO-$d_6$) δ: 10.29 (s, 1H), 8.75 (d, 1H), 8.22 (d, 1H), 8.05 (m, 1H), 7.53–7.28 (m, 6H), 5.85, 5.12 (m, total 1H), 4.73 (br, 1H), 4.20 (m, 1H), 3.15–2.27 (m, 13H), 1.98 (m, 1H), 1.57 (m, 1H); MS: [M+1]$^+$: 397.

EXAMPLE 34

Preparation of N-{2-[(S)-3-Hydroxy-pyrrolidin-1-yl]-(S)-1-phenyl-ethyl}-N-methyl-2-(3-phenyl-ureido)-acetamide a) (3-Phenyl-ureido)-acetic acid methyl ester To a stirred suspension of glycine methyl ester hydrochloride (4.52 g, 36 mmol) in methylene chloride (200 mL) was added triethylamine (5.0 mL, 36 mmol) at room temperature and stirred for 15 minutes. To the reaction mixture was added dropwise phenyl isocyanate (3.57 g, 30 mmol). The reaction mixture was stirred at room temperature for 2 hours and washed with 1N HCl (2×80 mL) and brine (80 mL). The organic layer was dried (Na$_2$SO$_4$) and concentrated to give the ester compound (6.2 g, ~100%). $^1$H NMR (400 MHz, DMSO-$d_6$) δ: 8.80 (s, 1H), 7.39 (d, 2H), 7.22 (t, 2H), 6.89 (m, 1H), 6.45 (t, 1H), 3.88 (d, 2H), 3.66 (s, 3H).

b) (3-Phenyl-ureido)-acetic acid

Standard basic hydrolysis of the above ester from step a (6.0 g, 28.9 mmol) with lithium hydroxide monohydrate (6.3 g, 150 mmol) yielded the title acid (5.36 g, 95.7%). $^1$H NMR (400 MHz, DMSO-$d_6$) δ: 12.58 (s, 1H), 8.75 (s, 1H), 7.39 (d, 2H), 7.22 (t, 2H), 6.88 (m, 1H), 6.35 (t, 1H), 3.80 (d, 2H).

c) N-{2-[(S)-3-Hydroxy-pyrrolidin-1-yl]-(S)-1-phenyl-ethyl}-N-methyl-N'-pyridin-3-yl-succinamide Coupling of the above acid from step b (427 mg, 2.2 mmol) with 1-(2-methylamino-(S)-2-phenyl-ethyl)-pyrrolidin-(S)-3-ol dihydrochloride (585 mg, 2.0 mmol) using the general method A gave compound 34 (660 mg, 83.3%). $^1$H NMR (400 MHz, DMSO-$d_6$) δ: 8.90 (s, 1H), 7.38–7.22 (m, 9H), 6.88 (t, 1H), 6.40 (t, 1H), 5.79, 5.00 (m, total 1H), 4.70 (m, 1H), 4.18–3.99 (m, 3H), 3.02–2.30 (m, 9H), 1.95 (m, 1H), 1.53 (m, 1H); MS: [M+1]$^+$: 397.

EXAMPLES 35 AND 36

In like manner to Example 34-step c, coupling of the (3-Phenyl-ureido)-acetic acid with 1-(3-methyl-(S)-2-methylamino-butyl)-pyrrolidin-(S)-3-ol or 1-piperidin-(S)-2-ylmethyl-pyrrolidin-(S)-3-ol afforded compound 35 or 36 respectively.

EXAMPLE 35

N-[(S)-1-{(S)-3-Hydroxy-pyrrolidin-1-ylmethyl}-2-methyl-propyl]-N-methyl-2-(3-phenyl-ureido)-acetamide $^1$H NMR (400 MHz, DMSO-$d_6$) δ: 8.90, 8.89 (2s, total 1H), 7.38 (d, 2H), 7.21 (t, 2H), 6.89 (t, 1H), 6.40 (brs, 1H), 4.68 (m, 1H), 4.25–3.90 (m, 3H), 2.80–2.20 (m, 10H), 1.92 (m, 1H), 1.70 (m, 1H), 1.50 (m, 1H), 0.99, 0.93 (2d, total 3H), 0.80, 0.75 (2d, total 3H); MS: [M+1]$^+$: 363.

EXAMPLE 36

4-{(S)-2-[(S)-3-Hydroxy-pyrrolidin-1-ylmethyl]-piperidin-1-yl}-4-oxo-N-phenyl-butyramide $^1$H NMR (400 MHz, DMSO-d$_6$) δ 8.90 (s, 1H), 7.39 (d, 2H), 7.22 (t, 2H), 6.88 (t, 1H), 6.36 (t, 1H), 4.71 (m, 1H), 4.32–3.57 (m, 4H), 3.02–2.40 (m, 8H), 1.95–1.25 (m, 8H); MS: [M+1]$^+$: 361

Biological Assays

Assessment of Analgesic Activity

The pharmacological activity of the compounds of the present invention may be assessed by several art-recognized in vitro and in vivo models. Some of the typical models are described herein.

(a) In Vitro Binding Assay (Primary Screen)

The potencies of the compounds of the invention were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

The receptor binding method was a modification of the method of K. Raynor et al. (*Mol. Pharmacol.* 1994, 45, 330–334). After dilution in buffer A and homogenization as before, membrane proteins (10–80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. K$_i$ values were determined by Cheng-Prusoff corrections of IC$_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors (K$_i$), radioligand bound (cpm) in the presence of various concentrations of test compounds was measured. The concentration to give half-maximal inhibition (EC$_{50}$) of radioligand binding was determined from a best nonlinear regression fit to the following equation, $$Y = \text{Bottom} + \frac{(\text{Top} - \text{Bottom})}{1 + 10^{X - \text{Log}EC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC$_{50}$ is the log of the concentration of test compound where the amount of radioligand bound is half-way between Top and Bottom. The nonlinear regression fit was performed using the program Prism® (GraphPad Software, San Diego, Calif.). The K$_i$ values were then determined from the EC$_{50}$ values by the following equation, $$K_i = \frac{EC_{50}}{1 + \frac{[\text{ligand}]}{K_d}}$$

where [ligand] is the concentration of radioligand and K$_d$ is the equilibrium dissociation constant for the radioligand.

The potencies of the agonists were assessed by their abilities to stimulate [$^{35}$S]GTPγS binding to membranes containing the cloned human κ receptors.

To determine the EC$_{50}$ value, which was the concentration to give half-maximal stimulation of [$^{35}$S]GTPγS binding, the amount of [$^{35}$S]GTPγS bound in the presence of various concentrations of agonists was measured. The EC$_{50}$ value was then determined.

(b) Inflamed Knee Joint Hyperalgesia Model and Blood Pressure Response to Compression of the Inflamed Knee Joint Inflammation in a joint is often associated with hyperalgesia (pain during normal flexion and extension and during the application of gentle innocuous pressure) and/or persistent pain (resting pain; Schaible, et al., *Pain* 55: 5–54, 1993). During the course of knee joint inflammation, a cascade of events occurs, which includes: (i) synthesis and release of inflammatory mediators in the joint, (ii) release of neuropeptides from afferent fibers in the joint cavity, and (iii) increased primary afferent outflow from group II, III, IV sensory fibers (Schaible, et al., *Pain* 55: 5–54, 1993). An important result of this cascade is that there is an augmentation in the response of small, lightly myelinated and unmyelinated afferents to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension (Schaible, et al, *J. Neurophysiol.* 54: 1109–1122, 1993) and signs of a pain-associated autonomic reaction (Sata, et al., *Neurosci. Lett.* 52: 55–60, 1984).

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, suggesting an ongoing pain state. According to electrophysiological studies, in the course of the development of this acute arthritis, C and Ad units normally responding only to extreme joint distortion become activated by slight movement (Schaible, et al., *J. Neurophysiol.* 54: 1109–1122, 1985). Spinal neurons with knee joint receptive fields in the deep dorsal horn of the spinal cord show clear development of hyperexcitability with the acute inflammation in the joint (Neugebauer, et al., *J. Neurosci.* 70: 1365–1377, 1993). This sensitization of group III and IV fibers was observed within 2–3 hours after injection of kaolin and carrageenan into the knee joint, a time course that closely matches the time course of the development of hyperalgesia in the rat knee joint compression model. These observations indicate that spinal cord neurons and joint primary afferent fibers become sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle (Williamson, et al., *J. Physiol.* 475: 351–357, 1994). This response is dependent on the changes in intramuscular pressure and the quality of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and A units was observed in the rat gastroonemius muscle by infiltration with carrageenan (Handwerker et al., *Pain and Inflammation*, Proceeding of the VI$^{th}$ World Congress on Pain, Bond et al. eds., Elsevier Science Publishers BV, 59–70, 1991). Based on these considerations, it appears that compression of the inflamed knee joint yields a noxious stimulus and this in turn activates a sympathetic response resulting in an increase in BP.

Local inflammation of the knee results in a state where otherwise innocuous stimuli results in a prominent autonomic response, including increased blood pressure (BP) and heart rate (See, e.g., Sata et al., *Neurosci. Lett.* 52: 55–60, 1984). Alternatively, neural outflow from the inflamed knee is recorded (See, e.g. Neugebauer et al., *J. Neurosci.* 70: 1365–1377, 1993).

An in vitro test that measures spontaneous discharge in injured skin by topical application may also be used. (See, e.g., Andreev et al., *Neurosci.* 58: 793–798, 1994).

(c) In Vivo Evaluation of Formalin-Induced Nociception

Administration of formalin into the paw results in a localized inflammation and a pain response that is moderate in intensity and continuous in duration. Unlike many other assays of nociception, the formalin assay measures tonic pain that is a result of tissue injury, and therefore is a model that is more relevant to clinical pain states in humans (See Tjolsen et al., *Pain* 51: 5–17, 1992). In the rat the response to formalin-induced pain consists of spontaneous flinching behavior, characterized by paw lifting and paw shaking, and a rapid vibration of the paw after drawing it under the body. The flinching response can be reliably quantified and exhibits two peaks of activity that are indicative of acute and tonic pain (Wheeler-Aceto and Cowan, *Psychopharmacology* 104: 35–44, 1991). The early or acute phase lasts from 0–5 minutes post-formalin and is followed by a quiescent period lasting approximately 15 minutes. The tonic phase occurs from 20–35 minutes following formalin injection and is the interval where the number of flinching responses is maximal. This model has been characterized in several species (Tjolsen et al., *Pain* 51: 5–17, 1992) and is sensitive to the analgesic effects of opiates administered by a variety of routes, including local administration directly into the paw. In addition, the test is particularly sensitive to the effects of κ agonists (Wheeler-Aceto and Cowan, *Psychopharmacology* 104: 35–44, 1991).

Inflammation is induced by subcutaneous injection of 50 ml of a 5% formalin solution into the dorsal surface of the right hind paw of male Sprague-Dawley rats weighing 70–90 g. Injections of drug are given into the dorsal surface of the paw prior to formalin injection, and flinching behavior is quantified by counting the number of responses that occur during the tonic phase of pain, lasting from 20–35 minutes after formalin injection. Results are expressed as the mean percent antagonism of formalin-induced flinching calculated for individual drug-treated, formalin-injected rats using the following formula:

(mean formalin response–mean saline response)–individual response×100(mean formalin response-mean saline response)

The mean formalin response is the mean behavioral score of vehicle-treated and formalin-injected rats. The mean saline response is the pooled behavioral score from rats injected with 50 ml of saline into the paw.

(d) Randall-selitto Test

Numerous variations and exemplifications of this assay are known to those of skill in this art (See, Randall, et al., *Arch. Int. Pharmacodyn.* 111: 409–419, 1957; See, also, e.g., U.S. Pat. No. 5,434,292, U.S. Pat. No. 5,369,131, U.S. Pat. No. 5,345,943, U.S. Pat. No. 5,242,944 and U.S. Pat. No. 5,109,135.

The pain threshold is measured in this method as the amount of pressure in grams required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined.

Stein and coworkers (Stein et al., *Pharmacol. Biochem. Behav.* 31: 445–451, 1988; Stein, et al., *J. Pharmacol. Exp. Ther.* 248: 1269–1275, 1989) have developed a model of peripheral inflammation and hyperalgesia in rats, which supports the role of opiates in mediating peripheral analgesia. In this protocol, modified Freund's adjuvant is used as the inflammatory stimulus, and the paw pressure test is used to assess the response of the rat to a painful pressure stimulus. The model is sensitive to opiate agonists of the μ, δ and κ subtypes, which produce analgesia upon administration (Antonijevic, et al., *J. Neurosci.* 15: 165–172, 1995; Stein, et al., *Neurosci. Lett.* 84: 225–228, 1988; Stein, et al., *J. Pharmacol. Exp. Ther.* 248: 1269–1275, 1989). Histological verification of opiate receptor localization and density have confirmed that peripheral opiate receptors are accessible on primary afferent nerve fibers and are upregulated following inflammation (Hassan et al., *Neuroscience* 55: 185–193, 1993; Przewlocki et al., *Neuroscience* 48: 491–500, 1992).

Experiments are conducted in rats weighing 150–250 g at the time of inoculation. Modified Freund's complete adjuvant (FCA) is used as the inflammatory stimulus. Rats are administered an i.pl. injection of the FCA suspension into the right hind foot. Hyperalgesia and antinociception are evaluated using the paw pressure test. The rat is gently restrained and incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. A cutoff pressure of 250 g is used to avoid undue stress and pain to the animal.

Baseline responding is established by determining the average of three consecutive trials separated by 10 seconds. The same procedure is conducted on the contralateral side and the sequence of sides is alternated between animals to control for order effects. Typically injections are not made in the contralateral (noninflamed) paw; however, in selected cases drugs may be administered to the contralateral paw to evaluate the potential for drug effects in the absence of inflammation.

Analgesic activity is determined by expressing the increase in PPT resulting from the effect of the drug as a percentage of basal pre-injection thresholds.

Hyperalgesia can also be produced by inflammatory stimuli such as yeast or carrageenan, endogenous inflammatory mediators such as bradykinin or prostaglandins, or other types of chemical irritants (See Hargreaves and Joris, *APS Journal* 2: 51–59, 1993).

(e) Acetic Acid-Induced Writhing

This test identifies novel agents that exhibit peripheral analgesic activity against visceral or chemical pain (See Barber and Gottschlich, *Med. Res. Rev.* 12: 525–562, 1986; Ramabadran and Bansinath, *Pharm. Res.* 3: 263–270, 1986). Injection of acetic acid into the peritoneal cavity is used as the noxious stimulus, and the number of writhing responses that occur in response to acetic acid are counted in order to quantify the response to pain. Compounds which possess analgesic activity reduce the number of writhing responses that occur. Opiate agonists of the μ and κ subtype exhibit analgesic activity in this model (Barber and Gottschlich, *Med. Res. Rev.* 12: 525–562, 1986; Millan, *Trends Pharmacol. Sci.* 11: 70–76, 1990). Novel compounds that demonstrate potency and efficacy in this assay are potential drugs for the treatment of various pathological conditions involving peripheral pain.

The writhing assay is adapted from the procedure originally described by Taber, et al. (*J. Pharmacol. Exp. Ther.* 169: 29–38, 1986), using male CF-1 mice weighing 20–25 g. Animals are treated with various doses of drugs prior to the administration of an i.p. injection of 0.6% acetic acid solution. Mice are then placed into observation chambers and the number of writhing responses, as defined by a full hind limb extension and retraction, are recorded.

The mean number of writhing responses is calculated for vehicle-treated control mice, and the percent inhibition (% I) of writhing is calculated for each mouse that is treated with drug using the following formula:

% $I$=100×(mean control writhing responses–individual test responses)(mean control writhing responses)

(f) Hyperalgesia Induced by Tape Stripping

The objective of this assay is to identify novel agents which exhibit peripherally-mediated analgesia in circumstances, such as burns and abrasions, which lead to hyperalgesia. In such injuries, the loss of the stratum corneum is followed by an inflammatory response (erythema) and a painful response to otherwise innocuous stimuli. Removal of the stratum corneum by repeated application and removal of cellophane tape, termed tape stripping, has been shown to be a simplified model of these injuries, which share characteristics of first degree burns (See Flynn, *Percutaneous Absorption*, R. L. Bronaugh and H. I. Maibach, eds., Marcel Dekker Inc., 18–42, 1985). This method of barrier disruption avoids the application of potentially toxic chemicals and permits evaluation of peripheral analgesics following topical administration because tape stripping removes the barrier to effective topical therapy (the stratum corneum) while simultaneously resulting in inflammation and hyperalgesia. Tape stripping has been validated in humans as a model for the testing of topical agents (Pershing, et al., *Antimicrob. Agents Chemother;* 38: 90–95, 1994; Roy and Flynn, *Pharm. Res.* 7: 842–847, 1990).

Experiments are conducted in male Sprague-Dawley rats weighing 250–500 g at the time of treatment. After anesthesia of the rat with ketamine-xylamine, a 1–3 cm² patch of rat skin is treated by repeated application and removal of tape. This procedure results in removal of the stratum corneum as determined by a glistening appearance of the skin. The tape stripped skin is evaluated for a visible erythema and for sensitivity to contact by heat or pressure stimuli using a focused beam of light, by testing in the paw pressure apparatus or by touch with von Frey hairs. The diameter of the von Frey hairs will be selected based on a diameter which causes no response in control rats but has a readily detectable response in treated rats.

Typically analgesics will be formulated in a suitable topical medium and applied to the treated skin. Some rats will receive only the topical medium without analgesic to control for an effect of the topical medium alone. The presence of analgesia is determined by the latency to respond to the heat stimulus or by response to touch or pressure.

Compounds in all the examples showed κ receptor affinity ($K_i$) <10 micromolar. For example, compound of Example 1 had a $K_i$=0.17 nM against the human κ receptor with >100× selectivity versus the human μ and δ receptors and was an agonist with an $EC_{50}$=0.05 nM. Compound of Example 1 exhibited a % A=96.2% at a dose of 300 μg, i.paw in the in vivo formalin-induced nociception assay. This compound also blocked the action of acetic acid-induced writhing when administered subcutaneously with an $ED_{50}$=0.017 mg/kg.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula Ia or Ib:

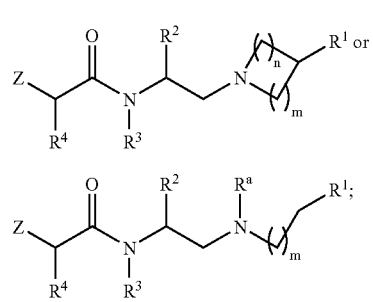

wherein:
R¹ is H or OH;
$R^a$ is alkyl;
R² is alkyl, aryl, or aralkyl;

R$^3$ is alkyl, or R$^2$ and R$^3$ taken together with the atoms through which they are connected form a 4- to 8-membered heterocyclic ring;
R$^4$ is H, alkyl, cycloalkyl, alkylcycloalkyl, aryl, aralkyl, heteroaryl, or heteroarylalkyl;
Z is —(CH$_2$)$_o$—NR$^5$R$^6$ or —(CH$_2$)$_o$—C(=O)NR$^7$R$^8$;
R$^5$ is H, alkyl, or aryl;
R$^6$ is aryl, alkaryl, —CO(NH)$_p$R$^9$, or —SO$_2$R$^9$, provided that at least one of R$^5$ and R$^6$ is other than aryl;
R$^7$ is H or alkyl;
R$^8$ is alkyl, aryl, aralkyl, alkaryl, heteroaryl, heteroarylalkyl, cycloalkyl or cycloalkylalkyl;
R$^9$ is alkyl, cycloalkyl, alkylcycloalkyl, aryl, aralkyl, heteroaryl, or heteroarylalkyl;
m is the integer 1, 2, or 3;
n is the integer 1, 2, or 3;
o is the integer 0, 1, 2, or 3;
p is the integer 0 or 1; and
the quantity (m+n) is an integer in the range of 2 to 5;
or a stereoisomer, prodrug, pharmaceutically acceptable salt, hydrate, solvate, acid salt hydrate, N-oxide or isomorphic crystalline form thereof.

2. A compound according to claim 1,
wherein the quantity (m+n) is 3.

3. A compound according to claim 1,
wherein o is the integer 0 or 1.

4. A compound according to claim 1,
wherein R$^1$ is —OH.

5. A compound according to claim 1,
wherein R$^2$ is aryl.

6. A compound according to claim 5,
wherein the R$^2$ is phenyl.

7. A compound according to claim 1,
wherein R$^2$ is alkyl.

8. A compound according to claim 7,
wherein R$^2$ is prop-2-yl.

9. A compound according to claim 1,
wherein R$^3$ is methyl.

10. A compound according to claim 1,
wherein R$^2$ and R$^3$ taken together with the atoms through which they are connected form a 4- to 8-membered heterocyclic ring.

11. A compound according to claim 10,
wherein R$^2$ and R$^3$ taken together with the atoms through which they are connected form a 5- to 6-membered heterocyclic ring.

12. A compound according to claim 1,
wherein R$^4$ is H.

13. A compound according to claim 1,
wherein Z is —NR$^5$R$^6$ or —(CH$_2$)$_o$—C(=O)NR$^7$R$^8$.

14. A compound according to claim 13,
wherein R$^5$ is alkyl or aryl.

15. A compound according to claim 14,
wherein the R$^5$ is methyl or phenyl.

16. A compound according to claim 1,
wherein R$^5$ is H.

17. A compound according to claim 1,
wherein R$^6$ is aryl.

18. A compound according to claim 17,
wherein R$^6$ is phenyl.

19. A compound according to claim 18,
wherein R$^6$ is phenyl substituted with —CN, —NO$_2$, —NHS(=O)$_2$(alkyl), halo, or —CF$_3$.

20. A compound according to claim 18,
wherein R$^6$ is phenyl substituted with chloro.

21. A compound according to claim 1,
wherein R$^6$ is alkaryl.

22. A compound according to claim 1,
wherein R$^7$ is H.

23. A compound according to claim 1,
wherein R$^9$ is alkyl.

24. A compound according to claim 23,
wherein p is 0.

25. A compound according to claim 1,
wherein R$^9$ is aryl.

26. A compound according to claim 25,
wherein p is 1.

27. A compound according to claim 26,
wherein R$^9$ is phenyl.

28. A compound according to claim 1, of formula Ia or IIb:

29. A compound according to claim 28, of formula IIc or IId:

30. A compound according to claim 29,
wherein:
R$^2$ is aryl or alkyl;
R$^3$ is alkyl;
Z is —NR$^5$R$^6$ or —(CH$_2$)$_o$—C(=O)NR$^7$R$^8$;
R$^7$ is H;
R$^8$ is aryl, aralkyl, heteroaryl, or alkaryl; and
o is the integer 0 or 1.

31. A compound according to claim 30, wherein R$^6$ is aryl, alkaryl, or —CO(NH)$_p$R$^9$.

32. A compound according to claim 30 of formula III:

33. A compound according to claim 32,
wherein:
R$^1$ is OH;
R$^2$ is phenyl or prop-2-yl;
R$^5$ is H, methyl, or phenyl; and
R$^9$ is alkyl.

34. A compound according to claim 33,
wherein:
R² is phenyl;
R⁵ is H;
R⁶ is phenyl or meta-methylphenyl;
R⁷ is H; and
R⁸ is phenyl or heteroaryl.

35. A compound according to claim 34,
wherein Z is NH(phenyl).

36. A compound according to claim 35,
wherein the phenyl in Z is substituted with —NHS(=O)₂-alkyl.

37. A compound according to claim 36,
wherein the alkyl in —NHS(=O)₂-alkyl is methyl.

38. A compound according to claim 36,
wherein the alkyl in —NHS(=O)₂-alkyl is n-propyl.

39. A compound according to claim 35,
wherein the phenyl in Z is unsubstituted.

40. A compound according to claim 34,
wherein Z is —CH₂C(=O)NH(unsubstituted phenyl).

41. A compound according to claim 34,
wherein Z is —C(=O)NH(unsubstituted phenyl).

42. A compound according to claim 1, wherein said compound is:
N-{2-[(S)-3-hydroxy-pyrrolidin-1-yl]-(S)-1-phenyl-ethyl}-N-methyl-2-phenylamino-acetamide;
N-{2-[(S)-3-hydroxy-pyrrolidin-1-yl]-(S)-1-phenyl-ethyl}-N-methyl-2-(methyl-phenyl-amino)-acetamide;
2-(acetyl-phenyl-amino)-N-{2-[(S)-3-hydroxy-pyrrolidin-1-yl]-(S)-1-phenyl-ethyl]-(S)-1-phenyl-ethyl}-N-methyl-acetamide;
2-(4-cyano-phenylamino)-N-{2-[(S)-3-hydroxy-pyrrolidin-1-yl]-(S)-1-phenyl-ethyl}-N-methyl-acetamide;
2-(3-cyano-phenylamino)-N-{2-[(S)-3-hydroxy-pyrrolidin-1-yl]-(S)-1-phenyl-ethyl}-N-methyl-acetamide;
2-(2-cyano-phenylamino)-N-{2-[(S)-3-hydroxy-pyrrolidin-1-yl]-(S)-1-phenyl-ethyl}-N-methyl-acetamide;
2-(4-aminomethyl-phenylamino)-N-{2-[(S)-3-hydroxy-pyrrolidin-1-yl]-(S)-1-phenyl-ethyl}-N-methyl-acetamide;
2-[(4-cyano-phenyl)-methyl-amino]-N-{2-[(S)-3-hydroxy-pyrrolidin-1-yl]-(S)-1-phenyl-ethyl}-N-methyl-acetamide;
N-{2-[(S)-3-hydroxy-pyrrolidin-1-yl]-(S)-1-phenyl-ethyl}-2-[4-(methanesulfonylamino-methyl)-phenylamino]-N-methyl-acetamide;
N-{2-[(S)-3-hydroxy-pyrrolidin-1-yl]-(S)-1-phenyl-ethyl}-2-[3-(methanesulfonylamino-methyl)-phenylamino]-N-methyl-acetamide;
N-{2-[(S)-3-hydroxy-pyrrolidin-1-yl]-(S)-1-phenyl-ethyl}-2-[2-(methanesulfonylamino-methyl)-phenylamino]-N-methyl-acetamide;
2-(3,4-dichloro-phenylamino)-N-{2-[(S)-3-hydroxy-pyrrolidin-1-yl]-(S)-1-phenyl-ethyl}-N-methyl-acetamide;
2-(4-trifluoromethyl-phenylamino)-N-{2-[(S)-3-hydroxy-pyrrolidin-1-yl]-(S)-1-phenyl-ethyl}-N-methyl-acetamide;
2-[(2,4-dichloro-phenyl)-methanesulfonyl-amino]-N-{2-[(S)-3-hydroxy-pyrrolidin-1-yl]-(S)-1-phenyl-ethyl}-N-methyl-acetamide;
2-(4-nitro-phenylamino)-N-{2-[(S)-3-hydroxy-pyrrolidin-1-yl]-(S)-1-phenyl-ethyl}-N-methyl-acetamide;
N-{2-[(S)-3-hydroxy-pyrrolidin-1-yl]-(S)-1-phenyl-ethyl}-2-(4-methanesulfonylamino-phenylamino)-N-methyl-acetamide;
N-{2-[(S)-3-hydroxy-pyrrolidin-1-yl]-(S)-1-phenyl-ethyl}-2-(4-propanesulfonylamino-phenylamino)-N-methyl-acetamide;
N-{(S)-1-[(S)-3-hydroxy-pyrrolidin-1-ylmethyl]-2-methyl-propyl}-N-methyl-2-[4-(propane-1-sulfonylamino)-phenylamino]-acetamide;
propane-1-sulfonic acid (4-{2-[2-(S)-{(S)-3-hydroxy-pyrrolidin-1-ylmethyl]-piperidin-1-yl]-2-oxo-ethylamino}-phenyl)-amide;
N-{2-[(S)-3-hydroxy-pyrrolidin-1-yl]-(S)-1-phenyl-ethyl}-N-methyl-N'-phenyl-malonamide;
N-{2-[(2-hydroxy-ethyl)-methyl-amino]-(S)-1-phenyl-ethyl}-N-methyl-N'-phenyl-malonamide;
N-[⁴-(methanesulfonylamino-methyl)-phenyl]-N'-{2-[(S)-3-hydroxy-pyrrolidin-1-yl]-(S)-1-phenyl-ethyl}-N'-methyl-malonamide;
N-[⁴-(ethanesulfonylamino-methyl)-phenyl]-N'-{2-[(S)-3-hydroxy-pyrrolidin-1-yl]-(S)-1-phenyl-ethyl}-N'-methyl-malonamide;
N-{2-[(S)-3-hydroxy-pyrrolidin-1-yl]-(S)-1-phenyl-ethyl}-N'-(4-methanesulfonylamino-phenyl)-N-methyl-malonamide;
N-{2-[(S)-3-hydroxy-pyrrolidin-1-yl]-(S)-1-phenyl-ethyl}-N-methyl-N'-[2-(pyrrolidine-1-sulfonyl)-phenyl]-malonamide;
N-benzyl-N'-{2-[(S)-3-hydroxy-pyrrolidin-1-yl]-(S)-1-phenyl-ethyl}-N'-methyl-malonamide;
N-{2-[(S)-3-hydroxy-pyrrolidin-1-yl]-(S)-1-phenyl-ethyl}-N-methyl-N'-thiazol-2-yl-malonamide;
N-{2-[(S)-3-hydroxy-pyrrolidin-1-yl]-(S)-1-phenyl-ethyl}-N-methyl-N'-pyridin-3-yl-malonamide;
N-{2-[(S)-3-hydroxy-pyrrolidin-1-yl]-(S)-1-phenyl-ethyl}-N-methyl-N'-phenyl-succinimide;
N-[(S)-1-{(S)-3-hydroxy-pyrrolidin-1-ylmethyl}-2-methyl-propyl]-N-methyl-N'-phenyl-succinamide;
4-{(S)-2-[(S)-3-hydroxy-pyrrolidin-1-ylmethyl]-piperidin-1-yl}-4-oxo-N-phenyl-butyramide;
N-{2-[(S)-3-hydroxy-pyrrolidin-1-yl]-(S)-1-phenyl-ethyl}-N-methyl-N'-thiazol-2-yl-succinamide;
N-{2-[(S)-3-hydroxy-pyrrolidin-1-yl]-(S)-1-phenyl-ethyl}-N-methyl-N'-pyridin-3-yl-succinamide;
N-{2-[(S)-3-hydroxy-pyrrolidin-1-yl]-(S)-1-phenyl-ethyl}-N-methyl-2-(3-phenyl-ureido)-acetamide;
N-[(S)-1-{(S)-3-hydroxy-pyrrolidin-1-ylmethyl}-2-methyl-propyl]-N-methyl-2-(3-phenyl-ureido)-acetamide;
4-{(S)-2-[(S)-3-hydroxy-pyrrolidin-1-ylmethyl]-piperidin-1-yl}-4-oxo-N-phenyl-butyramide; or
a stereoisomer, a prodrug, a pharmaceutically acceptable salt, a hydrate, a solvate, an acid salt hydrate, an N-oxide or an isomorphic crystalline form thereof.

43. A pharmaceutical composition, comprising:
at least one pharmaceutically acceptable carrier; and
at least one compound according to claim 1.

44. A pharmaceutical composition according to claim 43, further comprising at least one opioid.

45. A pharmaceutical composition according to claim 44, wherein said opioid is selected from the group consisting of alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, and mixtures thereof.

46. A pharmaceutical composition according to claim 43, further comprising at least one compound selected from the group consisting of antibiotics, antivirals, antifungals, anti-inflammatories, anesthetics, and mixtures thereof.

* * * * *